_US005607953A_

United States Patent [19]

Minami et al.

[11] Patent Number: 5,607,953
[45] Date of Patent: Mar. 4, 1997

[54] BUTENOIC OR PROPENOIC ACID DERIVATIVE

[75] Inventors: Norio Minami; Fumihiro Ozaki; Keiji Ishibashi; Yasuhiro Kabasawa; Megumi Ikemori; Toshiaki Ogawa; Takanori Kawamura, all of Ibaraki, Japan

[73] Assignee: Eisai Co., Ltd., Tokyo, Japan

[21] Appl. No.: 347,099

[22] Filed: Nov. 23, 1994

Related U.S. Application Data

[62] Division of Ser. No. 959,654, Oct. 13, 1992, Pat. No. 5,382,595, which is a division of Ser. No. 557,713, Jul. 25, 1990, Pat. No. 5,177,089, which is a division of Ser. No. 354,306, May 19, 1989, Pat. No. 5,047,417.

[30] Foreign Application Priority Data

Jun. 1, 1988 [JP] Japan .................................. 63-134892

[51] Int. Cl.$^6$ .................... A61K 31/335; A61K 31/34; A61K 31/38; A64K 31/40; C07D 403/06; C07D 233/66; C07D 213/63; C07D 319/14

[52] U.S. Cl. ................... 514/327; 514/397; 514/398; 514/399; 514/400; 514/428; 514/617; 540/575; 540/594; 544/139; 544/163; 544/165; 544/166; 544/168; 544/229; 544/239; 544/283; 544/336; 544/353; 544/393; 546/121; 546/146; 546/173; 546/210; 546/216; 546/221; 546/247; 546/291; 546/337; 546/277.4; 546/276.4; 548/189; 548/236; 548/247; 548/249; 548/300.1; 548/378; 548/485; 548/491; 548/495; 548/501; 548/361.1; 548/373.1; 558/415; 564/161; 564/162

[58] Field of Search .................... 564/161, 182; 546/716, 121, 146, 173, 210, 221, 247, 270, 278, 291, 337; 558/415; 548/300.1, 336, 337, 341, 342, 204, 187, 189, 236, 247, 249, 372, 378, 455, 485, 491, 495, 501; 514/327, 428, 617, 397, 398, 399, 400; 540/594, 575; 544/353, 139, 163, 165, 166, 168, 224, 239, 283, 336, 393

[56] References Cited

U.S. PATENT DOCUMENTS 4,010,191  3/1977  Thiele et al. .......................... 424/312

4,190,674  2/1980  Grivsky ............................... 424/324
4,536,346  8/1985  Shepherd et al. ..................... 560/21
4,812,473  3/1989  Kuwano et al. ...................... 514/396

FOREIGN PATENT DOCUMENTS

| 0209843 | 1/1987 | European Pat. Off. . |
| 0229391 | 7/1987 | European Pat. Off. . |
| 0326106 | 8/1989 | European Pat. Off. . |
| 2428632 | 1/1980 | France . |
| 3242344 | 5/1984 | Germany . |
| 4714585 | 8/1972 | Japan . |
| 1218571 | 9/1986 | Japan . |
| 62-90289 | 4/1987 | Japan . |
| 62-94386 | 4/1987 | Japan . |
| 1157891 | 6/1989 | Japan . |
| 2067562 | 7/1981 | United Kingdom . |
| 2192394 | 1/1988 | United Kingdom . |
| 8402907 | 8/1984 | WIPO . |
| 8803531 | 5/1988 | WIPO . |

OTHER PUBLICATIONS

Chemical Abstracts, vol. 84, No. 15, p. 708 (1981) No. 121586v.
Chemical Abstracts, vol. 77, No. 7, p. 498 (1972) No. 48525s.
Chemical Abstracts, vol. 79, No. 11, p. 455 (1973) No. 66414A.
Chemical Abstracts, vol. 97, No. 25, p. 859 (1982) No. 2166229g.
Chemical Abstracts, vol. 83, No. 9, p. 660 (1975) No. 79194m.

*Primary Examiner*—C. Warren Ivy
*Assistant Examiner*—Raymond Covington
*Attorney, Agent, or Firm*—Birch, Stewart, Kolasch & Birch, LLP

[57] ABSTRACT

A butenoic or propenoic acid derivative having the following formula in which G is an aryl or a heterocyclic ring, R11 and R12 are hydroben or an alkyl, X is sulfur or oxygen, R2 and R3 are hydrogen, an substituent such as an alkyl and J is pyridyl or phenyl having substituents and a heterocyclic ring may be formed between R2, R3 and J is provided here and is useful in the pharmacological field.

$$G-\underset{\underset{}{\,}}{\overset{R^{11}}{C}}=\underset{\underset{}{\,}}{\overset{R^{12}}{C}}-(CH_2)_m-\overset{\overset{X}{\|}}{C}-\underset{\underset{R^2}{|}}{N}-A-\underset{\underset{R^3}{|}}{N}-(CH_2)_n-J \qquad (II)$$

16 Claims, No Drawings

BUTENOIC OR PROPENOIC ACID DERIVATIVE

This application is a divisional of application Ser. No. 07/959,654, filed on Oct. 13, 1992, now U.S. Pat. No. 5,382,595 which is a divisional of application Ser. No. 07/557,713, filed on Jul. 25, 1990, now U.S. Pat. No. 5,177,089, which is a divisional of application Ser. No. 07/354,306, filed on May 19, 1989, now U.S. Pat. No. 5,047,417, the entire contents of which are hereby incorporated by reference.

The invention relates to a butenoic or propenoic acid derivative having phenyl or a heterocyclic ring at its omega position. It is useful as a drug, in particular having an excellent coronary vasodilating and heart rate lowering effect.

PRIOR ARTS

In countries of Europe and America, cardiovascular diseases head the list of death causes. In Japan, although cerebrovascular diseases such as cerebral apoplexy ranked high in the list of the death causes, ischemic heart disease has prominently increased recently, as the life-style and eating habit of Japanese have neared those of European and American.

Ischemic heart disease generally refers to a series of heart diseases caused when the supply of oxygen to cardiac muscle cannot make up for myocardial oxygen consumption. Representative examples thereof include coronary sclerosis, acute cardiac infarction and angina pectoris. Although nitro drugs, calcium antagonists and β-blockers are now generally used for the treatment of these diseases, no decisively effective drug has been found as yet, so that it is highly expected to develop a novel drug more excellent than those of the prior art.

SUMMARY OF THE INVENTION

Under these circumstances, the inventors of the present invention have attempted to develop a new type of a remedy for ischemic heart disease. Particularly, the inventors have long studied to find out a compound which exhibits excellent coronary vasodilating and heart rate lowering effects.

The invention provides a butenoic or propenoic acid derivative having the formula (II) and a pharmacologically accepatable salt thereof:

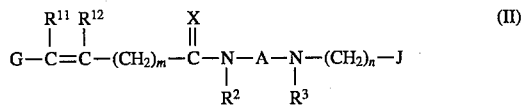

which is defined by each of the following definitions (I), (II) and (III):

(I) having the formula (I) in which in the formula (II) G is R1-phenyl, R11 and R12 each are hydrogen, m is one and X is oxygen,

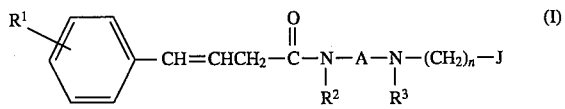

wherein R1 is a hetero-aryl group, R2 and R3 each are hydrogen, a lower alkyl, a cycloalkyl or an allyl group, or R2 and R3 may form a 5- to 7-membered saturated heterocyclic ring together with the nitrogen atom to which they are bonded, A is an alkylene group having 1 to 6 carbon atoms, which alkylene may have a lower alkyl, a lower alkoxy or hydroxy, J is pyridyl or a phenyl having substituents R4, R5 and R6:

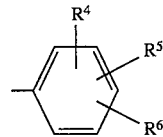

which R4, R5 and R6 each are hydrogen, a halogen atom, a lower alkyl, a lower alkoxy, hydroxy, nitro, cyano, trifluromethyl, an alkylsulfonyloxy, —NR7R8, R7 and R8 being hydrogen or a lower alkyl, or an alkanoylamino, or two of R4, R5 and R6 may form an alkylenedioxy together with two adjacent carbon atoms on the phenyl, or R4, R5 and R6 may form a 5- to 7-membered ring together with the —(CH2)—, and n is an integer of from 1 to 6;

(II) having the formula (II) in which:

G is naphthyl or a phenyl having substituents R15 and R16:

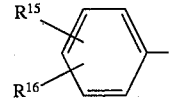

R15 and R16 being hydrogen, a lower alkyl, a lower alkoxy, a halogen, —NR7R8, R7 and R8 being hydrogen or a lower alkyl, cyano, trifluromethyl, an alkanoylamino, trifluoroalkoxy, an alkylsulfonyl, nitro, hydroxyl, an alkylthio, an alkylsulfonylamino, an alkylcarbonylamino or a carbamoyl, or R15 and R16 may form a cyclic ring together with oxygen between two adjacent carbon atoms, R11 and R12 each are hydrogen, cyano, a lower alkyl, or a halogen or they may form a cyclic ring together with oxygen and the carbon on the phenyl, m is zero or 1, X is oxygen or sulfur, R2 and R3 each are hydrogen, a lower alkyl, a lower alkoxy, a cycloalkyl, a trifluoroalkyl or a lower alkenyl, or R2 and R3 may form a 5- to 7-membered saturated heterocyclic ring together with the nitrogen atom to which they are bonded, or R2 may form a ring together with R12, or R3 may form a ring having a nitrogen atom together with the —(CH2)n—, R2 may form a 5- to 7-membered saturated heterocylic ring together with A, R3 may form a 5- to 7-membered saturated heterocyclic ring together with A, A is an alkylene group having 1 to 6 carbon atoms, which alkylene may have a lower alkyl group, n is an integer of 1 to 6, J is pyridyl or a phenyl having substituents R4, R5 and R6:

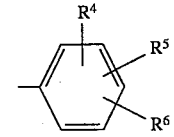

which R4, R5 and R6 each are hydrogen, a halogen atom, a lower alkyl, a lower alkoxy, hydroxy, nitro, trifluromethyl, an alkylsulfonyloxy, —NR7R8, R7 and R8 being hydrogen or a lower alkyl, or an alkanoylamyl, or two of R4, R5 and R6 may form an alkylenedioxy together with two adjacent carbon atoms on the phenyl, or J may form a cyclic ring having a nitrogen together with the group —(CH2) n—; and (III) having the formula (III) in which in the formula (II) R11 and R12 are hydrogen, X is oxygen,

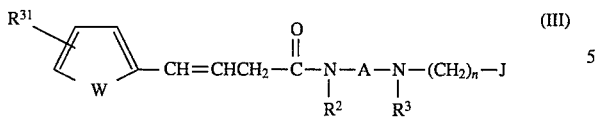

wherein R31 is a hetero-aryl group, R2 and R3 each are hydrogen, a lower alkyl, a cycloalkyl or allyl, or R3 may form a 5- to 7-membered saturated heterocyclic ring together with the nitrogen and the —(CH2)n—, or R3 may form a 5- to 7-membered cyclic heteroring having nitrogen or nitrogen and oxygen together with A and the nitrogen, A is an alkylene having 1 to 3 carbon atoms which may have a lower alkyl, hydroxy or a lower alkoxy group, W is oxygen, sulfur, vinylene (—C=C—) or azomethyne (—N=CH—), J is pyridyl or a phenyl having substituents R4, R5 and R6, which is hydrogen, a halogen, a lower alkyl, a lower alkoxy, hydroxy, nitro, cyano, trifluromethyl, an alkylsulfonyloxy, —NR7R8, R7 and R8 being hydrogen or a lower alkyl group, or an alkanoylamino, or two of R4, R5 and R6 may form an alkylenedioxy together with two adjacent carbon atoms on the phenyl, one of R4, R5 and R6 may form a 5- to 7-membered cyclic ring together with the group —(CH2)n—, n is an integer of 1 to 6, —(CH2)n— may have a lower alkyl.

When one of R4, R5 and R6 forms a fine ring with —(CH2)n—, the following are preferable:

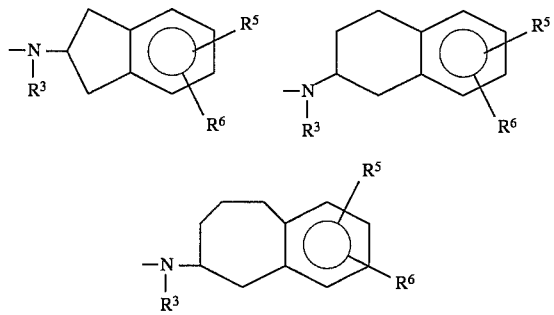

In the above shown definitions I, II and III, two of more symbols are defined independently of each other when they are defined at the same time. Namely they may have either the same definitions as each other or different definitions from each other.

The pharmacologically acceptable salt according to the present invention includes inorganic acid salts such as hydrochloride, sulfate, hydrobromide and phosphate and organic acid salts such as formate, acetate, trifluoroacetate, maleate, fumarate, tartrate, methanesulfonate, benzenesulfonate and toluenesulfonate.

Although the compound of the present invention has an asymmetric carbon atom depending upon the kind of a substituent to be present as optical isomers, it is a matter of course that these optical isomers fall within the scope of the present invention.

The compound of the invention includes the three groups of its embodiments, (I), (II) and (III):

(I) a 4-phenyl-3-butenoic acid derivative having the formula (I) and the definition (I) and a pharmacologically acceptable salt thereof;

(II) a butenoic or propionic acid derivative having the formula (II) and the definition (II) and a pharmacologically acceptable salt thereof; and (III) a 4-aryl-3-butenoic acid derivative having the formula (III) and the definition (III) and a pharmacologically acceptabel salt thereof.

The compound of the invention will be described below more in detail in reference to the embodiments (I), (II) and (III).

EMBODIMENT (I)

The inventors of the present invention have long studied to find out a compound satisfying the above object and have found that a 4-phenyl-3 butenoic acid derivative represented by the general formula (I) can attain the above object.

Namely, the present invention relates to a 4-phenyl-3-butenoic acid derivative represented by the following general formula or a pharmacologically acceptable salt thereof:

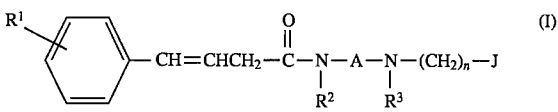

wherein $R^1$ stands for a hetero-aryl group, $R^2$ and $R^3$, which may be the same or different, each stand for a hydrogen atom, a lower alkyl group, a cycloalkyl group or an allyl group, or $R^2$ and $R^3$ form a 5- to 7-membered saturated heterocyclic ring together with the nitrogen atom to which they are bonded, A stands for an alkylene group having 1 to 6 carbon atoms, with the proviso that a lower alkyl group may be bonded to any carbon of the alkylene group, J stands for a group

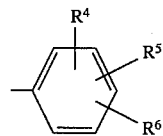

{in which $R^4$, $R^5$ and $R^6$ which may be the same or different, each stand for a hydrogen atom, a halogen atom, a lower alkyl group, a lower alkoxy group, a hydroxyl group, a nitro group, a cyano group, a trifluoromethyl group, an alkylsulfonyloxy group, a group

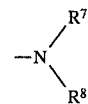

(in which $R^7$ and $R^8$, which may be the same or different, each stand for a hydrogen atom or a lower alkyl group) or an alkanoylamino group, and two of $R^4$, $R^5$ and $R^6$ may form an alkylene-dioxy group between adjacent carbon atoms or R4, R5 or R6 may form a 5- to 7-membered ring together with the group —(CH2)n—) or a pyridyl group, and n is an integer of 1 to 6.

It is preferable that R1 is imidazolyl such as 1-imidazolyl or pyrrolyl such as 1-pyrrolyl and 3-pyrrolyl and n is an integer of 1 to 3.

It is also preferable that J is the phenyl having a substituent(s) such as m,p-dimethoxyphenyl, m-dimethoxyphenyl and m,m,p-trimethoxyphenyl, R4 is a lower alkoxy, R5 is a lower alkoxy and R6 is hydrogen.

It is preferable that R1 is an imidazoyl, R2 is hydrogen, R3 is methyl, J is the phenyl having a substituent(s) and R4, R5 and R6 each are hydrogen or a lower alkoxy.

It is preferable that R1 is an imidazolyl, R2 is hydrogen, R3 is methyl and J is m,p-dimethoxyphenyl.

The lower alkyl group defined with respect to $R^2$, $R^3$, $R^4$, $R^5$, $R^6$, $R^7$ and $R^8$ in formula (I) stands for a straight-chain or branched alkyl group having 1 to 6 carbon atoms and examples thereof include methyl, ethyl, n-propyl, n-butyl, isopropyl, isobutyl, 1-methylpropyl, tert-butyl, n-pentyl, 1-ethylpropyl isoamyl and n-hexyl groups, among which methyl and ethyl groups are most preferred.

The lower alkoxy group defined with respect to $R^4$, $R^5$ and $R^6$ stands for an alkoxy group derived from a lower alkyl group defined above.

The cycloalkyl group defined with respect to $R^2$ and $R^3$ stands for a 3- to 6-membered cycloalkyl group and preferred examples thereof include cyclopentyl and cyclohexyl groups.

The hetero-aryl group defined with respect to $R^1$ stands for a substituted or unsubstituted heterocyclic group, the heterocyclic ring of which may contain one or more nitrogen, oxygen or sulfur atoms. Examples thereof include imidazolyl groups such as 1-imidazolyl and 2-imidazolyl groups; pyridyl groups such as 3-pyridyl and 4-pyridyl groups; pyrrolyl groups such as 1-pyrrolyl and 3-pyrrolyl groups; nitrogenous hetero-aryl groups such as pyrazolyl, indolyl, indazolyl, isoquinolyl, quinolyl, quinoxalinyl, quinazolinyl and imidazopyridyl groups and hetero-aryl groups containing not only a nitrogen atom but also an oxygen atom such as oxazolyl and isoxazolyl groups, among which 1-imidazolyl group is most preferred.

Alternatively, the hetero-aryl group may be substituted with a lower alkyl group such as a methyl group.

When $R^2$ and $R^3$ form a 5- to 7-membered saturated heterocyclic ring together with the nitrogen atom to which they are bonded, the group represented by the formula

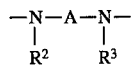

is, for example, a group represented by the formula:

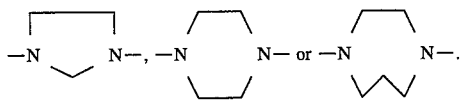

The alkylsulfonyloxy group defined with respect to $R^4$, $R^5$ and $R^6$ may be one derived from a lower alkyl group described above, while the alkanoylamino group may be one derived from a lower alkyl group described above.

A stands for an alkylene group having 1 to 6 carbon atoms, preferably one having about 3 carbon atoms. The alkylene group may have an alkyl group such as a methyl group bonded to any carbon atom thereof.

J stands for a group represented by the formula:

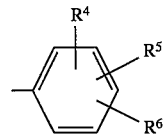

(wherein $R^4$, $R^5$ and $R^6$ are each as defined above) or a pyridyl group. It is preferable that $R^4$, $R^5$ and $R^6$ are each a lower alkoxy group having 1 to 3 carbon atoms, still preferably a methoxy group. The pyridyl group includes 2-pyridyl, 3-pyridyl and 4-pyridyl groups.

Preferable compounds are:

(E)-N-[3-((N'-(2-(3,4-Dimethoxyphenyl)ethyl)-N'-methyl)amino)propyl]-4-(4-(1H-imidazol-1-yl)phenyl)-3-butenamide

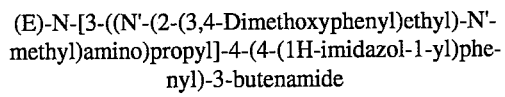

(E)-N-[3-((N'-(2-(3,5-Dimethoxyphenyl)ethyl)-N'-methyl)amino)propyl]-4-(4-(1H-imidazol-1-yl)phenyl)-3-butenamide

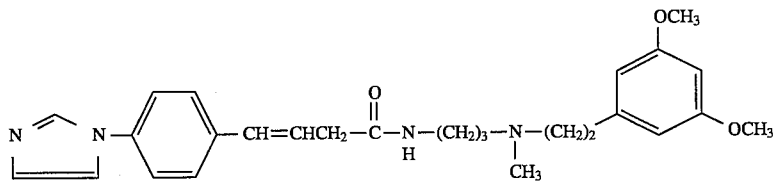

(E)-N-[3-((N'-(2-(3,4-Dimethoxyphenyl)ethyl)-N'-methyl)amino)butyl]-4-(4-(1H-imidazol-1-yl)phenyl)-3-butenamide

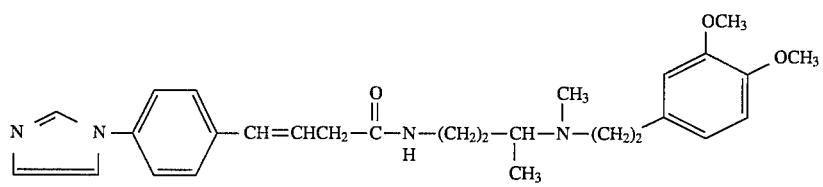

(E)-N-[3-((N'-(2-(3,4,5-Trimethoxyphenyl)ethyl)-N'-methyl)amino)propyl]-4-(4-(1H-imidazol-1-yl)phenyl)-3-butenamide

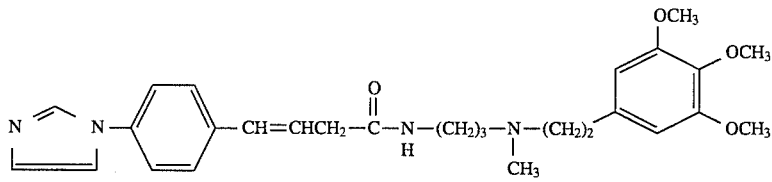

(E)-N-[3-((N'-(2-(3,4-Dimethoxyphenyl)ethyl)-N'-methyl)amino)propyl]-4-(4-(3-pyridyl)phenyl)-3-butenamide

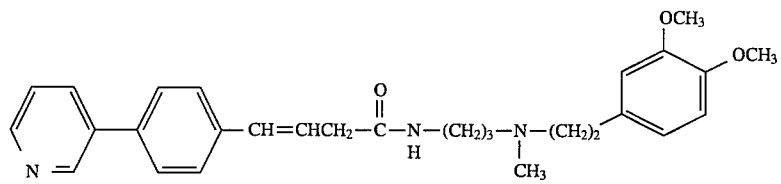

(E)-N-[3-((N'-(2-(3,4-Dimethoxyphenyl)ethyl)-N'-methyl)amino)propyl]-4-(4-(4-pyridyl)phenyl)-3-butenamide

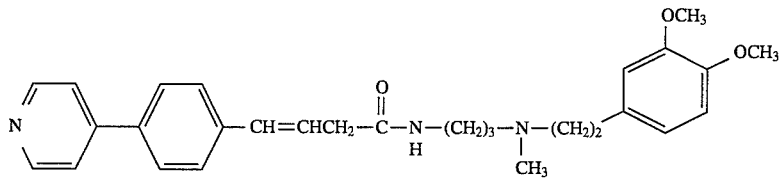

(E)-N-[3-((N'-(2-(3,4-Dimethoxyphenyl)ethyl)-N'-methyl)amino)propyl]-4-(4-(1H-pyrrol-1-yl)phenyl)-3-butenamide

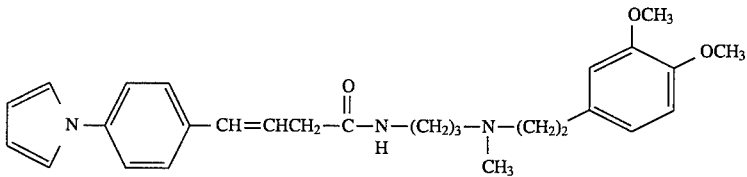

(E)-N-[3-((N'-(2-(3,4-Dimethoxyphenyl)ethyl)-N'-methyl)amino)propyl]-4-(4-(1H-1,2,4-triazol-1-yl)phenyl)-3-butenamide

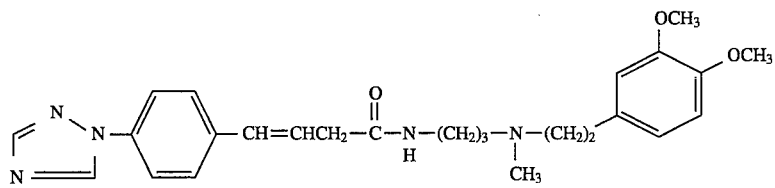

(E)-N-[3-((N'-(2-(3,4-Dimethoxyphenyl)ethyl)-N'-methyl)amino)propyl]-4-(4-(1H-pyrazol-1-yl)phenyl)-3-butenamide

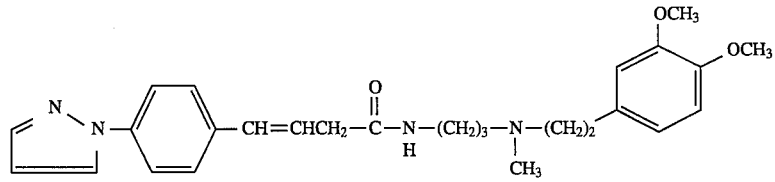

(E)-N-[3-((N'-(2-(3,4-Dimethoxyphenyl)ethyl)-N'-methyl)amino)propyl]-4-(4-(1,3-oxazol-5-yl)phenyl)-3-butenamide

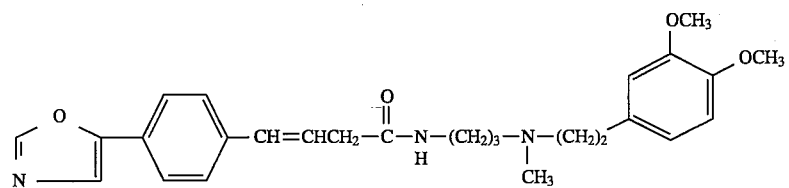

(E)-N-[3-((N'-(2-(3,4-Dimethoxyphenyl)ethyl)-N'-methyl)amino)propyl]-4-(4-(4(1H)-pyridon-1-yl)phenyl)-3-butenamide

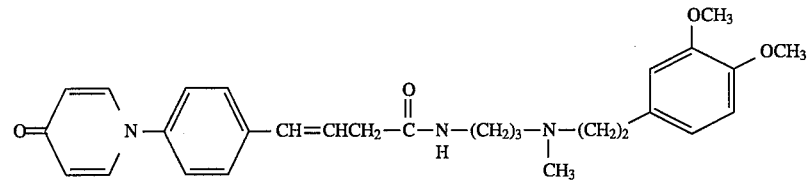

Representative processes for the preparation of the compounds of the present invention will now be described.

Preparation Process

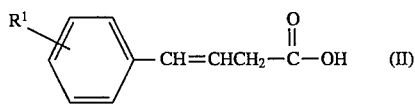

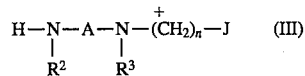

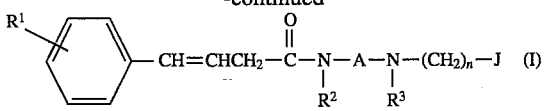

wherein $R^1$, $R^2$, $R^3$, n, A and J are each as defined above.

Namely, the objective compound (I) can be prepared by reacting a carboxylic acid represented by the general formula (II) or a reactive derivative thereof with an amine compound represented by the general formula (III) to carry out amidation.

The reactive derivative of the compound (II) includes acyl halides such as acyl chloride and acyl bromide; acid azides; reactive esters thereof with N-hydroxybenzotriazole or N-hydroxysuccinimide; symmetric acid anhydrides and mixed acid anhydrides thereof with alkylcarbonic acid or p-toluenesulfonic acid.

When a compound (II) is used as a free acid, it is preferable to carry out the above reaction in the presence of a condensing agent under cooling with ice or under reflux by heating. Examples of the condensing agent include dicyctohexylcarbodiimide, 1,1'-carbonyldiimidazole, ethyl chloroformate, diethyl azodicarboxylate and dipyridyl disulfide.

The reaction may be carried out in water or an inert organic solvent by using a compound (II) or a reactive derivative thereof and a compound (III) in molar amounts which are nearly equal to each other or one of which is slightly larger than the other. Examples of the inert organic solvent include methanol, ethanol, pyridine, tetrahydrofuran, dioxane, ether, benzene, toluene, xylene, methylene chloride, dichloroethane, chloroform, dimethylformamide, ethyl acetate and acetonitrile.

Depending upon the kind of the reactive derivative, it is advantageous from the standpoint of the smoothness of the reaction to use a base such as diisopropylethylamine, triethylamine, pyridine, picoline, lutidine, N,N-dimethylaniline, 4-dimethylaminopyridine, potassium carbonate or sodium hydroxide.

The reaction temperature is not particularly limited but varies depending upon the kind of the reactive derivative. Generally, the reaction is carried out at a temperature of from $-20°$ C. to reflux temperature to obtain the objective compound.

The compound represented by the general formula (II) to be used as a starting material in the present invention can be prepared by, for example, the following process:

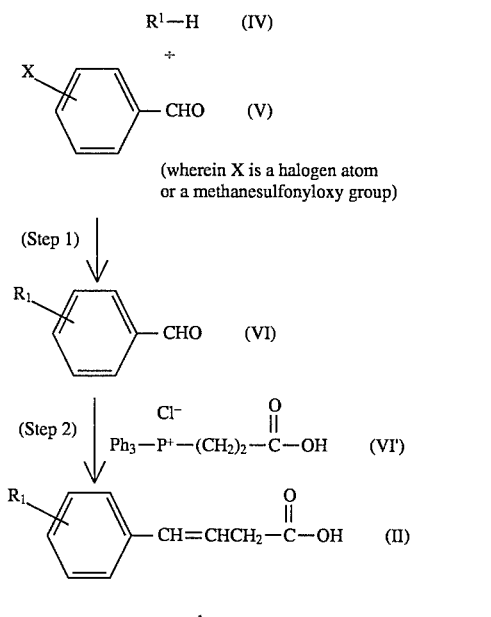

(In the above formulas, $R^1$ is as defined above and Ph is a phenyl group)

(Step 1)

In this step, a compound represented by the general formula (V) is reacted with a compound represented by the general formula (IV) in the presence of a copper catalyst such as copper powder or copper oxide under heating to carry out an Ullmann reaction. Thus, a compound (VI) is obtained. This reaction may be carried out in the absence of any solvent or in the presence of an inert organic solvent such as nitrobenzene, dimethylformamide or pyridine, or water.

Alternatively, a compound represented by the general formula (VI) may be prepared by reacting a compound represented by the general formula (V) with a salt of a compound represented by the general formula (IV) with a metal such as lithium, sodium or potassium and subjecting the obtained intermediate to a replacement reaction or the like.

This reaction may be carried out in the absence of any solvent or in the presence of an inert organic solvent such as dimethylformamide, dimethylacetamide, dimethyl sulfoxide, dioxane, ether or tetrahydrofuran.

(Step 2)

A compound represented by the general formula (VI) is reacted with a compound represented by the general formula (VI') in the presence of potassium t-butoxide, caustic potash, caustic soda, sodium methoxide, sodium ethoxide or sodium hydride in a suitable solvent at a temperature of $-78°$ C. to a room temperature according to an ordinary process to obtain a compound (II). Examples of the solvent include ether, tetrahydrofuran, dioxane, dimethylformamide, dimethylacetamide and dimethyl sulfoxide.

Further, a compound represented by the general formula (VI) may be also prepared by the following process:

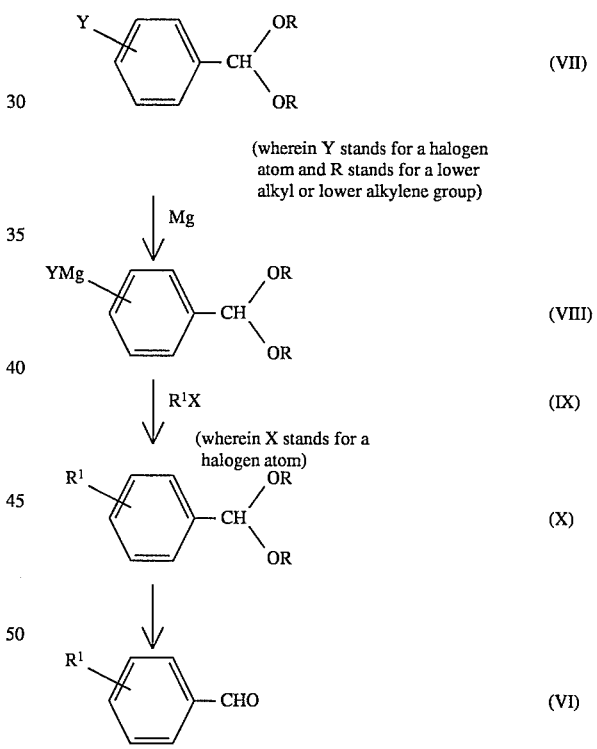

(in the above formulas, $R^1$ is as defined above)

Namely, a compound represented by the general formula (VII) is reacted with metallic magnesium under heating in a solvent such as ether or tetrahydrofuran, if necessary, in the presence of an iodine as a catalyst to obtain a Grignard reagent (VIII). This Grignard reagent is reacted with a halide represented by the formula (IX) in the presence of a metal complex catalyst at a room or elevated temperature or under reflux by heating according to an ordinary process to obtain a compound represented by the general formula (X). Examples of the catalyst include bis(1,3-diphenylphosphinopropane)nickel (II) chloride and tetrakis(triphenylphosphine)palladium. The compound represented by the general formula (X) is deacetalized with an acid to obtain a compound (VI).

The compound (III) to be used as the other starting material can be prepared by, for example, the following processes:

(Preparation Process 1)

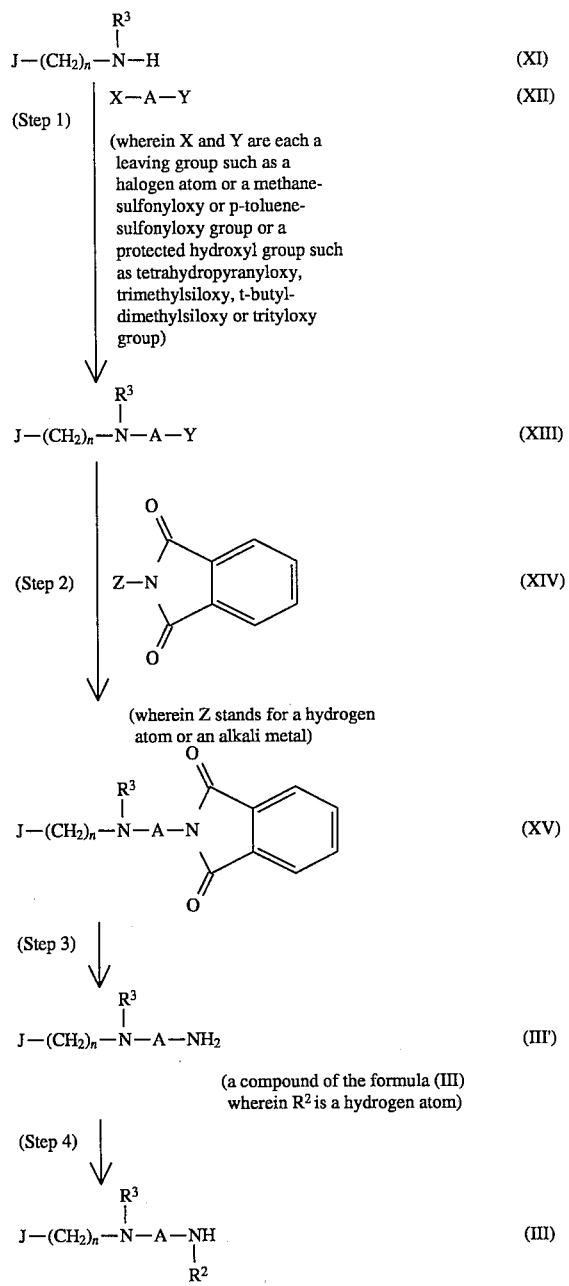

(in the above formulas, $R^2$, $R^3$, n, A and J are each as defined above)

(Step 1)

In this step, a compound represented by the formula (XI) is reacted with a compound represented by the formula (XII) according to an ordinary process to obtain a compound (XIII).

More specifically, the above reaction is carried out in a suitable solvent in the presence of a base such as potassium carbonate, sodium carbonate, triethylamine or diisopropylethylamine under heating to obtain a compound (XIII). Examples of the solvent include benzene, toluene, xylene, dimethylformamide, acetonitrile, dimethyl sulfoxide, dioxane and tetrahydrofuran.

(Step 2)

When Y is a leaving group such as a halogen atom or a methanesulfonyloxy group, the compound (XIII) is reacted with an alkali metal salt of phthalimide (XIV) such as potassium or sodium salt thereof in the presence of a base such as potassium carbonate or sodium carbonate to obtain a compound (XV). On the other hand, when Y is a protected hydroxyl group such as a trityloxy or t-butyldimethylsiloxy group, the compound (XIII) is freed of the protective group according to an ordinary method and subjected to the Mitsunobu reaction with phthalimide, triphenylphosphine or diethyl azodicarboxylate to obtain a compound (XV). In this case, it is preferable to use an inert solvent such as diethyl sulfoxide, dimethylformamide, dimethylacetamide, acetonitrile or tetrahydrofuran.

(Step 3)

A compound represented by formula (XV) is reacted with, for example, hydrazine monohydrate in an organic solvent such as methanol or ethanol under reflux to obtain a compound (III') (corresponding to a compound of formula (III) wherein $R^2$ is a hydrogen atom).

(Step 4)

A compound represented by formula (III') (corresponding to a compound of formula (III) wherein $R^2$ is a hydrogen atom) is reacted with an aldehyde or ketone in the presence of a catalyst such as palladium/carbon, platinum oxide or Raney nickel in a hydrogen atmosphere to carry out reductive amination. Thus, a compound represented by formula (III) is obtained.

The aldehyde and ketone to be used in this step include acetone, cyclobutanone, cyclopentanone and benzaldehyde. A solvent may be used in this step and examples thereof include methanol, ethanol, benzene, toluene, xylene, dimethylformamide, tetrahydrofuran, dioxane and ethyl acetate.

Alternatively, a compound represented by formula (III) can be prepared by converting a compound represented by formula (III') into an amide or carbamate thereof, for example, N-formyl, N-acetyl, N-methoxycarbonyl or N-ethoxycarbonyl derivative according to an ordinary process and reducing the obtained amide or carbamate in the presence of a metal hydride complex such as lithium aluminum hydride or boran.

This reduction may be carried out in a solvent at a room or elevated temperature or under reflux by heating and examples of the solvent include ether, tetrahydrofuran, dioxane, 1,2-dimethoxyethane and diethylene glycol dimethyl ether.

Further, a compound (XV) can be also prepared by the following process:

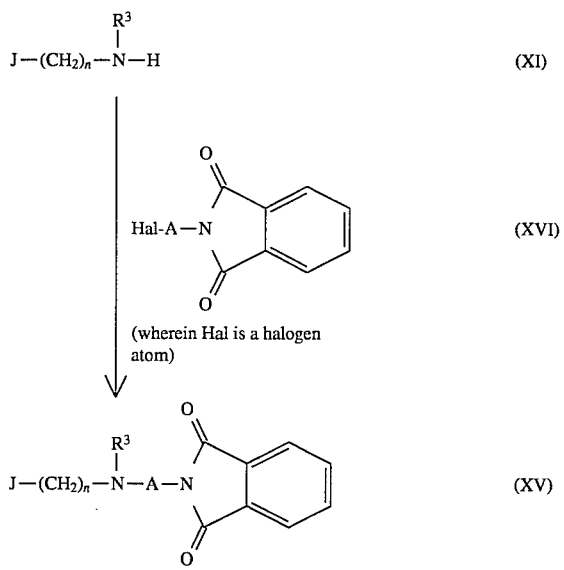

Namely, a compound represented by formula (XI) is reacted with a compound (XVI) in the presence of a base such as potassium carbonate, sodium carbonate, caustic soda, triethylamine or diisopropylethylamine at a room or elevated temperature or under reflux by heating to obtain a compound (XV).

A suitable solvent may be used in this step and examples thereof include dimethyl sulfoxide, dimethylformamide, dimethylacetamide and acetonitrile.

(Preparation Process 2)

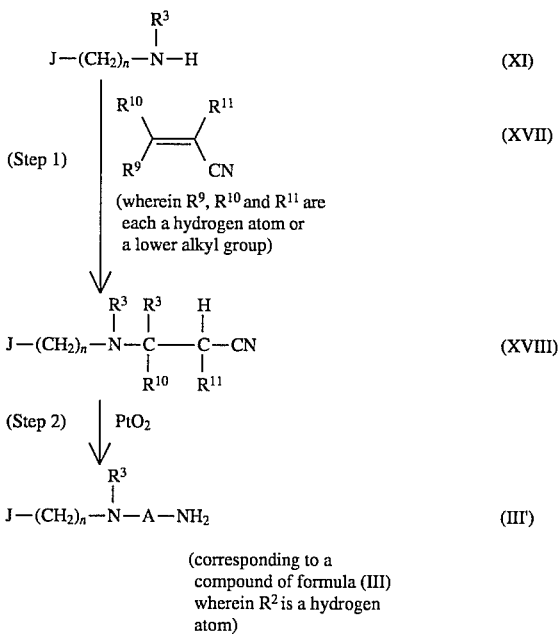

(Step 1)

A compound represented by formula (XI) is reacted with a compound represented by formula (XVII) in the absence of any solvent or in the presence of a solvent such as dichloromethane, chloroform, acetonitrile, dimethylformamide, dimethyl sulfoxide, ether, tetrahydrofuran, methanol or ethanol under heating or reflux to obtain a compound (XVIII).

(Step 2)

A compound represented by formula (XVIII) is hydrogenated in the presence of a catalyst such as palladium/carbon, platinum oxide or Raney nickel to obtain a compound represented by the formula (III').

The hydrogenation is carried out in a solvent such as methanol, ethanol, dimethylformamide or ethyl acetate under an ordinary or elevated pressure at an ordinary or elevated temperature.

(Preparation Process 3)

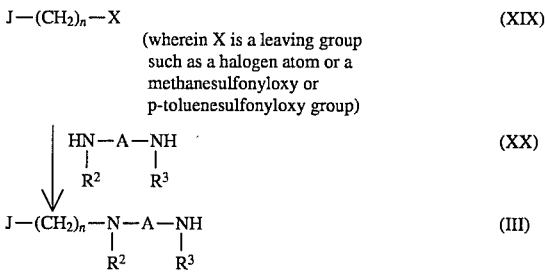

The invention further provides the pharmacological use of the compounds of the invention. A pharmacological composition of the invention comprises a pharmacologically effective amount of the butenoic or propenoic acid derivative as defined by the formula II and a pharmacologically acceptable carrier. Further here is provides a method for treating, preventing, remitting or ameliorating ischemic heart diseases by administering the butenoic or protenoic acid derivative having the formula II in a pharmacologically effective amount to a human being. The comound of the invention provides, in particular, an excellent coronary vasodilating and heart rate lowering effect.

Accordingly, the compound of the present invention is effective for the treatment, prevention, remission or amelioration of ischemic heart diseases such as coronary sclerosis, various angina pectoris or cardiac infarction.

When the compound of the present invention is to be used as a drug, it may be administered either orally or parenterally. The dose varies depending upon the degree of symptoms; the age, sex, weight and sensitivity of a patient; the method, timing and interval of administration; the properties, preparation method and kind of a drug or the kind of an active ingredient and therefore is not particularly limited. Generally, the dose is about 1 to 1000 mg, preferably about 5 to 500 mg, still preferably about 50 to 200 mg. It is generally administered at once or in 2 to 4 portions.

A solid drug containing the compound of the present invention for oral administration may be prepared by mixing a compound of the present invention with a filler and, if necessary, binder, disintegrator, lubricant, coloring agent or corrigent and shaping the obtained mixture into tablet, coated tablet, granule, powder or capsule.

Examples of the filler include lactose, corn starch, sucrose, glucose, sorbitol, crystalline cellulose and silicon dioxide. Examples of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin. Examples of the lubricant include magnesium stearate, talc, polyethylene glycol, silica and hardened vegetable oils. The coloring agent may be any one permitted to be added to a drug. The corrigent includes cacao powder, mentha herb, aromatic powder, mentha oil, borneol and powdered cinnamon bark. Of course, the tablet or granule may be coated with sugar, gelatin or the like.

An injection containing the compound of the present invention can be prepared by mixing a compound of the present invention as a principal agent with pH adjustor, buffer, suspending agent, solubilizing agent, stabilizer, tonicity agent or preservative and treating the obtained mixture by an ordinary process to obtain an intravenous, subcutaneous or intramuscular injection. If necessary, the injection may be freeze-dried by an ordinary method.

Examples of the suspending agent include methylcellulose, Polysorbate 80, hydroxyethylcellulose, acacia, tragacanth powder, sodium carboxymethylcellulose and polyoxyethylene sorbitan monolaurate.

Examples of the solubilizing agent include polyoxyethylene hardened castor oil, Polysorbate 80, nicotinamide, polyoxymethylene sorbitan monolaurate, macrogol and ethyl ester of castor oil fatty acid.

Examples of the stabilizer include sodium sulfite, sodium metasulfite and ether, while those of the preservative include methyl p-hydroxybenzoate, ethyl p-hydroxybenzoate, sorbic acid, phenol, cresol and chlorocresol.

A compound represented by the formula (XIX) is reacted with a compound (XX) in the presence of a base such as potassium carbonate, sodium carbonate, caustic soda, triethylamine or diisopropylethylamine at a room or enhanced temperature or under reflux to obtain a compound (III).

A suitable solvent may be used in this process and examples of the solvent include dimethyl sulfoxide, dimethylformamide, dimethylacetamide and acetonitrile.

EMBODIMENT (II)

In the embodiment (II), it is preferable that G is the phenyl having R15 and R16, R15 and R16 each are hydrogen, a halogen, cyano, a lower alkoxy, —NR7R8, R7 and R8 each being hydrogen or a lower alkyl, an alkylthio or an alkanoylamino, or R15 and R16 may form a cyclic ring together with oxygen and the two adjacent carbon atoms, R11 and R12 each are hydrogen, m is zero or 1, X is oxygen, R2 is hydrogen or may form a cyclic ring together with R12, A is an alkylene having 1 to 3 carbon atoms, R3 is a lower alkyl, n is an integer of 1 to 3, J is the phenyl having R4, R5 and R6, R4, R5 and R6 each are hydrogen or a lower alkyl.

It is also preferable that J is m-dimethoxy-phenyl or m,p-dimethoxy-phenyl.

When R2 or R3 forms a heterocyclic ring with A, the following two are preferable:

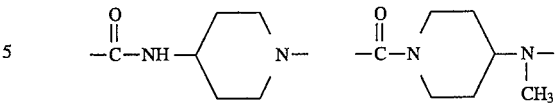

Also in the embodiments (II), preferable groups for the lower alkyl, the lower alkoxy and the cycloalkyl are defined in the same way as shown in the emobodiments (I).

It is more preferable that R15 and R16 are a halogen such as fluorine, cyano, a lower alkoxy such as methoxy and ethoxy, a mono- or di-lower alkylamino such as dimethylamino, an alkylthio such as methylthio, an alkanoylamino such as CH3CONH— and methylenedioxy.

It is preferable that R11 and R12 are hydrogen at the same time.

Preferable groups of —NR2—A—NR3— are defined in the same way as shown in the embodiment (I).

Most preferable compounds are:

(E)-N-(3-((N'-(2-(3,4-dimethoxyphenyl)ethyl)-N'-methyl)-amino)propyl)-4-(4-fluorophenyl)-3-buteneamide,
(E)-N-(3-((N'-(2-(3,4-dimethoxyphenyl)ethyl)-N'-methyl)amino)propyl)-3-(4-fluorophenyl)propeneamide,
(E)-N-(3-((N'-(2-(3,4-dimethoxyphenyl)ethyl)-N'-methyl)amino)propyl)-3-(4-cyanophenyl)propeneamide,
(E)-N-(3-((N'-(2-(3,4-dimethoxyphenyl)ethyl)-N'-methyl)amino)propyl)-4-(3,4-(methylenedioxy)phenyl)-3-buteneamide,
(E)-N-(3-((N'-(2-(3,4-dimethoxyphenyl)ethyl)-N'-methyl)amino)propyl)-4-(4-cyanophenyl)-3-buteneamide,
(E)-N-(3-((N'-(2-(3,4-dimethoxyphenyl)ethyl)-N'-methyl)amino)propyl)-4-(3,4-dimethoxyphenyl)-3-buteneamide,
(E)-N-(3-((N'-(2-(3,4-dimethoxyphenyl)ethyl)-N'-methyl)amino)propyl)-4-(4-(dimethylamino)phenyl)-3-buteneamide,
(E)-N-(3-((N'-(2-(3,4-dimethoxyphenyl)ethyl)-N'-methyl)amino)propyl)-4-(4-(methylthio)phenyl)-3-buteneamide,
(E)-N-(3-((N'-(2-(3,4-dimethoxyphenyl)ethyl)-N'-methyl)amino)propyl)-4-(4-chlorophenyl)-3-buteneamide,
(E)-N-(3-((N'-(2-(3,4-dimethoxyphenyl)ethyl)-N'-methyl)amino)propyl)-4-(4-methoxyphenyl)-3-buteneamide,
(E)-N-(3-((N'-(2-(3,4-dimethoxyphenyl)ethyl)-N'-methyl)amino)propyl)-4-(4-(acetylamino)phenyl)-3-buteneamide,
(E)-N-(3-((N'-(2-(3,4-dimethoxyphenyl)ethyl)-N'-methyl)amino)propyl)-3-(4-fluorobenzylidene)-2-pyrrolidinone and
(E)-N-(3-((N'-(2-(3,4-dimethoxyphenyl)ethyl)-N'-methyl)amino)propyl)-3-(4-cyanobenzylidene)-2-pyrrolidinone.

The above shown compounds are defined by the following formulae, respectively.

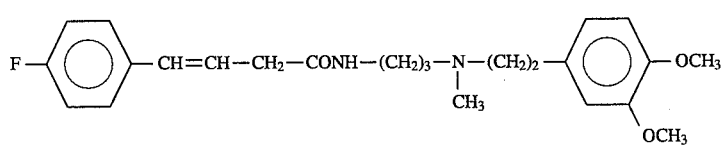

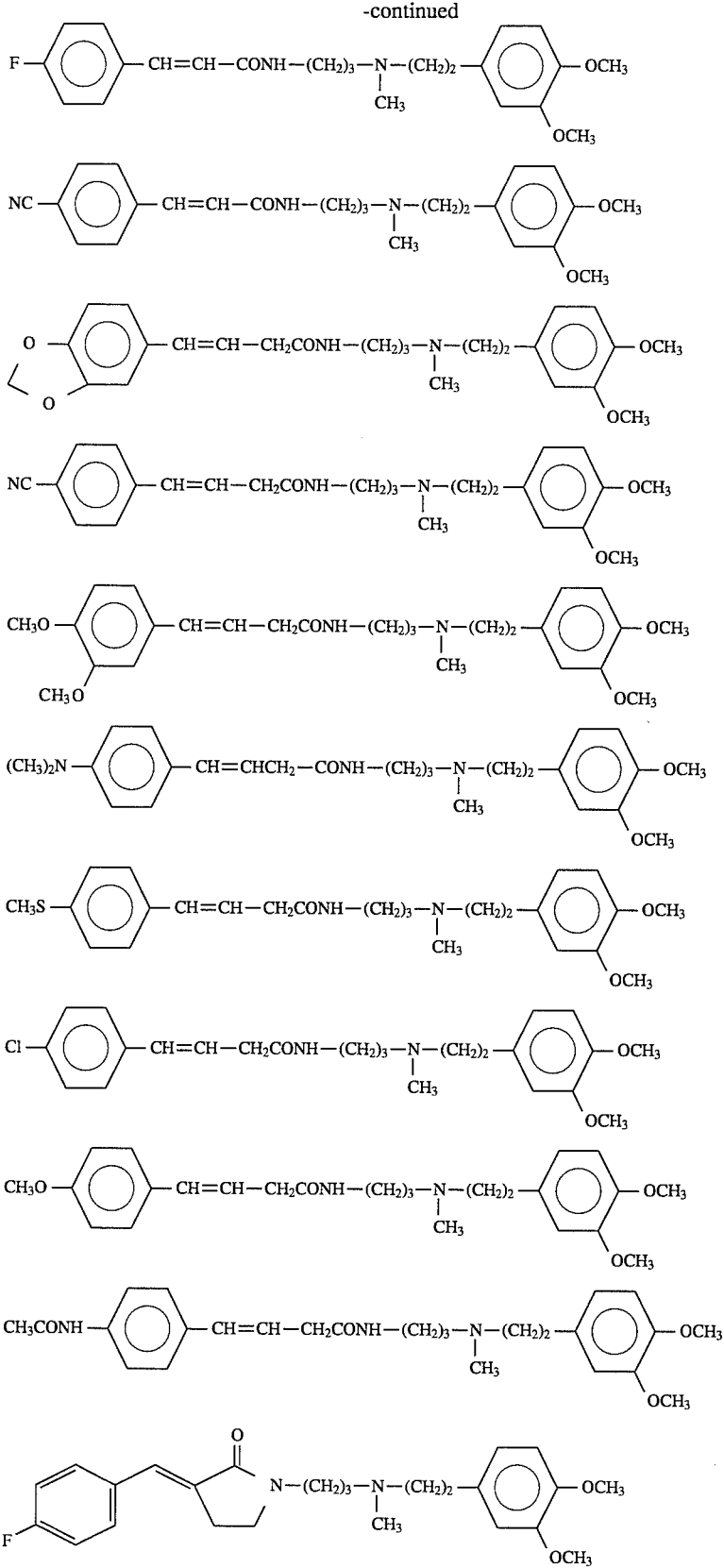

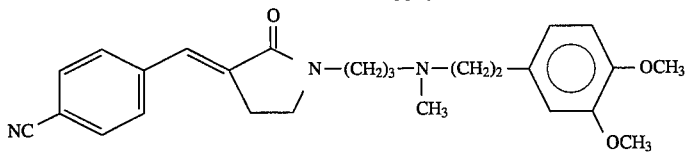

Typical preparation methods for the compounds according to the present invention are explained below.

Preparation Method

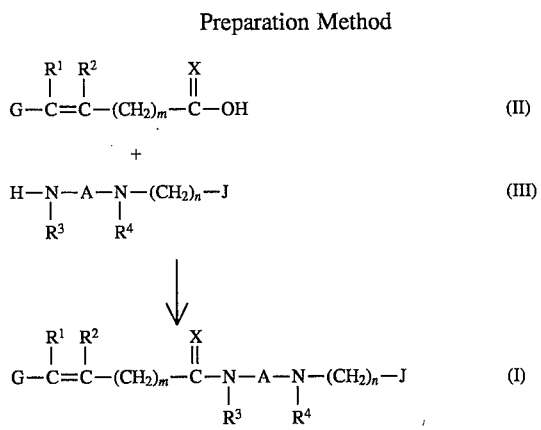

where $R^1$, $R^2$, $R^3$, $R^4$, X, m, n, G, A and J in each of the formulae have the same meanings as described above.

That is, the aimed compound (I) can be obtained by amidizing a carboxylic acid or thiocarboxylic acid represented by the general formula (II) or the reactive derivative thereof with an amino compound represented by the general formula (III).

As the reactive derivative of the compound (II), there can be mentioned active esters with acid halide such as acid chloride on acid bromide, acid azide, N-hydroxybenzotriazole or n-hydroxysuccinic imide, mixed acid anhydride with symmetric acid anhydride, alkyl carbonic acid, p-toluene sulfonic acid or phosphoric acid ester, etc.

When free carboxylic acid is used as the compound (II), it is preferred to react under the presence of a condensating agent such as dicyclohexyl carbodiimide, 1,1'-carbonyl dimidazole, chloroformate, diethyl azodicarboxylate, dipyridyldisulfide, etc. under ice cooling or heat-refluxing.

The reaction was carried out by using a compound (II) or the reactive derivative thereof and a compound (III) substantially in an equi-molar ratio or at a slight excess molar ratio of one of them, in a solvent such as water or an organic solvent inert to the reaction, for example, methanol, ethanol, pyridine, tetrahydrofuran, dioxane, ether, benzene, toluene, xylene, methylene chloride, dichloroethane, chloroform, dimethylformamide, methylene chloride, ethyl acetate and acetonitrile.

Depending on the kind of the reactive derivative, it may be some time advantageous to add a base such as diisopropyl ethylamine, triethylamine, pyridine, picoline, lutidine, N,N-dimethylanillne, 4-dimethylaminopyridine, potassium carbonate or sodium hydroxide upon reaction in view of smooth proceeding of the reaction.

The reaction temperature varies depending on the kind of the reactive derivative and has no particular restriction, and the aimed compound can usually be obtained by reaction at a temperature from −20° C. to heat-refluxing temperature.

Further, the compound (I) can also be prepared by the following method.

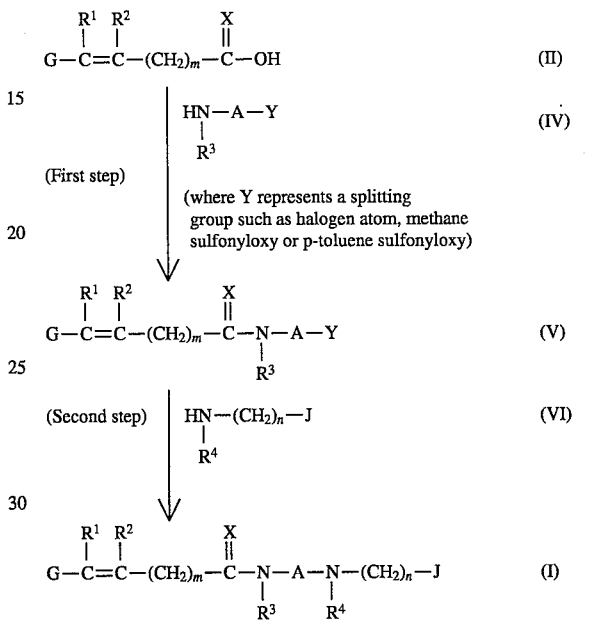

where $R^1$, $R^2$, $R^3$, $R^4$, X, m, n, G, A and J in each of the formulae have the same meanings as described above.

(First Step)

In this the step, the compound (V) is formed by amidizing a carboxylic acid or thiocarboxylic acid represented by the general formula (II) or the reactive derivative thereof by the reaction with an amino compound represented by the general formula (IV).

As the reactive derivative of the compound (II), there can be mentioned active esters with acid halide such as acid chloride or acid bromide, acid azide, N-hydroxybenzotriazole or n-hydroxysuccin imide, mixed acid anhydride with symmetric acid anhydride, alkyl carbonic acid, p-toluene sulfonic acid or phosphoric acid ester, etc.

When free carboxylic acid is used as the compound (II), it is preferred to react under the presence of a condensating agent such as dicyclohexyl corbodiimide, 1,1'-carbonyl diimidazole, chloroformate, diethyl azodicarboxylate, dipyridyldisulfide, etc. under ice cooling or heat refluxing.

The reaction was carried out by using a compound (II) or the reactive derivative thereof and a compound (III) substantially in an equi-molar ratio or at a slight excess molar ratio of one of them, in a solvent such as water or an organic solvent inert to the reaction, for example, methanol, ethanol, pyridine, tetrahydrofuran, dioxane, ether, benzene, toluene, xylene, methylene chloride, dichloroethane, chloroform, dimethylformamide, methylene chloride, ethyl acetate and acetonitrile.

Depending on the kind of the reactive derivative, it may be some time advantageous to add a base such as diisopropyl ethylamine, triethylamine, pyridine, picoline, lutidine, N,N-dimethylaniline, 4-dimethylaminopyridine, potassium carbonate or sodium hydroxide upon reaction, in view of smooth proceeding of the reaction.

The reaction temperature varies depending on the kind of the reactive derivative and has no particular restriction, and the aimed compound can usually be obtained by reaction at a temperature from −20° C. to heat-reflux temperature.

(Second Step)

In this step, the aimed compound (I) is formed by reacting a compound represented by the general formula (V) with a compound represented by the general formula (VI) by a customary method.

That is, the compound (I) is formed by reacting a compound represented by the formula (V) with a compound (VI) at a temperature from a room temperature to a refluxing temperature under the presence of a base such as potassium carbonate, sodium carbonate, triethylamine and diisopropyl ethylamine.

In this case, solvent such as benzene, toluene, xylene, dimethylsulfoxide, dimethylformamide, dimethylacetoamide and acetonitrile can be used.

The compound (V) can also be formed by the following method.

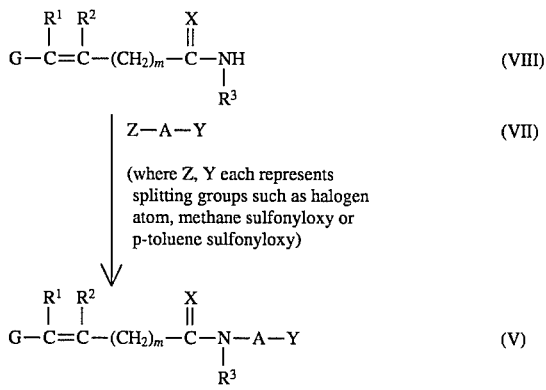

where $R^1$, $R^2$, $R^3$, $R^4$, X, m, n, G, A and J in each of the formulae have the same meanings as described above providing that $R^3$ is not H.

That is, the compound (V) can be formed by reacting a compound represented by the general formula (VIII) and a compound represented by the general formula (VII) by a customary method at a temperature from an ice cooled temperature to a heat refluxing temperature by using a solvent, for example, ether, tetrahydrofuran, dioxane, dimethylformamide, dimethylacetoamide and dimethylsulfoxide, under the presence of potassium tert-butoxide, sodium methoxide, sodium ethoxide, sodium amide, sodium hydride and potassium hydride.

Among the compounds represented by the general formula (II) used as the starting material in the present invention, those compounds in wich $R^1=R^2=H$, m=1, X=0 can be formed, for example, by the following method.

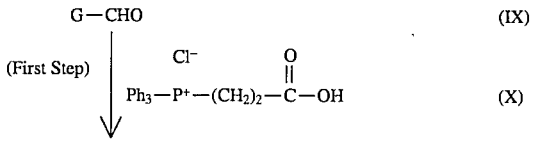

where G has the same meanings as described above and Ph represents phenyl group in each of the formulae.

(First Step)

The compound (II') can be formed by reacting a compound represented by the general formula (IX) and a compound represented by the general formula (X) by a customary method at a temperature from −78° C. to a room temperature by using a solvent, for example, ether, tetrahydrofuran, dioxane, dimethylformamide, dimethylacetoamide or dimethylsulfoxide and under the presence of potassium t-butoxide, potassium hydroxide, sodium hydroxide, sodium methoxide, sodium ethoxide or sodium hydride.

Further, the compound (III) as the starting material can be prepared, for example, by the following preparation method.

(Preparation Method 1)

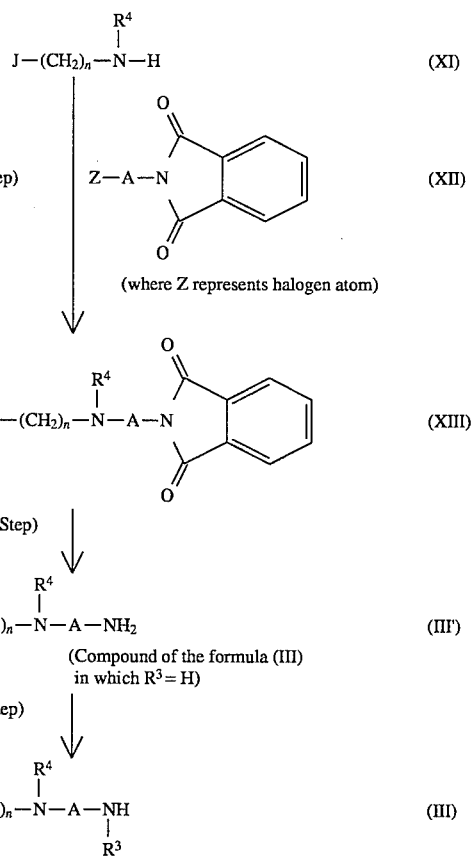

where $R^3$, $R^4$, n, A and J in each of the formulae have the same meanings as described above.

(First Step)

In this step, the compound (XIII) is formed by reacting a compound represented by the formula (XI) and a compound represented by the formula (XII) by a customary method.

Specifically, the compound (XIII) is formed by reacting both of the compounds at a temperature from a room temperature to a heat refluxing temperature by using a solvent, for example, benzene, toluene, xylene, dimethylformamide, acetonitrile, dimethylsulfoxide, dioxane and tetrahydrofuran and under the presence of a base, for example, potassium carbonate, sodium carbonate, triethylamine and diisopropylethylamine.

(Second Step)

A compound (III'), where $R^3$=H in the formula (III), can be formed by reacting a compound represented by the formula (XIII), for example, with a hydrazine monohydrate under heat reflux in the presence of an organic solvent such as methanol or ethanol.

(Third Step)

A compound represented by the formula (III) can be formed by conducting amidizing reduction between a compound represented by the formula (III'), in which $R^3$=H in the formula (III), and an aldehyde or ketone by using a catalyst such as palladium-carbon, platinum oxide, Raney nickel, etc. in a hydrogen atmosphere.

In this case, acetone, cyclobutanone, cyclopentanone or benzaldehyde can be used as the aldehyde or ketone. As the reaction solvent, there can be used methanol, ethanol, benzene, toluene, xylene, dimethylformamide, tetrahydrofuran, dioxane and ethyl acetate.

As an alternative method, a compound represented by the formula (III) can be formed by converting a compound represented by the formula (III') into an acidamide or carbamate, for example, N-formyl, N-acetyl, N-methoxycarbonyl or N-ethoxycarbonyl by a customary method, which is then reduced with a metal hydrogen complex compound, for example, aluminum lithium hydride or borane.

The reductive reaction is conducted at a temperature from a room temperature to a heat refluxing temperature by using a solvent such as ether, tetrahydrofuran, dioxane, 1,2-dimethoxyethane, diethylene glycol dimethyl ether, etc.

(Preparation Method 2)

$$J-(CH_2)_n-\overset{R^4}{\underset{|}{N}}-H \quad (XI)$$

(First Step) ↓ Hal-A—CN (XIV)

$$J-(CH_2)_n-\overset{R^4}{\underset{|}{N}}-A-CN \quad (XV)$$

(Second step) ↓ PtO₂

$$J-(CH_2)_n-\overset{R^4}{\underset{|}{N}}-A-NH_2 \quad (III')$$

(compound in which $R^3$ = H in the formula (III), where $R^4$, n, A and J in each of the formulae have the same meanings as described above and Hal represents a halogen atom.

(First Step)

The compound (XV) can be prepared by reacting a compound represented by the formula (XI) and a compound represented by a formula (XIV) at a temperature from a room temperature to a heat refluxing temperature without using solvent or under the presence of a solvent such as dichloromethane, chloroform, acetonitrile, dimethylformaide, dimethylsulfoxide, ether, tetrahydrofuran, methanol, ethanol, etc.

(Second Step)

The compound represented by the formula (III') can be prepared by subjecting a compound represented by the formula (XV) to a hydrogenating reaction by using a catalyst such as palladium-carbon, platinum oxide or Raney nickel.

In this case, the reaction is conducted under the pressure from a normal pressure to an elevated pressure and at a temperature from a normal temperature to an elevated temperature while using a solvent, for example, methanol, ethanol, dimethylformamide and ethyl acetate.

(Preparation Method 3)

$$J-(CH_2)_n-Y \quad (XVI)$$

(where Y represents a splitting group such as a halogen atom, methane sulfonyloxy or p-toluene sulfonyloxy)

$$\overset{HN-A-NH}{\underset{R^4 \quad \quad R^3}{| \quad \quad |}} \quad (XVII)$$

↓

$$J-(CH_2)_n-\underset{R^4}{\underset{|}{N}}-A-\underset{R^3}{\underset{|}{NH}} \quad (III)$$

where $R^3$, $R^4$, n, A, J in each of the formulae have the same meanings as described above.

The compound (III) can be prepared by reacting a compound represented by the formula (XVI) with a compound (XVII) at a temperature from a room temperature to a heat refluxing temperature under the presence of a base such as potassium carbonate, sodium carbonate, sodium hydroxide, triethylamine and diisopropylethylamine.

As the reaction solvent used in this case, there can be used, for example, those solvents such as dimethylsulfoxide, dimetylformamide, dimethylacetoamide or acetonitrile.

EMBODIMENT (III)

This is defined with the above shown formula (III).

It is preferable that W is azomethyne or sulfur (—S—) and R2 is hydrogen.

The heterocyclic ring for R31 has the same preferable groups as shown for R1. In addition, there is included a heteroaryl having a nitrogen(s) such as pyridazinyl, pyrazinyl, 1,2-dihydro-2-oxopyridyl, an enantiomorphic isomer thereof, 2,3-dihydro-3-oxopyridazinyl and an enantiomorphic isomer thereof. A heterocyclic ring having nitrogen and sulfur includes thiazolyl, isothiazolyl.

A preferable ring formed from R3, N and —(CH2)n- includes:

A preferable ring formed from R3, A and N includes:

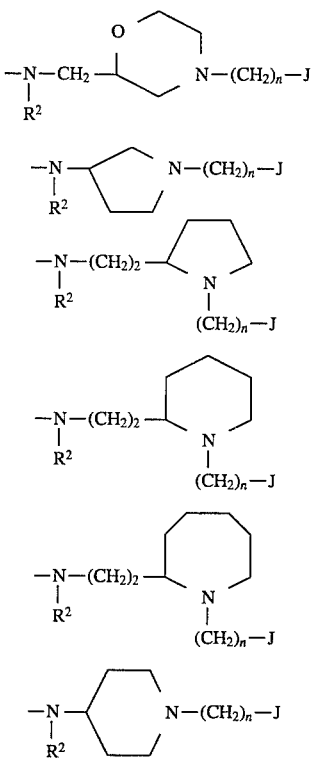

The lower alkyl, the lower alkoxy and the cycloalkyl are defined for their preferble groups in the same way as shown in the embodiment (I).

The ring formed from R2,, R3, N, A and N includes:

Preferable groups for R4,, R5 and R6 are defined in the same way as shown in the embodiment (I).

Most preferable compounds are:

(E)-N-(3-((N'-(2-(3,4-dimethoxyphenyl)ethyl)-N'-methyl)amino(propyl)-4-(4-(2-pyrazinyl)phenyl)-3-buteneamide, (E)-N-(3-((N'-(2-(3,4-dimethoxyphenyl)ethyl)-N'-methyl)amino)propyl)-4-(4-(1,3-thiazol-4-yl)phenyl)-3-buteneamide, (E)-N-(3-((N'-(2-(3,4-dimethoxyphenyl)ethyl)-N'-methyl)amino)propyl)-4-(4-(2-methyl-1,3-thiazol-4-yl)phenyl)-3-buteneamide, (E)-N-(3-((N'-(2-(3,4-dimethoxyphenyl)ethyl)-N'-methyl)amino)propyl)-4-(3-(1H-imidazol-1-yl)thiophene-5-yl)-3-buteneamide, (E)-N-(3-((N'-(2-(3,4-dimethoxyphenyl)ethyl)-N'-methyl)amino)propyl)-4-(2-(1H-imidazol-1-yl)thiophene-5-yl)-3-buteneamide, (E)-N-(N'-(2-(3,4-dimethoxyphenyl)ethyl)-3-pyrrolidinyl)-4-(4-(1H-imidazol-1-yl)phenyl)-3-buteneamide, (E)-N-(2-(N'-(2-(3,4-dimethoxyphenyl)ethyl)-2-pyrrolidinylethyl)-4-(4-(1H-imidazol-1-yl)phenyl)-3-buteneamide, (E)-N-(2-(N'-(2-(3,4-dimethoxyphenyl)ethyl)-2-pyperidinoethyl)-4-(4-(1H-imidazol-1-yl)phenyl)-3-buteneamide, (E)-N-(3-((N'-(2-(3,5-dimethoxyphenyl)ethyl)-N'-methyl)amino)-2-hydroxypropyl)-4-(4-(1H-imidazol-1-yl)phenyl)-3-buteneamide and (E)-N-(1-(2-(3,4-dimethoxyphenyl)ethyl)-4-piperidinyl)-4-(4-(1H-imidazol-1-yl)phenyl)-3-buteneamide.

The above listed compounds have the following formulae, respectively.

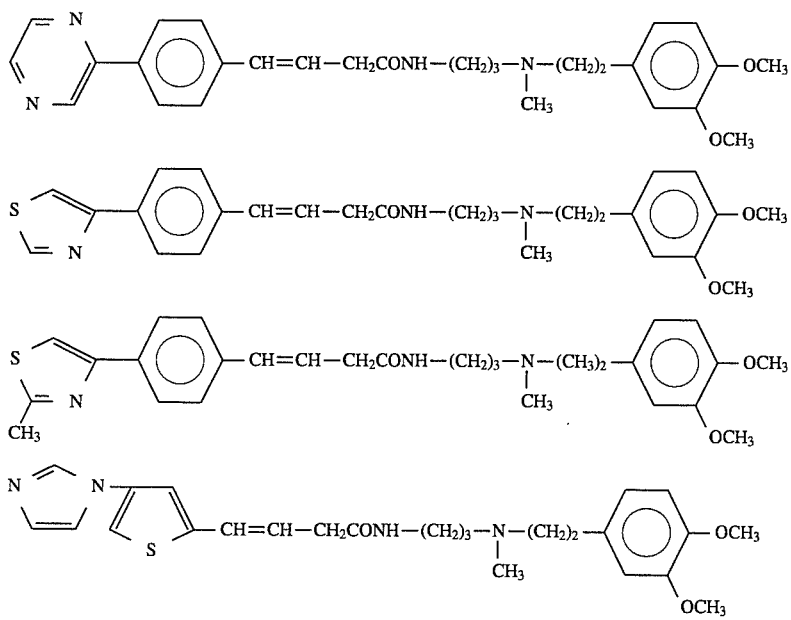

-continued

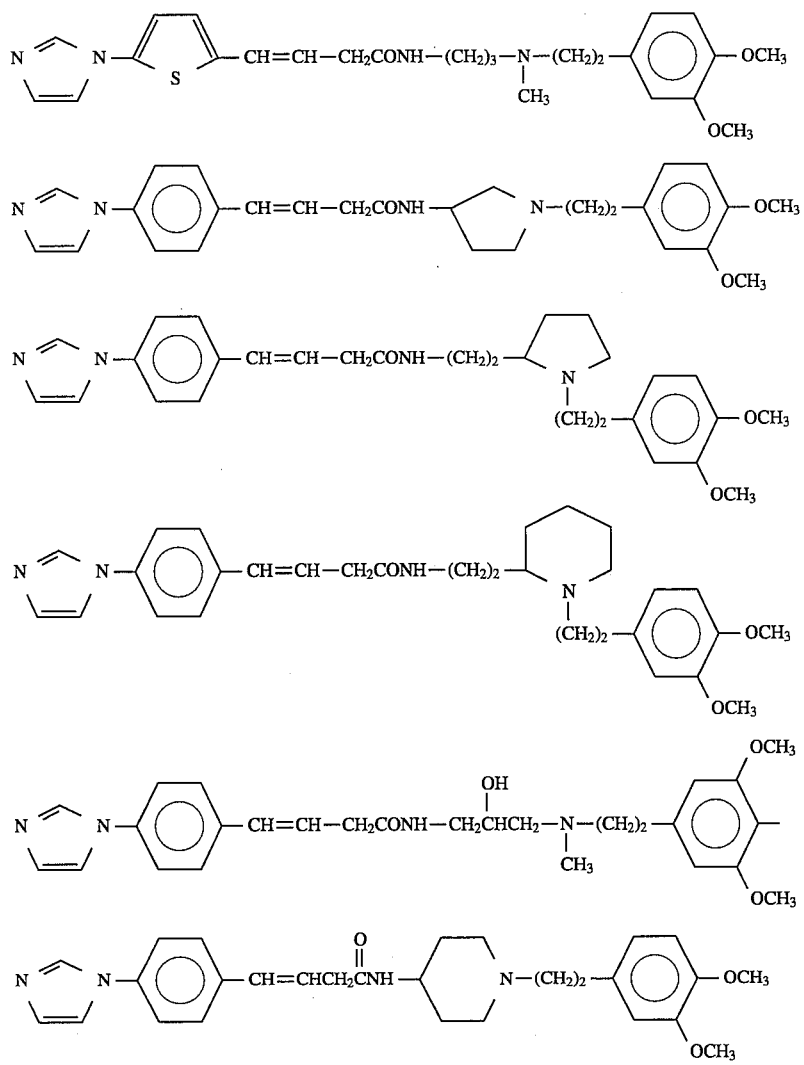

Preparation methods for the embodiments III are described below in reference to examples in which W is vinylene. The methods apply to the other groups than vinylene for W.

Preparation Method

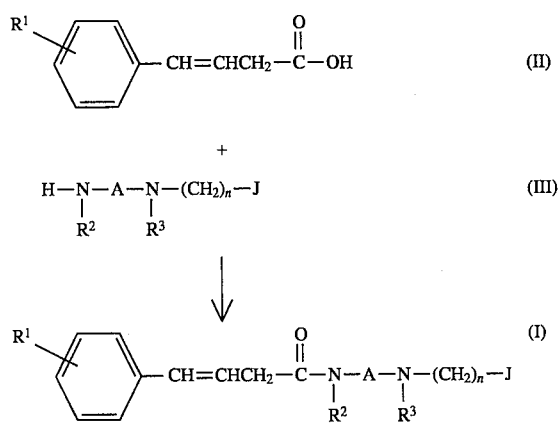

where $R^1$, $R^2$, $R^3$, n and J in each of the formulae have the same meanings as described above.

That is, the aimed compound (I) can be obtained by amidizing a carboxylic acid acid represented by the general formula (II) on the reactive derivative thereof with an amino compound represented by the general formula (III).

As the reactive derivative of the compound (II), there can be mentioned active esters with acid halide such as acid chloride or acid bromide, acid azide, N-hydroxybenzotriazole or n-hydroxysuccinic imide, mixed acid anhydride with symmetric acid anhydride, alkyl carbonic acid, p-toluene sulfonic acid or phosphoric acid ester, etc.

When free carboxylic acid is used as the compound (II), it is preferred to react under the presence of a condensating agent such as dicyclohexyl carbodiimide, 1,1'-carbonyl diimidazole, chloroformate, diethyl azodicarboxylate, dipyridyldisulfide, etc. under ice cooling or heat-refluxing.

The reaction was carried out by using a compound (II) or the reactive derivative thereof and a compound (III) substantially in an equi-molar ratio or at a slight excess molar ratio of one of them, in a solvent such as water or an organic solvent inert to the reaction, for example, methanol, ethanol, pyridine, tetrahydrofuran, dioxane, ether, benzene, toluene, xylene, methylene chloride, dichloroethane, chloroform, dimethylformamide, methylene chloride, ethyl acetate and acetonitrile.

Depending on the kind of the reactive derivative, it may be some time advantageous to add a base such as diisopropyl ethylamine, triethylamine, pyridine, picoline, lutidine, N,N-dimethylaniline, 4-dimethylaminopyridine, potassium carbonate or sodium hydroxide upon reaction in view of smooth proceeding of the reaction.

The reaction temperature varies depending on the kind of the reactive derivative and has no particular restriction, and the aimed compound can usually be obtained by reaction at a temperature from −20° C. to heat-refluxing temperature.

The compound represented by the general formula (II) used as the starting material in the present invention can be prepared, for example, by the following method.

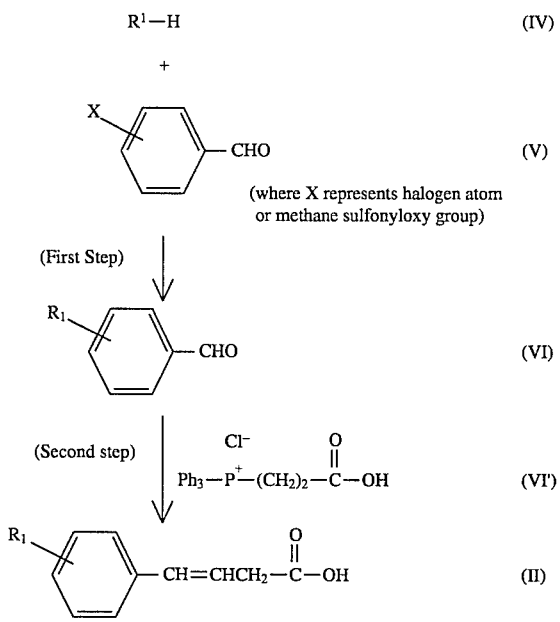

where $R^1$ in each of the formulae has the same meanings as described above and Ph represents phenyl group.

(First Step)

In this the step, the compound (VI) is formed by subjecting a compound represented by the general formula (V) and a compound represented by the general formula (IV) to Ullmann type reaction under heating using a copper catalyst such as copper powder or copper oxide.

In this case, the reaction can be carried out without solvent or by using those inert organic solvents not relevant to the reaction, for example nitrobenzene, dimethylformamide, pyridine or water.

As another method of forming the compound represented by the general formula (VI), there can be mentioned a method of reacting a compound represented by the general formula (V) with a compound represented by the general formula (IV) after being converted into a metal salt such as of lithium, sodium or potassium and then preparing the compound (VI) by substituting reaction, etc.

The reaction can be carried out without using solvent or by using those inert organic solvents not relevant to the reaction, for example, dimethylformamide, dimethylacetoamide, dimethylsulfoxide, dioxane, ether and tetrahydrofuran.

(Second Step)

The compound (II) can be formed by reacting a compound represented by the general formula (VI) and a compound represented by the general formula (VI') by a customary method at a temperature from −78° C. to a room temperature by using a solvent, for example, ether, tetrahydrofuran, dioxane, dimethylformamide, dimethylacetoamide and dimethylsulfoxide, under the presence of potassium tert-butoxide, sodium methoxide, sodium ethoxide, sodium amide, sodium hydride and potassium hydride.

Another method of forming the compound represented by the general formula (VI) is shown below:

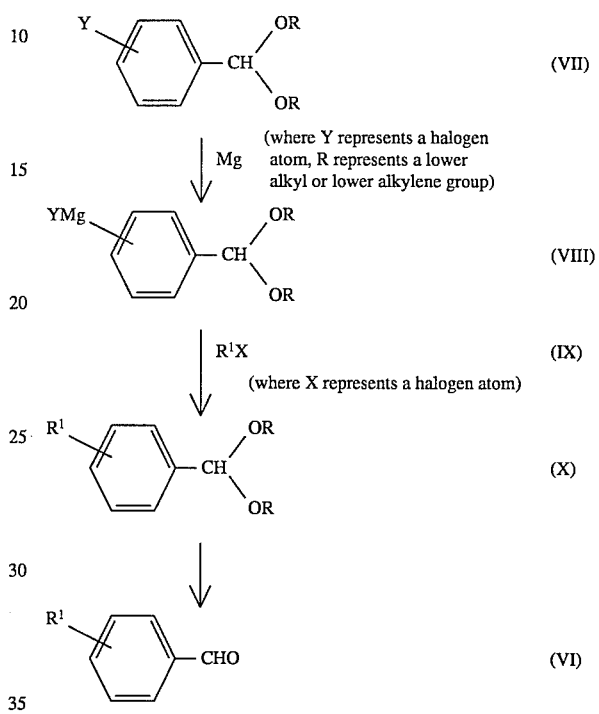

where $R^1$ has the same meanings as described above in each of the formulae.

That is, a compound represented by the general formula (VII) is heated together with metal magnesium under the presence of a solvent such as ether or tetrahydrofuran and with addition of iodine as a catalyst if required, to prepare a Grignard reagent (VIII). Then, it is reacted with a halide represented by the formula (IX) with addition of a metal complex as a catalyst, for example, bis(1,3-diphenylphosphinopropane) nickel (II) chloride or tetrakistriphenylphisphine palladium by a customary method at a temperature from a room temperature to a heat refluxing temperature to prepare a compound represented by the general formula (X). Then, the compound is deacetalized with an acid to obtain a compound represented by the general formula (VI).

Further, the compound (III) as the starting material can be prepared, for example, by the following preparation method.

(Preparation Method 1)

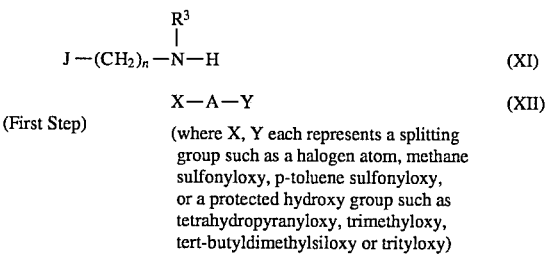

(First Step)

(where X, Y each represents a splitting group such as a halogen atom, methane sulfonyloxy, p-toluene sulfonyloxy, or a protected hydroxy group such as tetrahydropyranyloxy, trimethyloxy, tert-butyldimethylsiloxy or trityloxy)

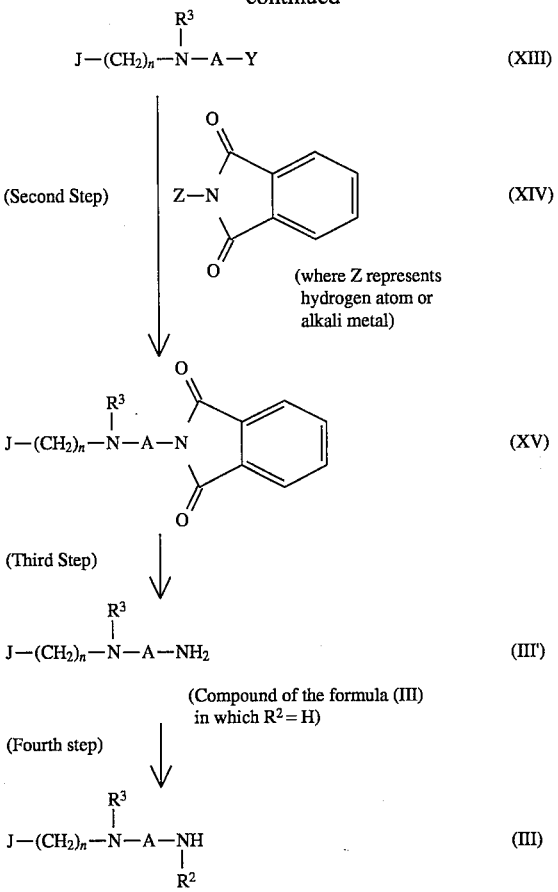

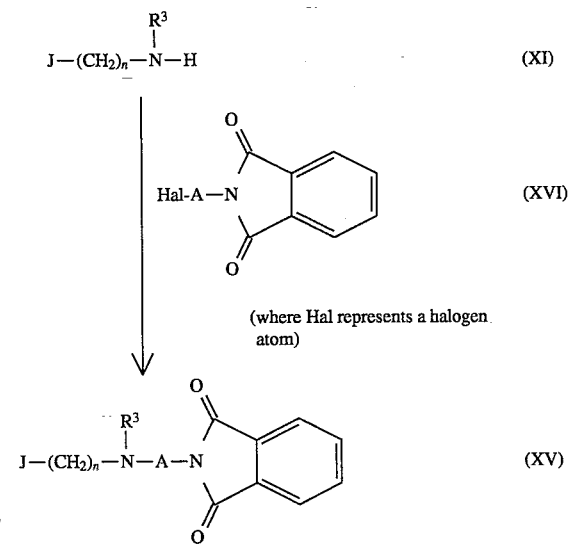

where $R^2$, $R^3$, n, A and J in each of the formulae have the same meanings as described above.

(First Step)

In this step, the compound (XIII) is formed by reacting a compound represented by the formula (XI) and a compound represented by the formula (XII) by a customary method.

Specifically, the compound (XIII) is formed by reacting both of the compounds at a temperature from a room temperature to a heat refluxing temperature by using a solvent, for example, benzene, toluene, xylene, dimethylformamide, acetonitrile, dimethylsulfoxide, dioxane and tetrahydrofuran and under the presence of a base, for example, potassium carbonate, sodium carbonate, triethylamine and diisopropylethylamine.

(Second Step)

In a case where Y represents a stripping group, for example, a halogen atom on methane sulfonyloxy, a compound represented by the formula (XIII) is reacted with an alkali metal salt of phthalimide represented by the formula (XIV) such as potassium phthalimide or sodium phthalimide under the presence of a base such as potassium carbonate or sodium carbonate, to form a compound represented by the formula (XV). When Y is a protected hydroxy, for example trityloxy or tert-butyldimethylsiloxy, the protecting group is removed by a conventional method and then Mitsunobu reaction using phthalimide, trimethylphosphine and diethylazodicarboxylate is conducted to prepare a compound of the formula (XV). In this case, an inert solvent not relevant to the reaction, preferably, dimethylsulfoxide, dimethylformamide, dimethylacetoamide, acetonitrile, tetrahydrofuran, etc. are used as the solvent.

(Third Step)

A compound (III'), where $R^3$=H in the formula (III), can be formed by reacting a compound represented by the formula (XV), for example, with a hydrazine monohydrate under heat reflux in the presence of an organic solvent such as methanol or ethanol.

(Fourth Step)

A compound represented by the formula (III) can be formed by conducting amidizing reduction between a compound represented by the formula (III'), in which $R^3$=H in the formula (III), and an aldehyde or ketone by using a catalyst such as palladium-carbon, platinum oxide, Raney nickel, etc. in a hydrogen atmosphere.

In this case, acetone, cyclobutanone, cyclopentanone or benzaldehyde can be used as the aldehyde or ketone. As the reaction solvent, there can be used methanol, ethanol, benzene, toluene, xylene, dimethylformamide, tetrahydrofuran, dioxane and ethyl acetate.

As an alternative method, a compound represented by the formula (III) can be formed by converting a compound represented by the formula (III') into an acidamide or carbamate, for example, N-formyl, N-acetyl, N-methoxycarbonyl or N-ethoxycarbonyl by a customary method, which is then reduced with a metal hydrogen complex compound, for example, aluminum lithium hydride or borane.

The reductive reaction is conducted at a temperature from a room temperature to a heat refluxing temperature by using a solvent such as ether, tetrahydrofuran, dioxane, 1,2-dimethoxyethane, diethylene glycol dimethyl ether, etc.

The compound (XV) can also be obtained by the following method.

That is, a compound of the formula (XV) is formed by reacting a compound represented by the formula (XI) with a compound represented by the formula (XVI) under the presence of a base, for example, potassium carbonate, sodium carbonate, sodium hydroxide, triethylamine and diisopropyisoethylamine at a temperature from a room temperature to a refluxing temperature.

In this case, those solvents, for example, dimethylsulfoxide, dimethylformamide, dimethylacetoamide and acetonitrile can be used as the solvent.

(Preparation Method 2)

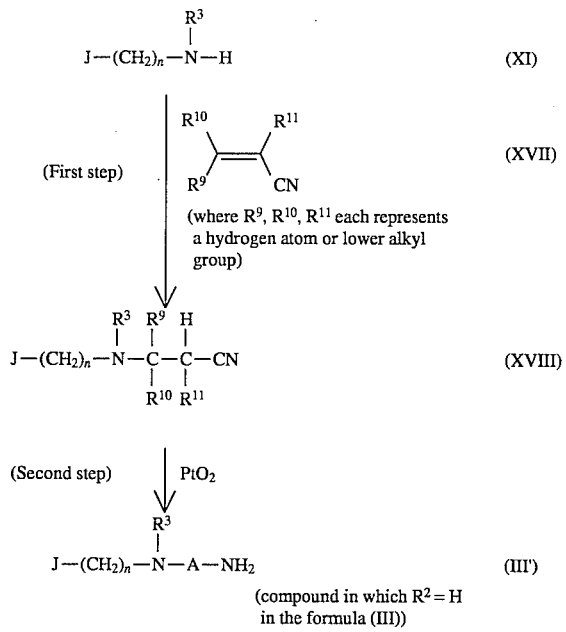

(First Step)

The compound (XVIII) can be formed by reacting a compound represented by the formula (XI) and a compound represented by the formula (XVII) at a temperature from a room temperature to a heat refluxing temperature without using solvent or under the presence of a solvent such as dichloromethane, chloroform, acetonitrile, dimethylformaide, dimethylsulfoxide, ether, tetrahydrofuran, methanol, ethanol, etc.

(Second Step)

The compound represented by the formula (III') can be formed by subjecting a compound represented by the formula (XVIII) to a hydrogenating reaction by using a catalyst such as palladium-carbon, platinum oxide or Raney nickel.

In this case, the reaction is conducted under the pressure from a normal pressure to an elevated pressure and at a temperature from a normal temperature to an elevated temperature while using a solvent, for example, methanol, ethanol, dimethylformamide and ethyl acetate.

(Preparation Method 3)

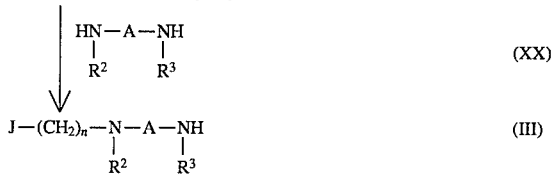

The compound (III) can be formed by reacting a compound represented by the formula (XIX) with a compound of the formula (XX) at a temperature from a room temperature to a heat refluxing temperature under the presence of a base such as potassium carbonate, sodium carbonate, sodium hydroxide, triethylamine and diisopropylethylamine.

As the reaction solvent used in this case, there can be used, for example, those solvents such as dimethylsulfoxide, dimetylformamide, dimethylacetoamide or acetonitrile.

(Pharmacological Test)

Pharmacological tests were conducted for the compounds of the invention including the embodiments I, II and III, in view of (1) the effect upon cardiac muscle extirpated from guinea pig, (2) the heart rate lowering and coronary blood-flow increasing effects upon anesthetized thoracotomized dog and (3) the toxicity.

The test compounds, A to M of I, A to J of II and A to E of III are listed below.

COMPOUNDS A TO M OF I

Compound A (Compound of Example 1)

(E)-N-[3-((N'-(2-(3,4-Dimethoxyphenyl)ethyl)-N'-methyl)amino)propyl]-4-(4-(1H-imidazol-1-yl)phenyl)-3-butenamide Compound B (Compound of Example 2)

(E)-N-[3-((N'-(2-(3,5-Dimethoxyphenyl)ethyl)-N'-methyl)amino)propyl]-4-(4-(1H-imidazol-1-yl)phenyl)-3-butenamide Compound C (Compound of Example 3)

(E)-N-[3-((N'-(2-(3,4-Dimethoxyphenyl)ethyl)-N'-methyl)amino)butyl]-4-(4-(1H-imidazol-1-yl)phenyl)-3-butenamide Compound D (Compound of Example 19)

(E)-N-[3-((N'-(2-(3,4-Dimethoxyphenyl)ethyl)-N'-methyl)amino)propyl]-4-(4-(3-pyridyl)phenyl)-3-butenamide Compound E (Compound of Example 23)

(E)-N-[3-((N'-(2-(3,4-Dimethoxyphenyl)ethyl)-N'-methyl)amino)propyl]-4-(4-(1H-pyrrol-1-yl)phenyl)-3-butenamide Compound F (Compound of Example 26)

(E)-N-[3-((N'-(2-(3,4-Dimethoxyphenyl)ethyl)-N'-methyl)amino)propyl]-4-(4-(1H-benzimidazol-1-yl)phenyl)-3-butenamide Compound G (Compound of Example 9)

(E)-N-[3-((N'-(2-Phenylethyl)-N'-methyl)amino)propyl]-4-(4-(1H-imidazol-1-yl)phenyl)-3-butenamide Compound H (Compound of Example 10)

(E)-N-[3-((N'-(2-(3,4,5'-Trimethoxyphenyl)ethyl)-N'-methyl)amino)propyl]-4-(4-(1H-imidazol-1-yl)phenyl)-3-butenamide Compound I (Compound of Example 29)

(E)-N-[3-((N'-(2-(3,4-Dimethoxyphenyl)ethyl)-N'-methyl)amino)propyl]-4-(4-(4-(1H)-pyridon-1-yl)phenyl)-3-butenamide Compound J (Compound of Example 7)

(E)-N-[3-((N'-(2-(3-Methoxyphenyl)ethyl)-N'-methyl)amino)propyl]-4-(4-(1H-imidazol-1-yl)phenyl)-3-butenamide Compound K (Compound of Example 13)

(E)-N-[3-((N'-(2-(3,4-Methylenedioxyphenyl)-ethyl)-N'-methyl)amino)propyl]-4-(4-(1H-imidazol-1-yl)phenyl)-3-butenamide Compound L (Compound of Example 18)

(E)-N-[3-((N'-(2-(3,4-Dimethoxyphenyl)ethyl)-N'-methyl)amino)propyl]-4-(4-(4-methyl-1H-imidazol-1-yl)phenyl)-3-butenamide Compound M (Compound of Example 25)

(E)-N-[3-((N'-(2-(3,4-Dimethoxyphenyl)ethyl)-N'-methyl)amino)propyl]-4-(4-(1H-1,2,4-triazol-1-yl)phenyl)-3-butenamide

COMPOUNDS A TO J OF II

A: (E)-N-(3-((N'-(2-(3,4-dimethoxyphenyl)ethyl)-N'-methyl)amino)propyl)-4-(4-fluorophenyl)-3-butenamide dihydrochloride,
B: (E)-N-(3-((N'-(2-(3,4-dimethoxyphenyl)ethyl)-N'-methyl)amino)propyl)-4-(3,4-methylenedioxy)phenyl)-3-buteneamide dihydrochloride,
C: (E)-N-(3-((N'-(2-(3,4-dimethoxyphenyl)ethyl)-N'-methyl)amino)propyl)-3-(4-fluorophenyl)propeneamide,
D: (E)-N-(3-((N'-(2-(3,4-dimethoxyphenyl)ethyl)-N'-methyl)amino)propyl)-3-(4-cyanophenyl)propeneamide,
E: (E)-N-(3-((N'-(2-(3,4-dimethoxyphenyl)ethyl)-N'-methyl)amino)propyl)-3-(4-fluorobenzylidene)-2-pyrrolidinone,
F: (E)-N-(3-((N'-(2-(4-methoxyphenyl)ethyl)-N'-allyl)amino)propyl)-3-(4-fluorophenyl)propeneamide,
G: (E)-N-(3-((N'-(3-(3,4-dimethoxyphenyl)pyrrolidine-1-yl)propyl)-3-(4-fluorophenyl)-propeneamide,
H: (E)-N-(3-((N'-(2-(3,4-dimethoxyphenyl)ethyl)-N'-methyl)amino)propyl)-4-(4-methoxyphenyl)-3-buteneamide,
I: (E)-N-(3-((N'-(2-(3,4-dimethoxyphenyl)ethyl)-N'-methyl)amino)propyl)-4-(3,4,5-trimethoxyphenyl)-3-buteneamide,
J: (E)-N-(3-((N'-(2-(3,4-dimethoxyphenyl)ethyl)-N'-methyl)amino)propyl)-N-cyclopentyl-4-(4-cyanophenyl)-3-buteneamide,

COMPOUNDS A TO E OF III

A: (E)-N-(3-((N'-(2-(3,4-dimethoxyphenyl)ethyl)-N'-methyl)amino)propyl)-4-(4-(1,3-thiazol-4-yl)phenyl)-3-buteneamide,
B: (E)-N-(N'-(2-(3,4-dimethoxyphenyl)ethyl)-3-pyrrolidino)-4-(4-(1H-imidazol-1-yl)phenyl)-3-buteneamide,
C: (E)-N-(2-(N'-(2-(3,4-dimethoxypehnyl)ethyl)-2-pyrrolidino)ethyl)-4-(4-(1H-imidazol-1-yl)phenyl)-3-buteneamide,
D: (E)-N-(3-(N'-(2-(3,4-dimethoxyphenyl)ethyl)-N'-methyl)amino)propyl)-4-(4-(1H-imidazol-1-yl)thiophene-2-yl)-3-buteneamide,
E: (E)-N-(3-((N'-(3-(3,4-dimethoxyphenyl)-2-propyl)-N'-methyl)amino)propyl)-4-(4-(1H-imidazol-1-yl)phenyl)-3-buteneamide.

Now, Pharmacological Experiment Examples will be described to illustrate the effect of the compound of the present invention in more detail.

PHARMACOLOGICAL EXPERIMENT EXAMPLE

Experimental Example 1

Effect Upon Cardiac Muscle Extirpated From Guinea Pig

The effect of the compound (test compound) of the present invention upon cardiac muscle was examined by using a male guinea pig having a weight of 300 to 500 g. Namely, a right atrium was extirpated from a male guinea pig and perfused with a Krebs-Henseleit solution to count its spontaneous contractions with a cardiotachometer. The cologarithm of the concentration of a test compound at which the heart rate was reduced by 30% is shown in Table 1.

TABLE 1

| Effect upon cardiac muscle extirpated from guinea pig | |
|---|---|
| (I) | |
| Test compound | $-\log EC_{30}$ |
| Compound A | 6.3 |
| Compound B | 5.9 |
| Compound C | 6.0 |
| Compound D | 6.8 |
| Compound E | 6.6 |
| Compound F | 6.1 |
| Compound G | 6.1 |
| Compound H | 5.5 |
| (II) | |
| test compound | $-\log EC_{30}$ |
| compound A | 6.6 |
| B | 6.8 |

TABLE 1-continued

Effect upon cardiac muscle extirpated from guinea pig

| | | |
|---|---|---|
| | C | 6.0 |
| | D | 6.1 |
| | E | 6.3 |

(III)

| test compound | | −log EC30 |
|---|---|---|
| compound | A | 6.4 |
| | B | 6.5 |
| | C | 6.2 |
| | E | 5.7 |

Experimental Example 2

Heart Rate Lowering and Coronary Bloodflow Increasing Effects Upon Anesthetized Thoracotomized Dog The chest of a grown-up mongrel was opened under enflurane inhalation anesthesia. The blood flow of the coronary artery was determined by setting a probe of an electromagnetic bloodflowmeter at its left circumflexbranch, while the heart rate was determined by triggering the wave form of the pressure in its left ventricle and counting it with a tachometer.

The intravenous administration of a test compound (in a dose of 0.3 mg per kg of the weight of the anesthetized mongrel) was carried out by using a catheter inserted into its femoral artery.

The effect of increasing the bloodflow of the circumflex branch of the left coronary artery or the heart rate lowering effect was evaluated based on the difference between the bloodflow or the heart rate after the administration and that before the administration according to the following criteria. The results are shown in Table 2 by a symbol (+).

TABLE 2

Heart rate lowering and coronary bloodflow increasing effects on anesthetized thoracotomized dog

(I)

| Test compound | Heart rate (HR) | Coronary bloodflow (CBF) |
|---|---|---|
| Compound A | +++ | + |
| Compound B | ++ | +++ |
| Compound C | + | +++ |
| Compound I | ± | +++ |
| Compound J | + | + |
| Compound K | ++ | + |
| Compound L | + | + |
| Compound M | + | + |

(II)

| test compound | | heart rate (HR) |
|---|---|---|
| compound | A | ++ |
| | B | +++ |
| | D | +++ |
| | F | +++ |
| | G | ++ |
| | H | ++ |

TABLE 2-continued

Heart rate lowering and coronary bloodflow increasing effects on anesthetized thoracotomized dog

| | I | + |
| | J | + |

(III)

| test compound | heart rate (HR) | coronary bloodflow (CBF) |
|---|---|---|
| compound   A | +++ | ± |
| B | + | + |
| D | ++ | + |

Note) Symbols "+", "++", "+++" and "±" each stand for a rate of reduction in heart rate or a rate of increase in coronary bloodflow as shown in Table 3.

TABLE 3

| Rate of reduction in HR | | Rate of increase in CBF | |
|---|---|---|---|
| ± | 0% | ± | 0% |
| + | 1–10% | + | 1–100% |
| ++ | 11–20% | ++ | 101–200% |
| +++ | 21–30% | +++ | 201–300% |

Experimental Example 3

Toxicity Test

The representative compounds of the present invention were examined by an ordinary acute toxicity test (intravenous injection) using a mouse to obtain the results shown in Table 4.

TABLE 4

| Test compound | $LD_{50}$ (mg/kg, iv) |
|---|---|
| Compound A | 92 |
| Compound B | 81 |
| Compound C | 92 |
| Compound I | 77 |
| Compound J | 77 |
| Compound L | 92 |
| Compound M | 120 |

(EXAMPLES OF THE COMPOUNDS)

The invention will be below illustrated in reference to preparation or manufacturing examples to produce starting materials for the compounds of the invention and examples of the compounds of the invention I, II and III. They are lised below.

| | I | II | III |
|---|---|---|---|
| preparation examples or manufacturing examples | 1–14 | 1–6 | 1–25 |
| examples or working examples | 1–36 | 1–120 | 1–20 |

EXAMPLES OF THE COMPOUND I

Preparative Example 1

4-(4-Methyl-1H-imidazol-1-yl)benzaldehyde

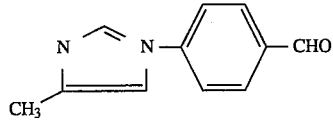

4.20 g of sodium hydride (a 60% suspension thereof in a mineral oil) was suspended in 150 ml of dimethylformamide to obtain a suspension. 8.62 g of 4-methylimidazol was added to the suspension at a room temperature under stirring in portions. After one hour, 12.4 g of 4-fluorobenzaldehyde was added to the obtained mixture. The obtained mixture was stirred for 4 hours and poured into ice-water. The obtained mixture was extracted with chloroform. The extract was dried over anhydrous sodium sulfate and distilled under a reduced pressure to remove the solvent. The obtained residue was purified by silica gel column chromatography (solvent: chloroform/methanol (50:1)) to obtain a solid product. This solid product was washed with ether to obtain 2.67 g of the title compound as a pale yellow powder (yield: 14%).

m.p. (°C.): 85.0 to 85.5 elemental analysis: as $C_{11}H_{10}N_2O$

|  | C | H | N |
|---|---|---|---|
| calculated (%) | 70.95 | 5.41 | 15.05 |
| found (%) | 71.17 | 5.51 | 15.13 |

NMR (CDCl$_3$) δ; 2.29 (3H, d, J=1.5 Hz), 7.04 (1H, m), 7.3~7.5 (2H, m), 7.7~8.1 (3H, m), 9.96 (1H, s)

In a similar manner to the one described above, the following compound was prepared (yield: 55%).

4-(4-(1H)-Pyridon-1-yl)benzaldehyde

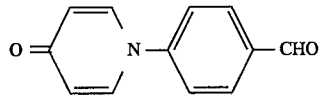

m.p. (°C.): 228 to 230 elemental analysis: as $C_{12}H_9NO_2$

|  | C | H | N |
|---|---|---|---|
| calculated (%) | 72.35 | 4.55 | 7.03 |
| found (%) | 72.58 | 4.64 | 7.04 |

NMR (DMSO-d$_6$) δ; 6.1~6.4 (2H, m), 7.6~7.9 (2H, m), 7.9~8.2 (4H, m), 10.05 (1H, s)

Preparative Example 2

3-(1H-Imidazol-1-yl)benzaldehyde

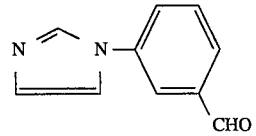

A mixture comprising 9.25 g of 3-bromobenzaldehyde, 20.4 g of imidazole, 0.31 g of copper powder and 50 ml of water was heated under reflux in a nitrogen atmosphere for 3 days, followed by the addition of aqueous ammonia. The obtained mixture was extracted with chloroform. The extract was purified by silica gel column chromatography (solvent: methylene chloride/methanol) to obtain 4.61 g of the title compound as a pale yellow crystal (yield: 54%).

m.p. (°C.): 76.0 to 77.0 elemental analysis: as $C_{10}H_8N_2O$

|  | C | H | N |
|---|---|---|---|
| calculated (%) | 69.75 | 4.68 | 16.27 |
| found (%) | 69.80 | 4.83 | 16.61 |

NMR (CDCl$_3$) δ; 7.20 (1H, bs), 7.31 (1H, m), 7.5~7.7 (2H, m), 7.7~8.0 (3H, m), 10.02 (1H, s)

Preparative Example 3

4-(4-Pyridyl)benzaldehyde

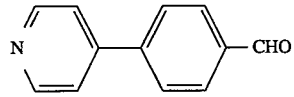

A solution of 6.93 g of 4-bromobenzaldehyde dimethyl acetal in 40 ml of tetrahydrofuran was dropwise added to a mixture comprising 0.80 g of magnesium powder, a catalytic amount of iodine and 10 ml of tetrahydrofuran under stirring at a temperature in the bulk of 40° to 50° C. in a nitrogen atmosphere to prepare a Grignard reagent. This Grignard reagent was dropwise added to a solution of 4.46 g of 4-bromopyridine and 0.4 g of bis(1,3-diphenylphosphinopropane)nickel (II) chloride in 100 ml of tetrahydrofuran at a room temperature in a nitrogen atmosphere. The obtained mixture was refluxed for 4 hours and allowed to cool to a room temperature, followed by the addition of water. The obtained mixture was distilled to remove the tetrahydrofuran. Ethyl acetate was added to the residue. The obtained mixture was extracted with dilute hydrochloric acid thrice. The extracts were combined, allowed to stand for a short time, made alkaline with concentrated aqueous ammonia and extracted with chloroform. The extract was dried over anhydrous magnesium sulfate and distilled to remove the solvent. The residue was purified by silica gel column chromatography (solvent: chloroform/methanol) to obtain 3.28 g of the title compound as a pale yellow crystal (yield: 64%).

m.p. (°C.): 89.5 to 90 elemental analysis: as $C_{12}H_9NO$

|  | C | H | N |
|---|---|---|---|
| calculated (%) | 78.67 | 4.95 | 7.65 |
| found (%) | 78.77 | 5.12 | 7.57 |

NMR (CDCl$_3$) δ; 7.50~7.62 (2H, m), 7.75~7.93 (2H, m), 7.96~8.16 (2H, m), 8.70~8.84 (2H, m), 10.14 (1H, s)

In a similar manner to the one described in Preparative Example 3, the following compounds were prepared:

4-(3-Pyridyl)benzaldehyde

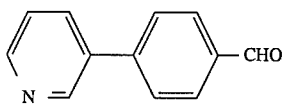

m.p. (°C.): 53.5 to 54.5 elemental analysis: as $C_{12}H_9NO$

|  | C | H | N |
|---|---|---|---|
| calculated (%) | 78.67 | 4.95 | 7.65 |
| found (%) | 78.57 | 5.06 | 7.56 |

NMR (CDCl$_3$) δ; 7.44 (1H, ddd, J=7.2 Hz, 4.7 Hz, 1.0 Hz), 7.6~8.2 (5H, m), 8.75 (1H, m), 8.94 (1H, m), 10.12 (1H, s)

4-(2-Pyridyl)benzaldehyde

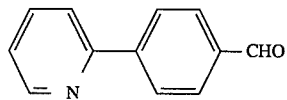

m.p. (°C.): 48.0 to 48.5 elemental analysis: $C_{12}H_9NO$

|  | C | H | N |
|---|---|---|---|
| calculated (%) | 78.67 | 4.95 | 7.65 |
| found (%) | 78.50 | 5.08 | 7.57 |

NMR (CDCl$_3$) δ; 7.22 (1H, m), 7.8~7.5 (2H, m), 7.90 (2H, d, J=8.3 Hz), 8.08 (2H, d, J=8.3 Hz), 8.65 (1H, d, J=4.4 Hz), 9.98 (1H, s)

4-(Imidazo[1,2-a]pyridin-6-yl)benzaldehyde

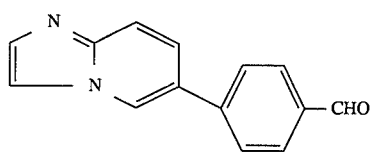

m.p. (°C.): 138.5 to 139.5 elemental analysis: as $C_{14}H_{10}N_2O$

|  | C | H | N |
|---|---|---|---|
| calculated (%) | 75.67 | 4.51 | 12.61 |
| found (%) | 75.58 | 4.67 | 12.68 |

NMR (CDCl$_3$) δ; 7.42 (1H, dd, J=9.0 Hz, 2.5 Hz), 7.55~7.80 (5H, m), 7.84~8.04 (2H, m), 8.15 (1H, m), 9.98 (1H, s)

Preparative Example 4

(E)-4-[4-(1H-Imidazol-1-yl)phenyl]-3-butenoic acid

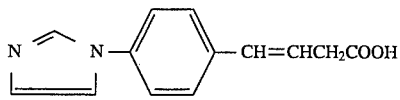

5.45 g of 4-(1H-imidazol-1-yl)benzaldehyde and 12.93 g of β-carboxyethyltriphenylphosphonium chloride were suspended in 70 ml of tetrahydrofuran. The obtained suspension was cooled to −50° C. and vigorously stirred. 30 ml of a solution of 7.83 g of potassium t-butoxide in tetrahydrofuran was gradually added dropwise to the resulting suspension. The temperature of the obtained mixture was gradually raised to 0° C. After one hour, ice-water was added to the mixture. The obtained mixture was washed with ether. The pH of the aqueous layer was adjusted with concentrated hydrochloric acid to about 4 to precipitate a solid. This solid was recovered by filtration and washed with water and methanol to obtain 5.44 g of the title compound as a pale yellow powder (yield: 75%).

m.p. (°C.): 212 to 213.5 elemental analysis: as $C_{13}H_{12}N_2O_2$

|  | C | H | N |
|---|---|---|---|
| calculated (%) | 68.41 | 5.30 | 12.27 |
| found (%) | 68.51 | 5.42 | 12.08 |

NMR (DMSO-d$_6$) δ; 3.21 (2H, d, J=5.7 Hz), 6.33 (1H, dt, J=5.7 Hz, 15.8 Hz), 6.57 (1H, d, J=15.8 Hz), 7.10 (1H, s), 7.3~7.7 (4H, m), 7.72 (1H, s), 8.25 (1H, s)

In a similar manner to the one described above, the following compounds were prepared:

(E)-4-[3-(1H-imidazol-1-yl)phenyl]-3-butenoic acid

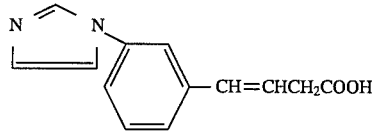

m.p. (°C.): 148.5 to 150.0 elemental analysis: as $C_{13}H_{12}N_2O_2$

|  | C | H | N |
|---|---|---|---|
| calculated (%) | 68.41 | 5.30 | 12.27 |
| found (%) | 68.23 | 5.39 | 12.34 |

NMR (DMSO-d$_6$) δ; 3.22 (2H, d, J=5.4 Hz), 6.4~6.6 (2H, m), 7.07 (1H, s), 7.3~7.6 (3H, m), 7.66 (1H, s), 7.73 (1H, s), 8.24 (1H, s)

(E)-4-[4-(2-Methyl-1H-imidazol-1-yl)phenyl]-3-butenoic acid

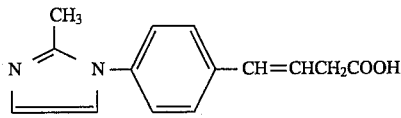

m.p. (°C.): 237 to 240 (dec.)

elemental analysis: as C$_{14}$H$_{14}$N$_2$O$_2$

|  | C | H | N |
|---|---|---|---|
| calculated (%) | 69.40 | 5.82 | 11.57 |
| found (%) | 69.57 | 6.05 | 11.45 |

NMR (DMSO-d$_6$) δ; 2.30 (3H, d, J=0.9 Hz), 3.22 (2H, d, J=6.2 Hz), 6.37 (1H, dt, J=6.2 Hz, 16.3 Hz), 6.61 (1H, d, J=16.3 Hz), 6.92 (1H, m), 7.25 (1H, m), 7.3~7.4 (2H, m), 7.4~7.6 (2H, m)

(E)-4-[4-(4-Methyl-1H-imidazol-1-yl)phenyl]-3-butenoic acid

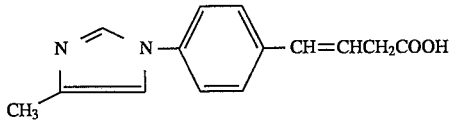

m.p. (°C.): 196 to 198 elemental analysis: as C$_{14}$H$_{14}$N$_2$O$_2$

|  | C | H | N |
|---|---|---|---|
| calculated (%) | 69.40 | 5.82 | 11.57 |
| found (%) | 69.64 | 5.87 | 11.54 |

NMR (DMSO-d$_6$) δ; 2.17 (3H, s), 3.21 (2H, d, J=6.2 Hz), 6.31 (1, dt, J=6.2 Hz, 16.3 Hz), 6.55 (1H, d, J=16.3 Hz), 7.41 (1H, d, J=0.9 Hz), 7.52 (4H, s), 8.13 (1H, d, J=0.9 Hz)

(E)-4-[4-(1H-pyrazol-1-yl)phenyl]-3-butenoic acid

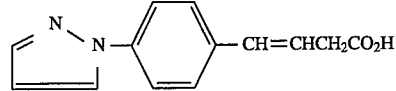

m.p. (°C.): 140 to 142 elemental analysis: as C$_{13}$H$_{12}$N$_2$O$_2$

|  | C | H | N |
|---|---|---|---|
| calculated (%) | 68.41 | 5.30 | 12.27 |
| found (%) | 68.30 | 5.45 | 12.41 |

NMR (CDCl$_3$) δ; 3.20 (2H, d, J=7 Hz), 6.04~6.60 (3H, m), 7.2~8.1 (6H, m)

(E)-4-[4-(1,2,4-Triazol-1-yl)phenyl]-3-butenoic acid

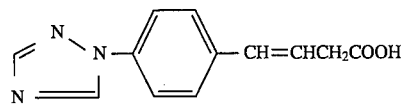

m.p. (°C.): 217 to 218.5 elemental analysis: as C$_{12}$H$_{11}$N$_3$O$_2$

|  | C | H | N |
|---|---|---|---|
| calculated (%) | 62.87 | 4.84 | 18.33 |
| found (%) | 63.07 | 4.95 | 18.34 |

NMR (DMSO-d$_6$) δ; 3.23 (2H, d, J=5.7 Hz), 6.36 (1H, dt, J=5.7 Hz, 15.8 Hz), 6.60 (1H, d, J=15.8 Hz), 7.5~7.7 (2H, m), 7.7~7.9 (2H, m), 8.21 (1H, s), 9.28 (1H, s), 12.35 (1H, br)

(E)-4-[4-(1H-Pyrrol-1-yl)phenyl]-3-butenoic acid

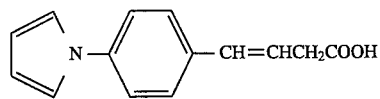

m.p. (°C.): 191.0 to 192.0 elemental analysis: as C$_{14}$H$_{13}$NO$_2$

|  | C | H | N |
|---|---|---|---|
| calculated (%) | 73.99 | 5.77 | 6.16 |
| found (%) | 74.30 | 5.93 | 6.10 |

NMR (CDCl$_3$) δ; 3.17 (2H, d, J=5.8 Hz), 6.04~6.62 (4H, m), 7.30 (2H, m), 7.44 (4H, s)

(E)-4-[4-(3-Pyridyl)phenyl]-3-butenoic acid

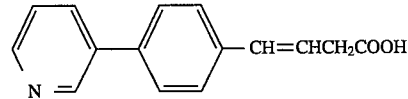

m.p. (°C.): 205.5 to 206.0 elemental analysis: as C$_{15}$H$_{13}$NO$_2$

|  | C | H | N |
|---|---|---|---|
| calculated (%) | 75.30 | 5.48 | 5.85 |
| found (%) | 75.42 | 5.64 | 5.80 |

NMR (DMSO-d$_6$) δ; 3.20 (2H, d, J=5.4 Hz), 6.40 (1H, dt, J=15.5 Hz, 5.4 Hz), 6.50 (1H, d, J=15.5 Hz), 7.4 (1H, m), 7.50 (2H, d, J=8.3 Hz), 7.66 (2H, d, J=8.3 Hz), 8.13 (1H, d, J=7.2 Hz), 8.5 (1H, bs), 8.8 (1H, bs)

47

(E)-4-[4-(2-Pyridyl)phenyl]-3-butenoic acid

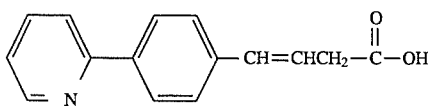

m.p. (°C.): 155.0 to 156.0 elemental analysis: as $C_{15}H_{13}NO_2$

|  | C | H | N |
| --- | --- | --- | --- |
| calculated (%) | 75.30 | 5.48 | 5.85 |
| found (%) | 74.95 | 5.44 | 5.72 |

NMR (DMSO-$d_6$) δ; 3.25 (2H, d, J=5.7 Hz), 6.45 (1H, dt, J=15.8 Hz, 5.7 Hz), 6.58 (1H, d, J=15.8 Hz), 7.30~7.50 (1H, m), 7.58 (2H, d, J=8.4 Hz), 7.80~8.00 (2H, m), 8.08 (2H, d, J=8.4 Hz), 8.65 (1H, m)

(E)-4-[4-(4-Pyridyl)phenyl]-3-butenoic acid

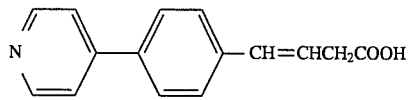

m.p. (°C.): 209.5 to 211.0 elemental analysis: as $C_{15}H_{13}H\ NO_2$

|  | C | H | N |
| --- | --- | --- | --- |
| calculated (%) | 75.30 | 5.48 | 5.85 |
| found (%) | 75.23 | 5.59 | 5.78 |

H-NMR (DMSO-$d_6$) δ; 3.25 (2H, d, J=6.1 Hz), 6.48 (1H, dt, J=15.5 Hz, 6.1 Hz), 6.60 (1H, d, J=15.5 Hz), 7.4~8.0 (6H, m), 8.7 (2H, m)

(E)-4-[4(1H)-Pyridon-1-yl)phenyl]-3-butenoic acid

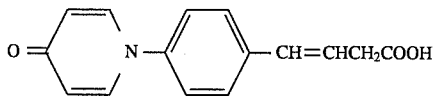

m.p. (°C.): 275 (dec.)

elemental analysis: as $C_{15}H_{13}NO_3$

|  | C | H | N |
| --- | --- | --- | --- |
| calculated (%) | 70.58 | 5.13 | 5.49 |
| found (%) | 70.55 | 5.25 | 5.46 |

H-NMR (DMSO-$d_6$) δ; 3.21 (2H, d, J=5.6 Hz), 6.1~6.3 (2H, m), 6.36 (1H, dt, J=5.6 Hz, 16.3 Hz), 6.60 (1H, d, J=16.3 Hz), 7.3~7.7 (4H, m), 7.8~8.1 (2H, m)

48

(E)-4-[4-(Imidazo[1,2-a]pyridin-6-yl)phenyl]-3-butenoic acid

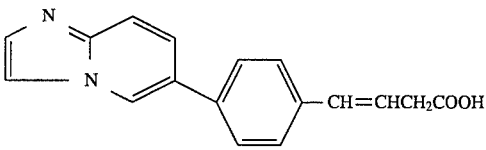

m.p. (°C.): 254 to 260.0 (dec.)

elemental analysis: as $C_{16}H_{14}N_2O_2$

|  | C | H | N |
| --- | --- | --- | --- |
| calculated (%) | 73.37 | 5.07 | 10.07 |
| found (%) | 73.15 | 5.16 | 10.00 |

H-NMR (DMSO-$d_6$) δ; 3.23 (2H, d, J=5.8 Hz), 6.47 (1H, dt, J=15.5 Hz, 5.8 Hz), 6.57 (1H, d, J=15.5 Hz), 7.4~7.8 (7H, m), 7.99 (1H, s), 8.98 (1H, s)

Preparative Example 5

N-[3-{N'-Methyl-N'-(2-(3,5-dimethoxyphenyl)ethyl)amino}propyl]phthalimide

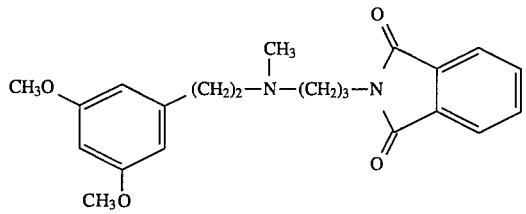

A mixture comprising 9.30 g of N-methyl-(2-(3,5-dimethoxyphenyl)ethyl)amine, 13.4 g of N-(3-bromopropyl)phthalimide, 7.2 g of potassium carbonate and 100 ml of dimethylformamide was stirred at 80° C. for 8 hours. After the completion of the reaction, the reaction mixture was filtered to remove an inorganic matter. The filtrate was distilled to remove the dimethylformamide. Ethyl acetate was added to the residue, The obtained mixture was washed with water and extracted with dilute hydrochloric acid thrice. The extracts were combined, neutralized with concentrated aqueous ammonia and extracted with chloroform. The extract was dried over anhydrous magnesium sulfate and filtered. The filtrate was distilled to remove the solvent. The residue was purified by silica gel column chromatography (solvent: chloroform/methanol) to obtain 12.4 g of the title compound as a pale yellow oil (yield: 64%).

NMR (CDCl$_3$) δ; 1.6~2.0 (2H, m), 2.26 (3H, s), 2.3~2.7 (6H, m), 3.5~3.8 (2H, m), 3.75 (6H, s), 6.20~6.36 (3H, m), 7.50~7.90 (4H, m)

Preparative Example 6

N-Methyl-N-(2-(3,5-dimethoxyphenyl)ethyl)-1,3-propanediamine

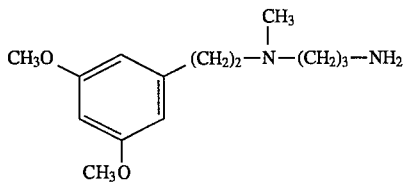

9.24 g of the N-[3-(N'-methyl-N'-(2-(3,5-dimethoxyphenyl)ethyl)amino)propyl]phthalimide prepared in Preparative Example 5 and 4 ml of hydrazine monohydrate were dissolved in 100 ml of ethanol to obtain a solution. This solution was heated under reflux for 2 hours, cooled to a room temperature and filtered to remove generated precipitates. The filtrate was distilled to remove the ethanol. Chloroform was added to the residue. The obtained mixture was washed with an aqueous solution of caustic soda twice and with a saturated aqueous solution of common salt once, dried over anhydrous magnesium sulfate and distilled to remove the solvent. 5.81 g of the title compound was obtained as a pale yellow oil (yield: 96%). This oil was used in the following reaction without any additional purification.

NMR (CDCl$_3$) δ; 1.4~1.8 (2H, m), 1.22 (2H, bs), 2.28 (3H, s) 2.3~2.8 (8H, m) 3.75 (6H, s) 6.2~6.4 (3H, m)

In a similar manner to the one described above, the following compounds were prepared:

N-Methyl-N-[2-(3,4-diethoxyphenyl)ethyl]-1,3-propanediamine

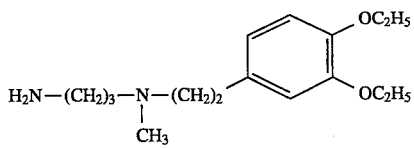

yellow oil

NMR (CDCl$_3$) δ; 1.21 (2H, s), 1.3~1.8 (8H, m), 2.28 (3H, s), 2.3~2.9 (8H, m), 4.04 (2H, q, J=7.0 Hz), 4.07 (2H, q, J=7.0 Hz), 6.6~7.0 (3H, m)

N-Methyl-N-[2-(3,4-ethylenedioxyphenyl)ethyl]-1,3-propanediamine

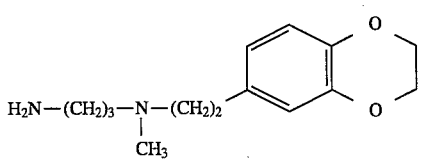

yellow oil

NMR (CDCl$_3$) δ; 1.4~2.1 (4H, m), 2.27 (3H, s), 2.3~2.9 (8H, m), 4.22 (4H, s), 6.4~6.8 (3H, m)

N-Methyl-N-[2-(4-pyridyl)ethyl]-1,3-propanediamine

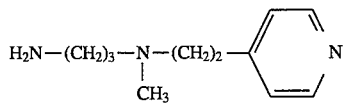

yellow oil

NMR (CDCl$_3$) δ; 1.4~1.8 (2H, m), 2.0~2.9 (13H, m), 6.9~7.2 (2H, m), 8.3~8.6 (2H, m)

N-Methyl-N-(6,7-dimethoxy-1,2,3,4-tetrahydronaphthalen-2-yl)-1,3-propanediamine

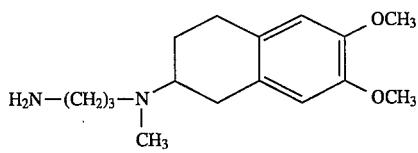

yellow oil

NMR (CDCl$_3$) δ; 1.4~2.2 (6H, m), 2.32 (3H, s), 2.4~2.9 (9H, m), 3.83 (6H, s), 6.56 (2H, s)

N-Methyl-N-(2-phenylethyl)-1,3-propanediamine

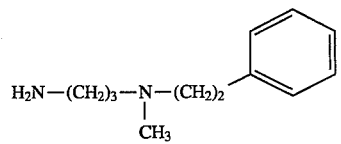

yellow oil

NMR (CDCl$_3$) δ; 1.5~1.8 (4H, m), 2.24 (3H, s), 2.3~2.9 (8H, m), 6.9~7.3 (5H, m)

N-Methyl-N-[2-(3,4-methylenedioxyphenyl)ethyl]-1,3-propanediamine

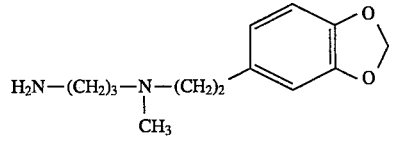

yellow oil

NMR (CDCl$_3$) δ; 1.4~1.8 (4H, m), 2.14 (3H, s), 2.1~2.8 (8H, m), 5.90 (2H, s), 6.4~6.7 (3H, m)

N-Methyl-N-[2-(3-methoxyphenyl)ethyl]-1,3-propanediamine

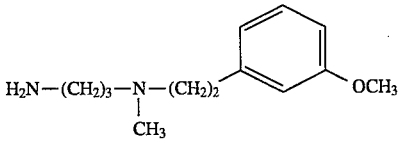

yellow oil

NMR (CDCl$_3$) δ; 1.30 (2H, s), 1.4~1.8 (2H, m), 2.14 (3H, s), 2.2~2.9 (8H, m), 3.84 (3H, s), 6.5~6.8 (3H, m), 6.9~7.2 (1H, m)

N-Allyl-N-[2-(4-methoxyphenyl)ethyl]-1,3-propanediamine

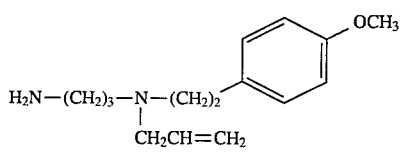

yellow oil

NMR (CDCl₃) δ; 1.40 (2H, s), 1.4~1.8 (2H, m), 2.4~2.8 (8H, m), 3.10 (2H, d, J=7 Hz), 3.74 (3H, s), 4.96~5.30 (2H, m), 5.76~6.02 (1H, m), 6.6 (2H, d, J=10 Hz), 7.0 (2H, d, J=10 Hz)

Preparative Example 8

N-Cyclopentyl-N'-methyl-N'-[2-(3,4-dimethoxyphenyl)ethyl]-1,3-propanediamine

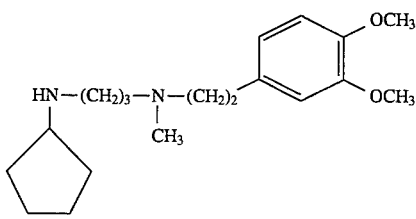

500 mg of N-methyl-N-[2-(3,4-dimethoxyphenyl)ethyl]-1,3-propanediamine and 0.21 ml of cyclopentanone were dissolved in 5 ml of ethanol, followed by the addition of 10 mg of platinum oxide to carry out hydrogenation at a room temperature under 1 atm for 6 hours. The reaction mixture was filtered to remove the catalyst. The filtrate was concentrated under a reduced pressure to obtain 660 mg of the title compound as a yellow oil (yield: 100%).

NMR (CDCl₃) δ; 1.1~2.1 (10H, m), 2.2~2.9 (12H, m), 2.9~3.2 (1H, m), 3.84 (3H, s), 3.86 (3H, s), 6.6~6.9 (3H, m)

Preparative Example 9

N-[2-(3,4-Dimethoxyphenyl)ethyl]homopiperazine

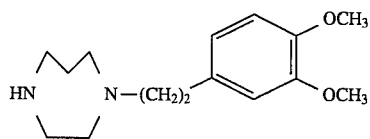

32.27 g of homopiperazine, 13.2 g of 2-(3,4-dimethoxyphenyl)ethyl chloride and 71.3 g of potassium carbonate were added to 500 ml of acetonitrile. The obtained mixture was heated under reflux for 20 hours, cooled and filtered. The filtrate was concentrated under a reduced pressure to obtain a residue. This residue was extracted with ether thrice. The extracts were combined, dried over anhydrous sodium sulfate and filtered. The filtrate was concentrated under a reduced pressure. The obtained residue was purified by silica gel column chromatography (solvent: chloroform/methanol/isopropylamine (100:10:1)) to obtain 13.40 g of the title compound as a yellow oil (yield: 77%).

NMR (CDCl₃) δ; 1.83~1.98 (2H, m), 2.39~3.11 (13H, m), 3.83 (3H, s), 3.84 (3H, s), 6.55~6.83 (3H, m)

Preparative Example 10

N,N'-Dimethyl-N-[2-(3,4-dimethoxyphenyl)ethyl]-1,3-propanediamine

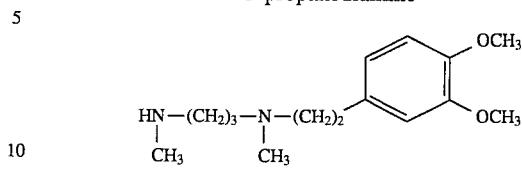

3.0 g of N-methyl-N-2-(3,4-dimethoxyphenyl)ethyl-1,3-propanediamine was dissolved in a mixture comprising 1.8 ml of triethylamine and 100 ml of dichloromethane, followed by stirring under cooling with ice-water. 1.0 ml of methyl chloroformate was dropwise added to the obtained solution. The obtained mixture was stirred for several minutes and distilled to remove the dichloromethane. The residue was extracted with ethyl acetate. The extract was dried over anhydrous magnesium sulfate and distilled to remove the solvent. Thus, 2.84 g of a methylcarbamate was obtained. This methylcarbamate was dissolved in 100 ml of tetrahydrofuran to obtain a solution. This solution was dropwise added to a solution of 0.54 g of lithium aluminum hydride in 100 ml of tetrahydrofuran. The obtained mixture was heated under reflux for 2 hours and cooled with ice. 0.5 ml of water, 0.5 ml of a 15% aqueous solution of caustic soda and 1.5 ml of water were added to the resulting mixture successively. The obtained mixture was stirred at a room temperature for 30 minutes, followed by the addition of magnesium sulfate. The obtained mixture was filtered and the filtrate was distilled to remove the solvent. Thus, 2.30 g of the title compound was obtained as a light brown oil (yield: 72%).

NMR (CDCl₃) δ; 1.44 (1H, bs), 1.5~1.9 (2H, m), 2.28 (3H, s), 2.39 (3H, s), 2.4~2.9 (8H, m), 3.83 (3H, s), 3.85 (3H, s), 6.6~6.9 (3H, m)

Preparative Example 11

N-Methyl-N-(4-(tert-butyldimethylsiloxy)-butan-2-yl)-[2-(3,4-dimethoxyphenyl)ethyl]amine

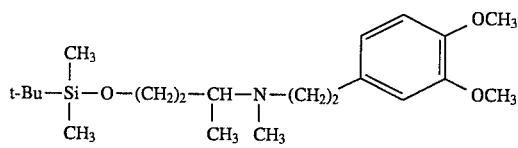

2.39 g of methanesulfonyl chloride was gradually added to 50 ml of a solution of 3.55 g of 4-(tert-butyldimethylsiloxy)butan-2-ol and 2.1 g of triethylamine in ether under cooling with ice. After 30 minutes, water was added to the obtained mixture. The obtained mixture was extracted with ether. The extract was dried over anhydrous sodium sulfate, filtered and distilled to remove the ether. The residue was dissolved in 50 ml of acetonitrile, followed by the addition of 6.74 g of N-methyl[2-(3,4-dimethoxyphenyl)ethyl]amine hydroiodide and 7.7 g of potassium carbonate. The obtained mixture was heated under reflux for 12 hours, cooled and filtered to remove generated crystalline precipitates. The filtrate was concentrated under a reduced pressure and extracted with ether thrice. The ether layers were combined, washed with an aqueous solution of common salt, dried over anhydrous sodium sulfate and filtered. The filtrate was concentrated under a reduced pressure and purified by silica gel column chromatography (solvent: chloroform/methanol (100:1)) to obtain 2.34 g of the title compound as a yellow oil (yield: 35%).

NMR (CDCl₃) δ; 0.05 (6H, s), 0.88 (9H, s), 0.94 (3H, d, J=6.1 Hz), 1.26~1.95 (2H, m), 2.24 (3H, s), 2.36~3.03 (5H, m), 3.58 (2H, t, J=5.8 Hz), 3.81 (3H, s), 3.83 (3H, s), 6.55~6.80 (3H, m)

Preparative Example 12

N-[3-((N'-Methyl-N'-2-(3,4-dimethoxyphenyl)ethyl)amino)butyl]phthalimide

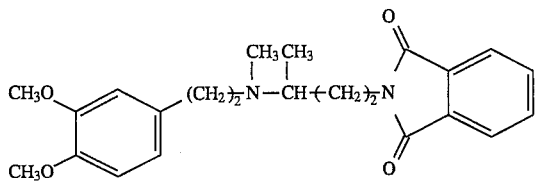

N-Methyl-N-(4-(t-butyldimethylsiloxy)-butan-2-yl)-[2-(3,4-dimethoxyphenyl)ethyl]amine was dissolved in 12 ml of tetrahydrofuran to obtain a solution. 12 ml of a solution (1 mmol/ml) of tetra-n-butylammonium fluoride in tetrahydrofuran was gradually added dropwise to the above solution at a room temperature. The obtained mixture was stirred at a room temperature for 3 hours and distilled to remove the solvent. The residue was extracted with ether thrice. The extracts were combined, dried over anhydrous sodium sulfate and concentrated under a reduced pressure. The residue was dissolved in 12 ml of tetrahydrofuran, followed by the addition of 900 mg of phthalimide and 1.61 g of triphenylphosphine. 1.07 g of diethyl azodicarboxylate was gradually added to the obtained mixture at a room temperature. The obtained mixture was stirred overnight and distilled to remove the solvent. The residue was made acidic with 0.5N hydrochloric acid and washed with ether. The aqueous layer was made basic with lithium hydroxide and extracted with ethyl acetate. The extract was dried over anhydrous sodium sulfate and filtered. The filtrate was concentrated under a reduced pressure and purified by silica gel column chromatography (solvent: chloroform/methanol (100:1)) to obtain 2.19 g of the title compound as a yellow oil (yield: 90%).

NMR (CDCl₃) δ; 0.96 (3H, d, J=6.5 Hz), 1.43~2.01 (2H, m), 2.27 (3H, s), 2.44~2.93 (5H, m), 3.60~3.81 (2H, m), 3.91 (3H, s), 3.85 (3H, s), 6.80 (3H, m), 7.57~7.97 (4H, m)

Preparative Example 13

3-[N-Methyl-N-(2-(3,4-dimethoxyphenyl)ethyl)amino]butylamine

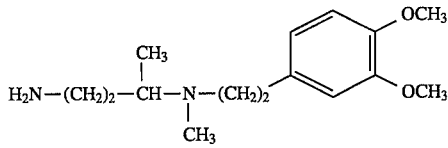

46.36 g of N-[3-(N'-methyl-2-(3,4-dimethoxyphenyl)ethyl)amino-3-methylpropyl]phthalimide and 7.03 g of hydrazine monohydrate were added to 500 ml of ethanol. The obtained mixture was heated under reflux for 2 hours, cooled and filtered to remove generated white precipitates. The filtrate was concentrated under a reduced pressure to obtain a residue. 200 ml of a 10% aqueous solution of sodium hydroxide was added to the residue, followed by the extraction with chloroform thrice. The extracts were combined, washed with a saturated aqueous solution of common salt, dried over anhydrous sodium sulfate and concentrated under a reduced pressure to obtain 26.88 g of the title compound as a yellow oil (yield: 86%).

NMR (CDCl₃) δ; 0.93 (3H, d, J=6.3 Hz), 0.93~1.82 (4H, m), 2.12 (3H, s), 2.24~2.93 (7H, m), 3.78 (3H, s), 3.83 (3H, s), 6.54~6.84 (3H, m)

Preparative Example 14

N-Methyl-N-[2-(3,4-dimethoxyphenyl)ethyl]-2-methyl-1,3-propanediamine

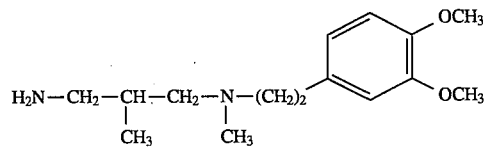

A mixture comprising 6.5 g of N-methyl-2-(3,4-dimethoxyphenyl)ethylamine hydroiodide, 1.6 g of methacrylonitrile and 2.4 g of triethylamine was heated at about 70° C. for 2.5 hours and cooled, followed by the addition of dichloromethane. The obtained mixture was washed with water, dried over magnesium sulfate and distilled to remove the solvent. The residue was purified by silica gel column chromatography (solvent: dichloromethane/ethanol (100:1)) to obtain 2.1 g of 3-[N-methyl-N-(2-(3,4-dimethoxyphenyl)ethyl)amino]-2-methylpropionitrile.

NMR (CDCl₃) δ; 1.24 (3H, d, J=7 Hz), 2.30 (3H, s), 2.3~2.8 (7H, m), 3.8 (6H, s), 6.5~6.8 (3H, m)

2.1 g of the above nitrile and 0.2 ml of concentrated hydrochloric acid were dissolved in 30 ml of ethanol, followed by the addition of 0.2 g of platinum oxide to carry out hydrogenation under a hydrogen pressure of 2.1 kg/cm². The reaction mixture was filtered to remove the catalyst. The filtrate was distilled under a reduced pressure to remove the ethanol. The residue was made alkaline with a dilute solution of caustic soda. The aqueous layer was extracted with dichloromethane. The extract was washed with water, dried over magnesium sulfate and distilled under a reduced pressure to obtain 1.98 g of the title compound as a pale yellow oil (yield: 38%).

NMR (CDCl₃) δ; 0.90 (3H, d, J=7 Hz), 1.36 (2H, s), 1.50~1.80 (1H, m), 2.10 (3H, s), 2.1~2.8 (8H, m), 3.80 (3H, s), 3.84 (3H, s), 6.6~6.8 (3H, m)

Example 1

(E)-N-[3-((N'-(2-(3,4-Dimethoxyphenyl)ethyl)-N'-methyl)amino)propyl]-4-(4-(1H-imidazol-1-yl)phenyl)-3-butenamide

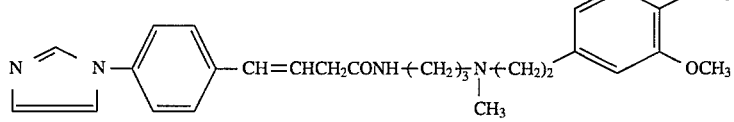

62.1 g of (E)-4-[4-(1H-imidazol-1-yl)phenyl]-3-butenoic acid and 36.8 g of N-hydroxybenzotriazole were added to 800 ml of acetonitrile containing 50% of water, followed by stirring under cooling with ice-water. 56.2 g of N,N'-dicyclohexylcarbodiimide was added to the obtained mixture in portions. The obtained mixture was stirred for 2 hours, followed by the dropwise addition of 65.4 g of N-methyl-N-[2-(3,4-dimethoxyphenyl)ethyl]-1,3-propanediamine. After the completion of the above dropwise addition, the obtained mixture was stirred at a room temperature for 3 days and filtered to remove generated precipitates. The filtrate was sufficiently washed with ethyl acetate and extracted with dilute hydrochloric acid. The pH of the aqueous layer was adjusted with potassium carbonate to 9. The resulting layer was extracted with ethyl acetate. The extract was dried over anhydrous sodium sulfate, concentrated under a reduced pressure and purified by silica gel column chromatography (solvent: chloroform/methanol/concentrated aqueous ammonia (1000:100:2)) to obtain 61.7 g of the title compound as a pale yellow oil (yield: 52%).

NMR (CDCl$_3$) δ; 1.5~1.8 (2H, m), 2.20 (3H, s), 2.3~2.8 (6H, m), 3.02 (2H, d, J=6.5 Hz), 3.2~3.5 (2H, m), 3.84 (3H, s), 3.86 (3H, s), 6.20 (1H, dt, J=6.1 Hz, 15.8 Hz), 7.46 (1H, d, J=15.8 Hz), 6.5~6.8 (3H, m), 7.1~7.5 (7H, m), 7.77 (1H, s)

Example 2

(E)-N-[3-((N'-(2-(3,5-Dimethoxyphenyl)ethyl)-N'-methyl)amino)propyl]-4-(4-(1H-imidazol-1-yl)phenyl)-3-butenamide

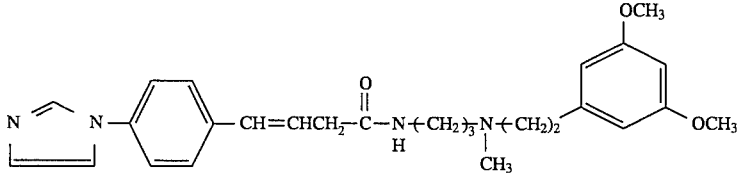

60 g of (E)-4-[4-(1H-imidazol-1-yl)phenyl]-3-butenoic acid was added to 1000 ml of acetonitrile containing 50% of water. The obtained mixture was stirred under cooling with ice-water, followed by the addition of 57.0 g of N,N'-dicyclohexylcarbodiimide and 37.3 g of N-hydroxybenzotriazole. The obtained mixture was stirred for about 4 hours to obtain a solution. A solution of 66.3 g of N'-methyl-N-(2-(3,5-dimethoxyphenyl)ethyl)-1,3-propanediamine in about 60 ml of acetonitrile was dropwise added to the above solution. The temperature of the obtained mixture was raised to a room temperature. The resulting mixture was stirred overnight, heated to a temperature of 30° to 40° C. and stirred for about 4 hours. After the completion of the reaction, the reaction mixture was filtered to remove generated precipitates. The filtrate was distilled to remove the acetonitrile, followed by the addition of ethyl acetate. The obtained mixture was extracted with dilute hydrochloric acid twice. The extracts were combined, neutralized with concentrated aqueous ammonia and extracted with chloroform. The extract was dried over anhydrous magnesium sulfate and distilled to remove the solvent, thus giving a yellow oil. This yellow oil was purified by silica gel column chromatography (solvent: chloroform/methanol/concentrated aqueous ammonia (100:10:0.2)) to obtain 74 g of the title compound as a pale yellow oil (yield: 62%).

NMR (CDCl$_3$) δ; 1.5~1.8 (2H, m), 2.17 (3H, s), 2.3~2.5 (6H, m), 3.01 (2H, d, J=5.4 Hz), 3.1~3.5 (2H, m), 3.72 (6H, s), 6.0~6.3 (4H, m), 6.40 (1H, d, J=15.5 Hz), 7.1~7.5 (7H, m), 7.78 (1H, s)

Dihydrochloride dihydrate of the above produced butenamide was prepared in the following way.

258.9 g of the above produced product was dissolved in 7770 ml of acetone and 518 ml of water was added to the solution. The mixture was cooled with ice. 210 ml of an acetone solution of 100 ml of concentrated hydrochloric acid was added thereto dropwise and the mixture was stirred over one night. The precipitates obtained in the mixture was taken with filtration and washed with 1 liter of acetone. They were then dried at 55 degree C. to obtain 270 g of the dihydrochloride dihydrate, being white to light yellow powder, with a production yield of 90.1%. The product was found to show a heat-absorption peak around 100 degree C. according to DSC. With reference to C27H34N4O3.2HCL.2H2O, results of Its element analyses was:

|  | C | H | N |
|---|---|---|---|
| calcd. | 56.74 | 7.05 | 9.80 |
| found | 56.72 | 6.93 | 9.86 |

Example 3

(E)-N-[3-((N'-(2-(3,4-Dimethoxyphenyl)ethyl)-N'-methyl)amino)butyl]-4-(4-(1H-imidazol-1-yl)phenyl)-3-butenamide

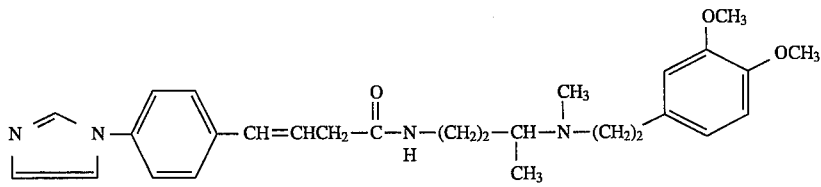

51.2 g of (E)-4-[4-(1H-imidazol-1-yl)phenyl]-3-butenoic acid and 27.24 g of N-hydroxybenzotriazole were dissolved in a mixture comprising 500 ml of water and 500 ml of acetonitrile, followed by the addition of 41.6 g of N,N'-dicyclohexylcarbodiimide. The obtained mixture was stirred at 0° C. for 30 minutes, followed by the slow stepwise addition of a solution of the 3-(N-methyl-N-(2-(3,4-dimethoxyphenyl)ethyl)amino)butylamine prepared in Preparative Example 13 in 160 ml of acetonitrile. The obtained mixture was stirred at a room temperature overnight, heated at 40° C. for 2 hours, cooled and filtered. The filtrate was concentrated under a reduced pressure. The pH of the aqueous layer was adjusted to 3, followed by the addition of ethyl acetate. The obtained mixture was shaken to remove the organic layer. The remaining aqueous layer was made alkaline with sodium hydroxide and extracted with ethyl acetate thrice. The ethyl acetate layers were combined, dried over sodium sulfate and concentrated under a reduced pressure to obtain a residue. This residue was purified by silica gel column chromatography (solvent: chloroform/methanol/concentrated aqueous ammonia (1000:100:2)) to obtain 57.7 g of the title compound as a pale yellow oil (yield: 63%).

NMR (400 MHz, CDCl$_3$) δ; 0.92 (3H, d, J=6.2 Hz), 1.40~1.65 (2H, m), 2.18 (3H, s), 2.50~2.70 (4H, m), 2.75~2.90 (1H, m), 3.02 (2H, d, J=7.0 Hz), 3.05~3.20 (1H, m), 3.50~3.60 (1H, m), 3.83 (3H, s), 3.85 (3H, s), 6.30 (1H, dt, J=7.0 Hz, 16.1 Hz) 6.47 (1H, d, J=16.1 Hz) 6.62~6.71 (2H, m), 6.76 (1H, d, J=8.1 Hz), 7.16 (1H, bs), 7.26 (1H, m), 7.29 (2H, d, J=8.4 Hz), 7.43 (2H, d, J=8.4 Hz), 7.83 (1H, bs)

Examples 4 to 36

The compounds described in Examples 4 to 37 were each prepared in a similar manner to the one described in Example 1.

Namely, the compounds were each prepared by the same procedure as the one described in Example 1 except that the (E)-4-[4-(1H-imidazol-1-yl)phenyl]-3-butenoic acid was replaced by the corresponding 4-substituted phenyl-3-butenoic acid and the N-methyl-N-[2-(3,4-dimethoxyphenyl)ethyl]-1,3-propanediamine was replaced by the corresponding substituted alkylenediamine.

Example 4

(E)-N-[3-((N'-(2-(3,4-Dimethoxyphenyl)ethyl)-N'-methyl)amino)propyl]-N-cyclopentyl-4-(4-(1H-imidazol-1-yl)phenyl)-3-butenamide

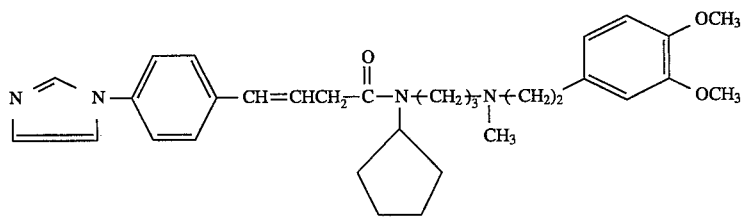

NMR (CDCl$_3$) δ; 1.2~2.0 (10H, s), 2.30 (3H, s), 2.3~2.8 (6H, m), 3.0~3.4 (5H, m), 3.80 (3H, s), 3.83 (3H, s) 6.24 (1H, dt, J=7.2 Hz, 16.0 Hz), 6.46 (1H, d, J=16.0 Hz), 6.5~6.8 (3H, m), 7.1~7.5 (6H, m), 7.77 (1H, s)

Example 5

(E)-N-[3-((N'-(2-(4-Pyridylethyl)-N'-methyl)amino)propyl]-4-(4-(1H-imidazol-1-yl)phenyl)-3-butenamide

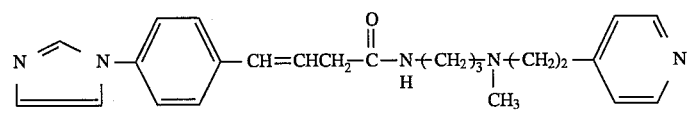

NMR (CDCl₃) δ; 1.5~1.8 (2H, m), 2.22 (3H, s), 2.3~2.8 (6H, m), 3.06 (2H, d, J=5.7 Hz), 3.1~3.5 (2H, m), 6.26 (1H, dt, J=5.7 Hz, 15.8 Hz), 6.51 (1H, d, J=15.8 Hz), 6.7~7.1 (3H, m), 7.1~7.5 (6H, m), 7.78 (1H, s), 8.3~8.5 (2H, m)

Example 6

(E)-N-Methyl-N-[3-((N'-(2-(3,4-dimethoxyphenyl) ethyl)-N'-methyl)amino)propyl]-4-(4-(1H-imidazol-1-yl)phenyl)-3-butenamide

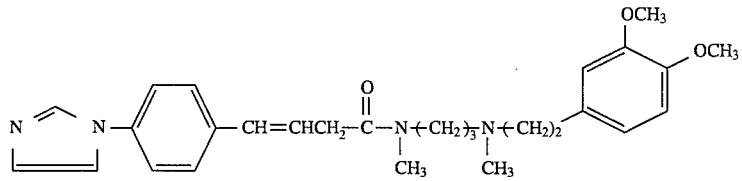

NMR (400 MHz, DMSO-d₆, 150° C.) δ; 1.65~1.75 (2H, m), 2.29 (3H, s), 2.45 (2H, m), 2.60~2.7 (2H, m), 2.70~2.80 (2H, m), 2.94 (3H, bs), 3.30 (2H, dd, J=6.6 Hz, 1.5 Hz), 3.33~3.37 (2H, m), 3.75 (3H, s), 3.77 (3H, s), 6.37 (1H, dt, J=16.1 Hz, 6.6 Hz), 6.52 (1H, dt, J=16.1 Hz, 1.5 Hz), 6.74 (1H, dd, J=8.1 Hz, 2.2 Hz), 6.83 (1H, d, J=2.2 Hz), 6.84 (1H, d, J=8.1 Hz), 7.09 (1H, bs), 7.46~7.55 (4H, m), 7.55~7.57 (1H, m), 8.05 (1H, bs)

Example 7

(E)-N-[3-((N'-(2-(3-Methoxyphenyl)ethyl)-N'-methyl)amino)propyl]-4-(4-1H-imidazol-1-yl)phenyl)-3-butenamide

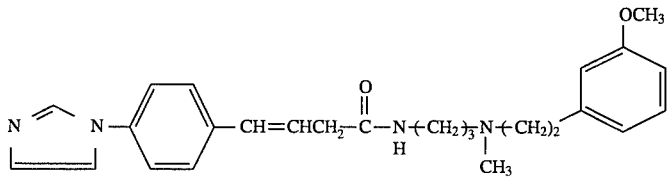

NMR (CDCl₃) δ; 1.5~1.8 (2H, m), 2.20 (3H, s), 2.40~2.81 (6H, m), 3.08 (2H, d, J=6.8 Hz), 3.2~3.5 (2H, m), 3.76 (3H, s), 6.23 (1H, dt, J=6.8 Hz, 16.2 Hz), 6.48 (1H, d, J=16.2 Hz), 6.64~6.80 (4H, m), 7.00~7.48 (7H, m), 7.80 (1H, br)

Example 8

(E)-N-[3-((N'-(2-(4-Methoxyphenyl)ethyl)-N'-methyl)amino)propyl]-4-(4-(1H-imidazol-1-yl)phenyl)-3-butenamide

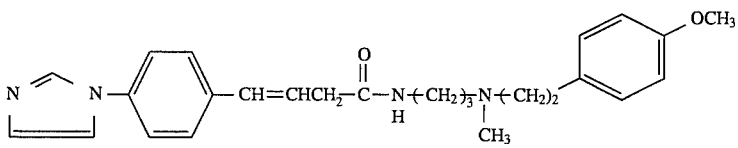

NMR (CDCl₃) δ; 1.44~1.80 (2H, m), 2.20 (3H, s), 2.30~2.80 (6H, m), 3.0 (2H, d, J=7.0 Hz), 3.16~3.40 (2H, m), 3.70 (3H, s), 6.20 (1H, dt, J=7.0 Hz, 16.0 Hz), 6.40 (1H, d, J=16.0 Hz), 6.60~7.5 (11H, m), 7.72 (1H, s)

Example 9

(E)-N-[3-((N'-(2-Phenylethyl)-N'-methyl)amino)propyl]-4-(4-(1H-imidazol-1-yl)phenyl)-3-butenamide

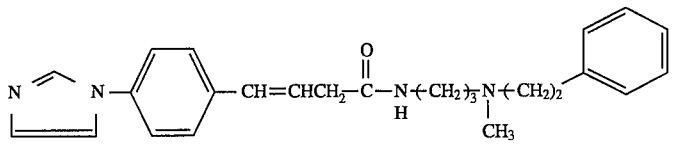

NMR (CDCl$_3$) δ; 1.5~1.9 (2H, m), 2.19 (3H, s), 2.35~2.90 (6H, m), 3.00 (2H, d, J=7.2 Hz), 3.2~3.5 (2H, m), 6.20 (1H, dt, J=7.2 Hz, 16.2 Hz), 6.43 (1H, d, J=16.2 Hz), 6.75~7.65 (12H, m), 7.75 (1H, br)

Example 10

(E)-N-[3-((N'-(2-(3,4,5-Trimethoxyphenyl)ethyl)-N'-methyl)amino)propyl]-4-(4-(1H-imidazol-1-yl)phenyl)-3-butenamide

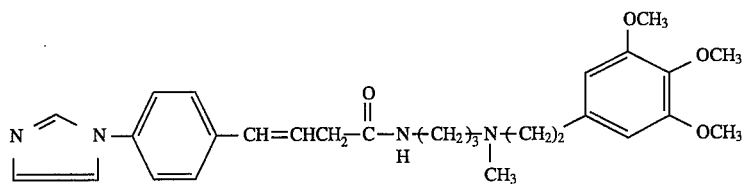

NMR (CDCl$_3$) δ; 1.50~1.84 (2H, m), 2.20 (3H, s), 2.34~2.76 (6H, m), 3.04 (2H, d, J=6.0 Hz), 3.16~3.46 (2H, m), 3.74 (9H, s), 5.96~6.56 (4H, m), 7.04~7.48 (7H, m), 7.72 (1H, s)

Example 11

(E)-N-[3-((N'-(2-(3,4-Diethoxyphenyl)ethyl)-N'-methyl)amino)propyl]-4-(4-(1H-imidazol-1-yl)phenyl)-3-butenamide

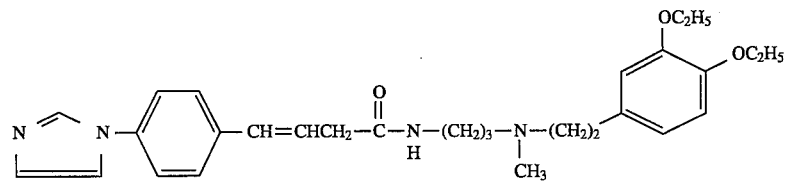

NMR (CDCl$_3$) δ; 1.40 (3H, t, J=7.0 Hz), 1.41 (3H, t, J=7.0 Hz), 1.5~1.8 (2H, m), 2.21 (3H, s), 2.3~2.8 (6H, m), 3.04 (2H, d, J=5.7 Hz), 3.2~3.5 (2H, m), 3.99 (2H, q, J=7.0 Hz), 4.00 (2H, q, J=7.0 Hz), 6.18 (1H, dt, J=5.7 Hz, 15.5 Hz), 6.44 (1H, d, J=15.5 Hz) 6.5~6.8 (3H, m) 7.0~7.5 (7H, m), 7.75 (1H, bs)

Example 12

(E)-N-[3-((N'-(2-(2,5-Dimethoxyphenyl)ethyl)-N'-methyl)amino)propyl]4-(4-(1H-imidazol-1-yl)phenyl)-3-butenamide

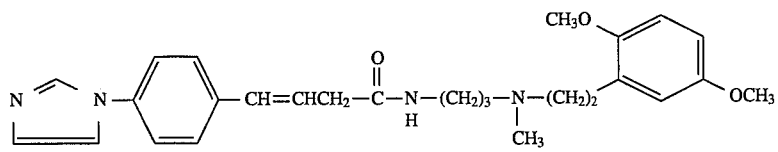

NMR (CDCl₃) δ; 1.50~1.80 (2H, m), 2.20 (3H, s), 2.40~2.80 (6H, m), 3.04 (2H, d, J=5.7 Hz), 3.16~3.44 (2H, m), 3.64 (3H, s), 3.68 (3H, s), 5.90~6.52 (2H, m), 6.52~6.80 (3H, m), 7.04~7.60 (7H, m), 7.72 (1H, s)

Example 13

(E)-N-[3-((N'-(2-(3,4-Methylenedioxyphenyl)ethyl)-N'-methyl)amino)propyl]-4-(4-(1H-imidazol-1-yl)phenyl)-3-butenamide

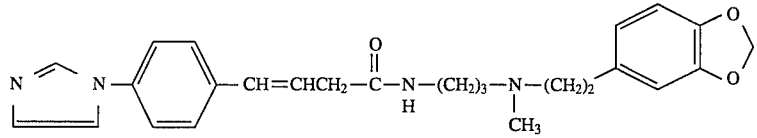

NMR (CDCl₃) δ; 1.45~1.80 (2H, m), 2.16 (3H, s), 2.30~2.70 (6H, m), 3.04 (2H, d, J=5.4 Hz), 3.10~3.40 (2H, m), 5.80 (2H, s), 6.0~6.72 (5H, m), 7.04~7.60 (7H, m), 7.76 (1H, s)

Example 14

(E)-N-[3-((N'-(2-(3,4-Ethylenedioxyphenyl)ethyl)-N'-methyl)amino)propyl]-4-(4-(1H-imidazol-1-yl)phenyl)-3-butenamide

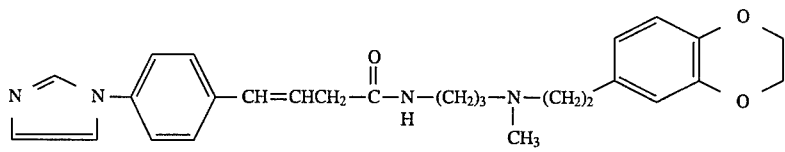

NMR (CDCl₃) δ; 1.5~1.8 (2H, m), 2.18 (3H, s), 2.3~2.7 (6H, s), 3.06 (2H, d, J=6.2 Hz), 3.2~3.5 (2H, m), 4.18 (4H, s), 6.0~6.8 (5H, m), 7.0~7.5 (7H, m), 7.78 (1H, s)

Example 15

(E)-N-[3-((N'-(2-(3,4-Dimethoxyphenyl)ethyl)-N'-methyl)amino)propyl]-4-(3-(1H-imidazol-1-yl)phenyl)-3-butenamide

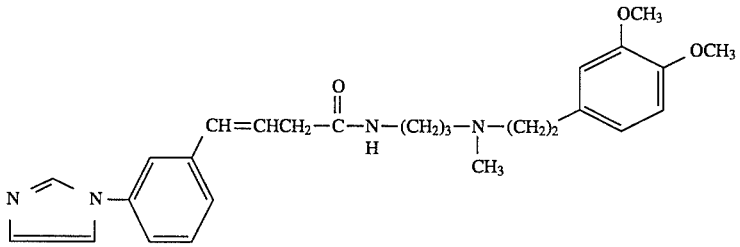

NMR (CDCl₃) δ; 1.5~1.8 (2H, m), 2.21 (3H, s), 2.3~2.8 (6H, m), 3.00 (2H, d, J=6.1 Hz), 3.1~3.5 (2H, m), 3.78 (3H, s), 3.80 (3H, s), 6.26 (1H, dt, J=16.6 Hz, 6.1 Hz), 6.38 (1H, d, J=16.6 Hz), 6.5~6.7 (3H, m), 6.9~7.2 (7H, m), 7.72 (1H, bs)

Example 16

(E)-N-[3-((N'-(2-(3,4-Dimethoxyphenyl)ethyl)-N'-methyl)amino)propyl]-4-(4-(2-methyl-1H-imidazol-1-yl)phenyl)-3-butenamide

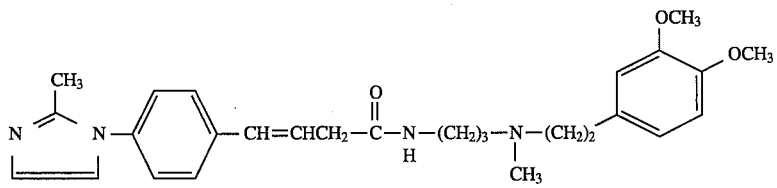

NMR (CDCl₃) δ; 1.5~1.9 (2H, m), 2.23 (3H, s), 2.33 (3H, s), 2.3~2.8 (6H, m), 3.06 (2H, d, J=5.7 Hz), 3.1~3.5 (2H, m), 3.82 (3H, s), 3.85 (3H, s), 6.30 (H, dt, J=5.7 Hz, 15.4 Hz), 6.53 (1H, d, J=15.4 Hz), 6.5~6.8 (3H, m), 6.95 (1H, d, J=1.3 Hz), 7.00 (1H, d, J=1.3 Hz), 7.0~7.2 (2H, m), 7.2~7.5 (3H, m)

Example 17

(E)-N-[3-((N'-(2-(3,4-Dimethoxyphenyl)ethyl)-N'-methyl)amino)propyl]-N-cyclopentyl-4-(4-(2-methyl-1H-imidazol-1-yl)phenyl)-3-butenamide

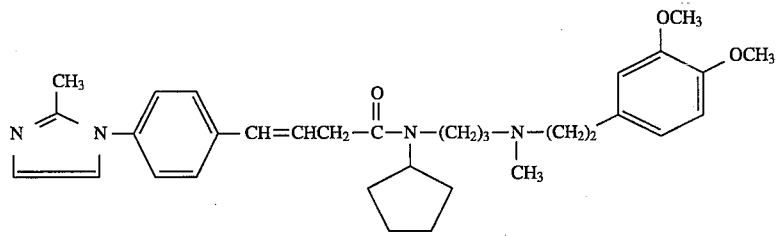

NMR (CDCl₃) δ; 1.20~2.08 (10H, m), 2.31 (3H, s), 2.34 (3H, s), 2.40~2.87 (6H, m), 2.95~3.40 (5H, m), 3.81 (3H, s), 3.84 (3H, s), 6.20~6.50 (2H, m), 6.51~6.80 (3H, m), 6.81~7.00 (2H, m), 7.00~7.20 (2H, m), 7.30~7.50 (2H, m)

Example 18

(E)-N-[3-((N'-(2-(3,4-Dimethoxyphenyl)ethyl)-N'-methyl)amino)propyl]-4-(4-(4-methyl-1H-imidazol-1-yl)phenyl-3-butenamide

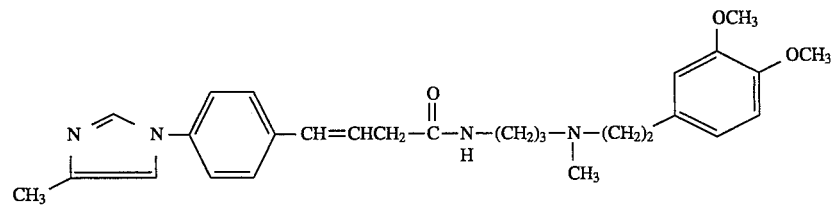

NMR (CDCl₃) δ; 1.5~1.8 (2H, m), 2.20 (3H, s), 2.27 (3H, s), 2.3~2.8 (6H, m), 3.04 (2H, d, J=5.7 Hz), 3.2~3.5 (2H, m), 3.82 (3H, s), 3.84 (3H, s), 6.23 (1H, dt, J=5.7 Hz, 15.8 Hz), 6.49 (1H, d, J=15.8 Hz), 6.96 (1H, d, J=0.9 Hz), 7.1~7.5 (5H, m), 7.67 (1H, d, J=0.9 Hz)

Example 19

(E)-N-[3-((N'-(2-(3,4-Dimethoxyphenyl)ethyl)-N'-methyl)amino)propyl]-4-(4-(3-pyridyl)phenyl)-3-butenamide

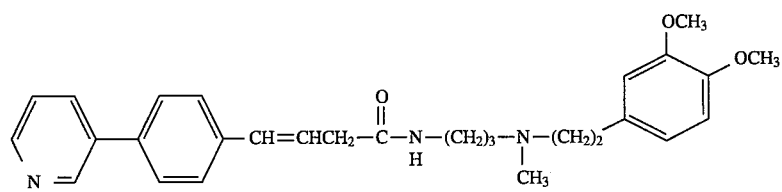

NMR (CDCl$_3$) δ; 1.5~1.7 (2H, m), 2.18 (3H, s), 2.3~2.8 (6H, m), 3.04 (2H, d, J=5.4 Hz) 3.2~3.5 (2H, m), 3.78 (3H, s), 3.80 (3H, s), 6.30 (1H, dt, J=15.8 Hz, 5.4 Hz), 6.44 (1H, d, J=15.8 Hz), 6.5~6.8 (3H, m), 7.2~7.5 (6H, m), 7.76 (1H, dm, J=8.3 Hz), 8.50 (1H, dd, J=5.4 Hz, 2.5 Hz), 8.76 (1H, d, J=2.5 Hz)

Example 20

(E)-N-[3-((N'-(2-(3,4,5-Trimethoxyphenyl)ethyl)-N'-methyl)amino)propyl]-4-(4-(3-pyridyl)phenyl)-3-butenamide

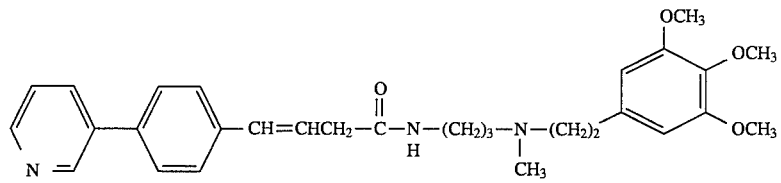

NMR (CDCl$_3$) δ; 1.5~1.8 (2H, m), 2.20 (3H, s), 2.30~2.70 (6H, m), 3.08 (2H, d, J=5.4 Hz), 3.1~3.5 (2H, m), 3.78 (9H, s), 6.30 (2H, s), 6.36 (1H, dt, J=5.4 Hz, 15.8 Hz), 6.46 (1H, d, J=15.8 Hz), 7.1~7.6 (6H, m), 7.75 (1H, d, J=7.2 Hz), 8.5 (1H, bs), 8.75 (1H, bs)

Example 21

(E)-N-[3-((N'-(2-(3,4-Dimethoxyphenyl)ethyl)-N'-methyl)amino)propyl]-4-(4-(2-pyridyl)phenyl)-3-butenamide

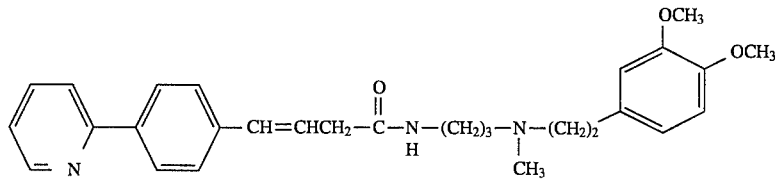

NMR (CDCl$_3$) δ; 1.5~1.9 (2H, m), 2.12 (3H, s), 2.2~2.8 (6H, m), 3.08 (2H, d, J=6.5 Hz), 3.2~3.6 (2H, m), 3.82 (6H, s), 6.34 (1H, dt, J=15.8 Hz, 6.5 Hz), 6.50 (1H, d, J=15.8 Hz), 6.6~6.8 (3H, m), 7.1~7.4 (2H, m), 7.46 (2H, d, J=8.3 Hz), 7.7~7.8 (2H, m), 7.96 (2H, d, J=8.3 Hz), 8.70 (1H, m)

Example 22

(E)-N-[3-((N'-(2-(3,4-Dimethoxyphenyl)ethyl)-N'-methyl)amino)propyl]-4-(4-(4-pyridyl)phenyl)-3-butenamide

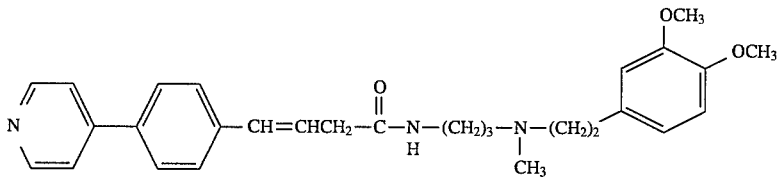

NMR (CDCl$_3$) δ; 1.6~1.9 (2H, m), 2.28 (3H, s), 2.4~2.8 (6H, m), 3.14 (2H, d, J=6.1 Hz), 3.3~3.6 (2H, m), 3.88 (3H, s), 3.90 (3H, s), 6.48 (1H, dt, J=16.6 Hz, 6.1 Hz), 6.60 (1H, d, J=16.6 Hz), 6.6~6.9 (3H, m), 7.3~7.7 (7H, m), 8.71 (2H, m)

Example 23

(E)-N-[3-((N'-(2-(3,4-Dimethoxyphenyl)ethyl)-N'-methyl)amino)propyl]-4-(4-(1H-pyrrol-1-yl)phenyl)-3-butenamide

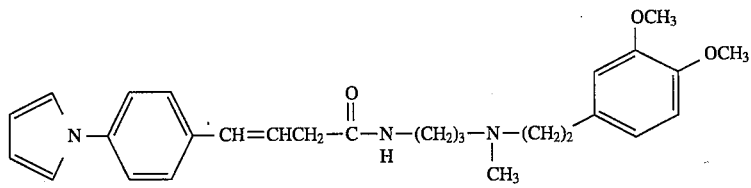

NMR (CDCl₃) δ; 1.48~1.92 (2H, m), 2.19 (3H, s), 2.35~2.80 (6H, m), 3.05 (2H, d, J=6.2 Hz), 3.20~3.60 (2H, m), 3.82 (6H, s), 6.0~6.5 (4H, m), 6.5~6.8 (3H, m), 6.9~7.1 (2H, m), 7.1~7.4 (4H, m)

Example 24

(E)-N-[3-((N'-(2-(3,4-Dimethoxyphenyl)ethyl)-N'-methyl)amino)propyl]-4-(4-(imidazo[1,2-a]pyridin-6-yl)phenyl)-3-butenamide

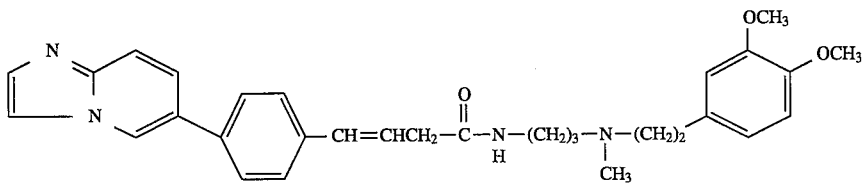

NMR (CDCl₃) δ; 1.6~1.9 (2H, m), 2.23 (3H, s), 2.7~2.8 (6H, m), 3.09 (2H, d, J=6.1 Hz), 3.3~3.5 (2H, m), 3.82 (3H, s), 3.85 (3H, s), 6.36 (1H, dt, J=16.2 Hz, 6.1 Hz), 6.52 (1H, d, J=16.2 Hz), 6.6~6.9 (3H, m), 7.2~7.6 (8H, m), 8.46 (1H, m)

Example 25

(E)-N-[3-((N'-(2-(3,4-Dimethoxyphenyl)ethyl)-N'-methyl)amino)propyl]-4-(4-(1H-1,2,4-triazol-1-yl)phenyl)-3-butenamide

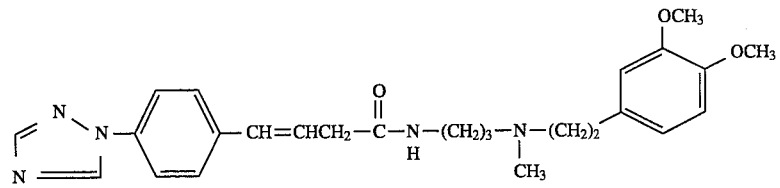

NMR (CDCl₃) δ; 1.50~1.85 (2H, m), 2.20 (3H, s), 2.18~2.80 (6H, m), 3.02 (2H, d, J=6.0 Hz), 3.2~3.5 (2H, m), 3.80 ((3H, s), 3.82 (3H, s), 6.22 (1H, dt, J=6.0 Hz, 16.2 Hz), 6.46 (1H, d, J=16.2 Hz), 6.35~6.78 (3H, m), 7.0~7.3 (1H, m), 7.3~7.6 (4H, m), 8.00 (1H, s), 8.44 (1H, s)

Example 26

(E)-N-[3-((N'-(2-(3,4-Dimethoxyphenyl)ethyl)-N'-methyl)amino)propyl]-4-(4-(1H-benzimidazol-1-yl)phenyl)-3-butenamide

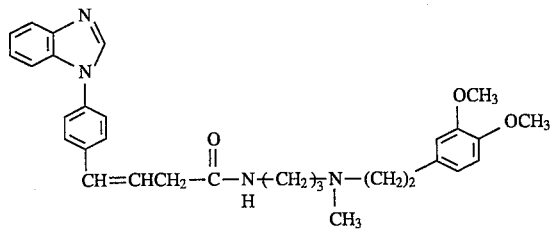

NMR (CDCl$_3$) δ; 1.44~1.80 (2H, m), 2.20 (3H, s), 2.32~2.80 (6H, m), 3.0 (2H, d, J=6.0 Hz), 3.10~3.44 (2H, m), 3.72 (3H, s), 3.76 (3H, s), 6.0~6.44 (2H, m), 6.48~6.76 (3H, m), 7.10~7.6 (9H, m), 8.0 (1H, s)

Example 27

(E)-N-[3-((N'-(2-(3,4-Dimethoxyphenyl)ethyl)-N'-methyl)amino)propyl]-4-(4-(1H-pyrazol-1-yl)phenyl)-3-butenamide

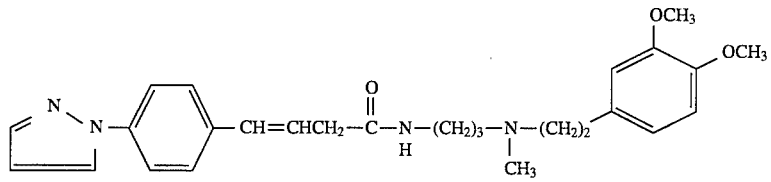

NMR (CDCl$_3$) δ; 1.4~1.8 (2H, m), 2.16 (3H, s), 2.3~2.7 (6H, m), 3.0 (2H, d, J=5.0 Hz), 3.16~3.40 (2H, m), 3.76 (6H, s), 5.96~6.76 (6H, m), 7.2~7.7 (7H, m), 7.8 (1H, d, J=3 Hz)

Example 28

(E)-N-[3-((N'-(2-(3,4-Dimethoxyphenyl)ethyl)-N'-methyl)amino)propyl]-4-(4-(1,3-oxazol-5-yl)phenyl)-3-butenamide

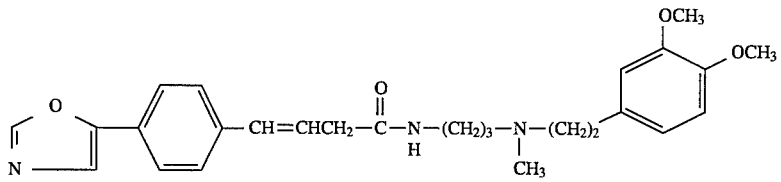

NMR (CDCl$_3$) δ; 1.50~1.86 (2H, m), 2.18 (3H, s), 2.30~2.76 (6H, m), 3.05 (2H, d, J=6.2 Hz), 3.20~3.54 (2H, m), 3.82 (3H, s) 3.84 (3H, s), 6.22 (1H, dt, J=15.1 Hz, 6.2 Hz), 6.44 (1H, d, J=15.1 Hz), 6.56~6.76 (3H, m), 7.28 (1H, s), 7.3~7.66 (5H, m), 7.86 (1H, s)

Example 29

(E)-N-[3-((N'-(2-(3,4-Dimethoxyphenyl)ethyl)-N'-methyl)amino)propyl]-4-(4-(4-(1H)-pyridon-1-yl)phenyl)-3-butenamide

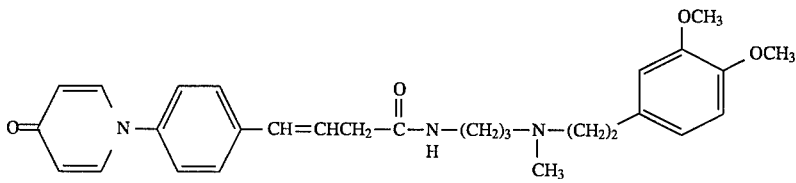

NMR (CDCl$_3$) δ; 1.5~1.8 (2H, m), 2.23 (3H, s), 2.3~2.8 (6H, m), 3.05 (2H, d, J=5.3 Hz), 3.2~3.5 (2H, m), 3.82 (3H, s), 3.84 (3H, s), 6.0~6.5 (4H, m), 6.5~6.8 (3H, m), 7.0~7.6 (7H, m)

Example 30

(E)-N-[3-((N'-(2-(4-Methoxyphenyl)ethyl)-N'-allyl}amino)propyl]-4-(4-(1H-imidazol-1-yl)phenyl)-3-butenamide

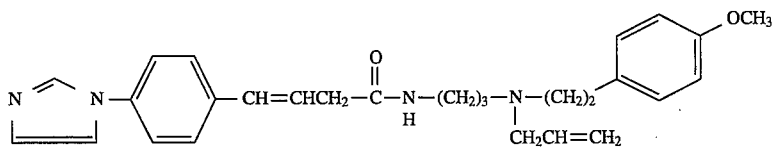

NMR (CDCl₃) δ; 1.50~1.80 (2H, m), 2.4~2.7 (6H, m), 3.04 (2H, d, J=5.0 Hz), 3.03 (2H, d, J=7.2 Hz), 3.16~3.44 (2H, m), 3.7 (3H, s), 4.96~5.24 (2H, m), 5.5~6.0 (1H, m), 6.0~7.5 (13H, m), 7.76 (1H, s)

Example 31

(E)-N-[3-((N'-(2-(3,4-Dimethoxyphenyl)ethyl)amino)propyl]-4-(4-(1H-imidazol-1-yl)phenyl)-3-butenamide

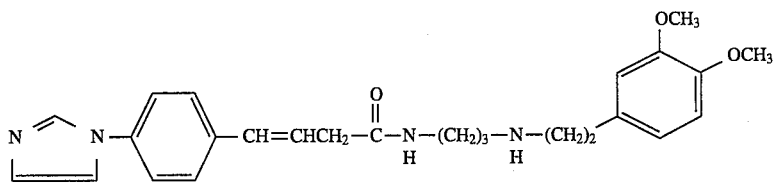

NMR (CDCl₃) δ; 1.5~1.9 (2H, m), 2.32 (1H, brs), 2.50~3.00 (6H, m), 3.08 (2H, d, J=7.0 Hz), 3.2~3.5 (2H, m), 3.84 (3H, s), 3.86 (3H, s), 6.26 (1H, dt, J=7.0 Hz, 14.4 Hz), 6.50 (1H, d, J=14.4 Hz), 6.58~6.80 (3H, m), 7.0~7.55 (7H, m), 7.78 (1H, s)

Example 32

(E)-N-[3-((N'-(2-(3,4-Dimethoxyphenyl)ethyl)-N'-allyl)amino)propyl]-4-(4-(1H-imidazol-1-yl)phenyl)-3-butenamide

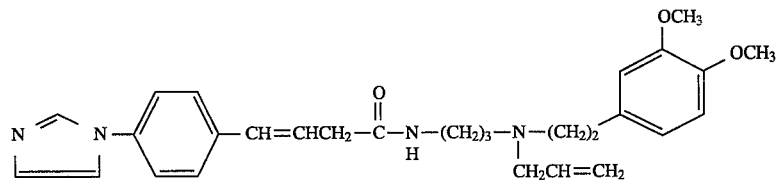

NMR (CDCl₃) δ; 1.55~1.80 (2H, m), 2.30~2.74 (6H, m), 2.80~3.25 (4H, m), 3.2~3.5 (2H, m), 3.74 (6H, s), 4.98~5.18 (2H, m), 6.24 (1H, dt, J=5.4 Hz, 16.2 Hz), 6.47 (1H, d, J=16.2 Hz), 6.62~7.45 (10H, m), 7.78 (1H, s)

Example 33

N-[2-(3,4-Dimethoxyphenyl)ethyl]-3-N'-[(E)-4-(4-(1H-imidazol-1-yl)phenyl)-3-butenoyl]homopiperazine

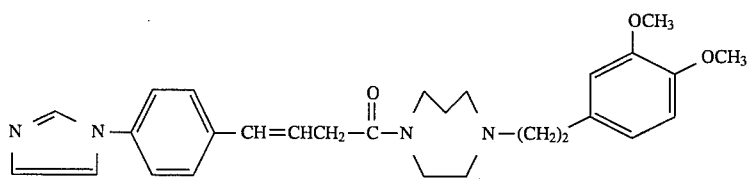

NMR (CDCl₃) δ; 1.73~2.07 (2H, m), 2.41~3.13 (8H, m), 3.21~3.83 (6H, m), 3.83 (3H, s), 3.85 (3H, s), 6.37~6.57 (2H, m), 6.61~6.89 (3H, m), 7.14~7.65 (6H, m), 7.83 (1H, s)

Example 34

(E)-N-[3-((N'-(2-(3,4-Dimethoxyphenyl)ethyl)-N'-methyl)amino)-2-methylpropyl]-4-(4-(1H-imidazol-1-yl)phenyl)-3-butenamide

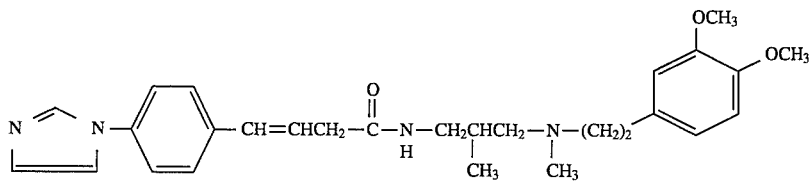

NMR (CDCl₃) δ; 0.84 (3H, d, J=7.0 Hz), 2.16 (3H, s), 2.2~2.8 (7H, m), 3.0 (2H, d, J=6.0 Hz), 3.4~3.8 (2H, m), 3.8 (6H, s), 5.96~6.8 (5H, m), 7.0~7.5 (6H, m), 7.76 (1H, s), 7.8~8.1 (1H, m)

Example 35

(E)-N-[4-((N'-(2-(3,4-Dimethoxyphenyl)ethyl)-N'-methyl)amino)butan-2-yl]-4-(4-(1H-imidazol-1-yl)phenyl)-3-butenamide

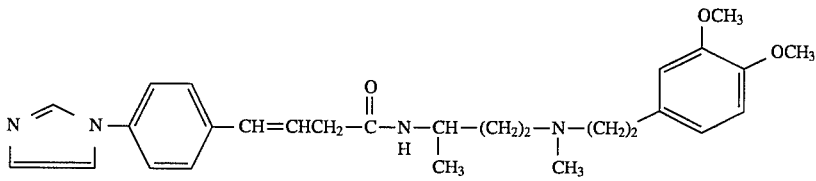

NMR (CDCl₃) δ; 1.16 (3H, d, J=7.0 Hz), 1.4~1.8 (2H, m), 2.2 (3H, s), 2.3~2.8 (6H, m), 3.74 (3H, s), 3.76 (3H, s), 3.9~4.2 (1H, m), 6.0~6.8 (5H, m), 7.04~7.6 (7H, m), 7.74 (1H, s)

Example 36

(E)-N-[4-((N'-(2-(3,5-Dimethoxyphenyl)ethyl)-N'-methyl)amino)butan-2-yl]-4-(4-(1H-imidazol-1-yl)phenyl)-3-butenamide

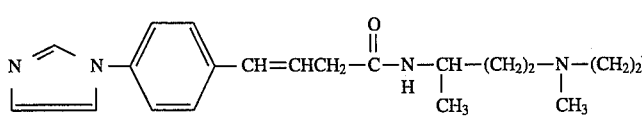

NMR (CDCl₃) δ; 1.18 (3H, d, J=7.2 Hz), 1.4–2.0 (2H, m), 2.21 (3H, s), 2.3–2.8 (6H, m), 3.01 (2H, d, J=6.6 Hz), 3.73 (6H, s), 3.9–4.3 (1H, m), 6.24 (3H, s), 6.27 (1H, dt, J=6.6 Hz, 15.8 Hz), 6.44 (1H, d, J=15.8 Hz), 7.0–7.5 (7H, m), 7.76 (1H, s)

EXAMPLES OF THE COMPOUND II

Manufacturing Example 1

(E)-4-(4-fluorophenyl)-3-butenoic acid

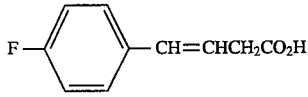

74.4 g of 4-fluorobenzaldehyde and 233.6 g of β-carboxyethyl-triphenyl phosphonium chloride were suspended in 700 ml of tetrahydrofuran and these were incubated on ice and stirred. Into this 500 ml tetrahydrofuran solution of 141.4 g of potassium tert-butoxide was added slowly dropwise. 30 minutes after temperature was brought to room temperature and then they were stirred for 10 hours. After adding thereto ice water and cleaning with ether, the hydrogen-ion concentration of water layer was set to pH2 with undiluted hydrochloric acid. Extraction was then made with ethyl acetate. After drying with magnesium sulfate and concentration made under reduced pressure, the solid obtained was recrystallized from hydrous ethanol, and 53.98 g of marked compound (yield: 50%) was obtained as white needle crystal.

fusing point (°C.): 114 to 115
Value of elemental analysis: as $C_{10}H_9FO_2$

|  | C | H | F |
|---|---|---|---|
| Theoretical value | 66.64 | 5.04 | 10.55 |
| Observed value | 66.64 | 5.02 | 10.44 |

NMR (CDCl₃); δ 3.28 (2H, d, J=6.5 Hz), 6.16 (1H, dt, J=6.5 Hz, 16.2 Hz), 6.50 (1H, d, J=16.2 Hz), 7.2 to 7.5 (4H, m), 9.36 (1H, br)

In a same way as above, the following compound was obtained.

(E)-4-(2-fluorophenyl)-3-butenoic acid

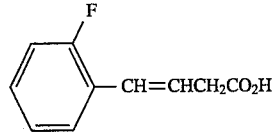

Fusing Point (°C.): 61 to 62
Value of Elemental Analysis: as $C_{10}H_9FO_2$

|  | C | H |
|---|---|---|
| Theoretical Value: | 66.64 | 5.04 |
| Observed Value: | 66.75 | 5.03 |

NMR (CDCl₃) δ; 3.30 (2H, d, J=6.5 Hz), 6.17 (1H, dt, J=6.5 Hz, 16.6 Hz), 6.68 (1H, d, J=16.6 Hz), 6.9–7.4 (4H, m), 11.62 (1H, br)

(E)-4-(3-fluorophenyl)-3-butenoic acid

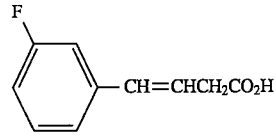

Fusing Point (°C.): 66.5 to 67
Value of Elemental Analysis: as $C_{10}H_9FO_2$

|  | C | H | F |
|---|---|---|---|
| Theoretical Value: | 66.64 | 5.04 | 10.55 |
| Observed Value: | 66.66 | 4.95 | 10.51 |

NMR (CDCl₃) δ; 3.28 (2H, d, J=6.5 Hz), 6.24 (1H, dt, J=6.5 Hz, 16.2 Hz), 6.50 (1H, d, J=16.2 Hz), 7.7–8.4 (4H, m), 11.92 (1H, br)

(E)-4-(4-(methylthio)phenyl)-3-butenoic acid

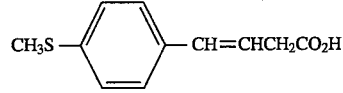

Fusing Point (°C.): 131 to 132
Value of Elemental Analysis: as $C_{11}H_{12}O_2S$

|  | C | H | S |
|---|---|---|---|
| Theoretical Value: | 63.43 | 5.81 | 15.40 (%) |
| Observed Value: | 63.78 | 5.78 | 15.34 (%) |

NMR (CDCl₃) δ; 2.47 (3H, s), 3.28 (2H, d, J=6 Hz), 6.16 (1H, dt, J=7 Hz, 15 Hz), 6.44 (1H, d, J=15 Hz), 7.01–7.35 (4H, m)

(E)-4-(4-cyanophenyl-3-butenoic acid

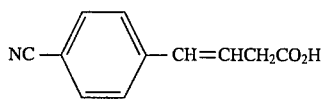

Fusing Point (°C.): 111 to 113
Value of Elemental Analysis: as $C_{11}H_9NO_2$

|  | C | H | N |
|---|---|---|---|
| Theoretical Value (%): | 70.58 | 4.85 | 7.48 |
| Observed Value (%): | 70.61 | 4.96 | 7.41 |

NMR (CDCl$_3$) δ; 3.29 (2H, d, J=5.7 Hz), 6.34 (1H, dt, J=5.7 Hz, 15.8 Hz), 6.58 (1H, d, J=15.8 Hz), 7.3~7.7 (4H, m), 9.84 (1H, br)

*(E)-4-(4-chlorophenyl-3-butenoic acid

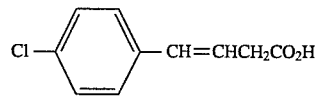

Fusing Point (°C.): 118.5 to 110
Value of Elemental Analysis: as $C_{10}H_9Cl_2$

|  | C | H |
|---|---|---|
| Theoretical Value (%): | 61.08 | 4.61 |
| Observed Value (%): | 61.12 | 4.67 |

NMR (CDCl$_3$) δ; 3.28 (2H, d, J=6.0Hz), 6.19 (1H, dt, J=6.0 Hz, 16.2Hz), 6.49 (1H, d, J=16.2Hz), 7.1~7.4 (4H, m), 11.32 (1 H, br).

*(E)-4-(2-methoxyphenyl)-3-butenoic acid

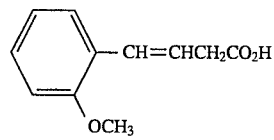

NMR (CDCl$_3$) δ 3.31 (2H,dd,J=1.0Hz,7.0Hz) 3.86 (3H,S) 6.27 (1H,dt,J=7.0Hz, 16.3Hz) 6.7~7.5 (5H,m) 1075 (1H,br).

*(E)-4-(3-methoxyphenyl-3-butenoic acid

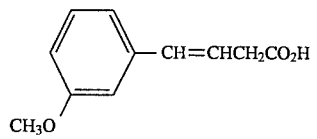

Fusing Point (°C.): 96.5–97.5
Value of Elemental Analysis: as $C_{11}H_{12}O_3$,

|  | C | H |
|---|---|---|
| Theoretical Value (%) | 68.74 | 6.29 |

|  | C | H |
|---|---|---|
| Observed Value (%) | 68.92 | 6.23 |

NMR (CDCl$_3$) δ; 3.29 (2H, d, J=5.7Hz), 3.80 (3H, s), 6.28 (1H, dt, J=5.7Hz, 15.8Hz), 6.45 (2H, d, J=15.8Hz), 6.7~7.3 (4H, m), 9.8 (1H, bs).

*(E)-4-(4-methoxyphenyl)-3-butenoic acid

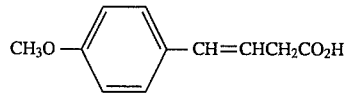

Fusing Point (°C.): 102.5–104.5
Value of Elemental Analysis: As $C_{11}H_{12}O_3$

|  | C | H |
|---|---|---|
| Theoretical Value (%) | 68.73 | 6.30 |
| Observed Value (%) | 68.84 | 6.20 |

NMR (CDCl$_3$) δ; 3.26 (2H, d, J=6.8Hz), 3.78 (3H, s), 6.10 (1H, dt, J=6.8Hz, 16.6Hz), 6.45 (1H, d, J=16.6Hz), 6.83 (2H, d, J=8.6Hz), 7.30 (2H, d, J=8.6Hz), 11.26 (1H, br).

*(E)-4-(4-methylphenyl-3-butenoic acid

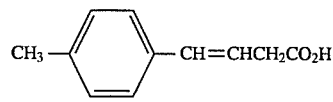

Fusing Point (°C.): 113–114
Value of Elemental Analysis: as $C_{11}H_{12}O_2$

|  | C | H |
|---|---|---|
| Theoretical Value (%): | 74.97 | 6.87 |
| Observed Value (%): | 74.94 | 6.87 |

NMR (CDCl$_3$) δ; 2.32 (3H, s), 3.27 (2H, d, J=7.2Hz), 6.18 (1H, dt, J=7.2Hz, 16.2Hz), 6.49 (1H, d, J=16.2Hz), 7.0–7.4 (4H, m), 11.0 (1H, br).

*(E)-4-(3,4-difluorophenyl)-3-butenoic acid

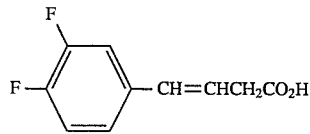

Fusing Point (°C.): 95–96
Value of Elemental Analysis: As $C_{10}H_8F_2O_2$

|  | C | H |
|---|---|---|
| Theoretical Value (%) | 60.61 | 4.07 |
| Observed Value (%) | 60.85 | 4.02 |

NMR (CDCl$_3$) δ; 3.28 (2H, d, J=8Hz), 6.10 (1H,dt,J=8Hz, 16Hz), 6.24 (1H,d,J=16Hz), 6.9–7.3 (3H,m).

*(E)-4-(3,4-dimethoxyphenyl-3-butenoic acid

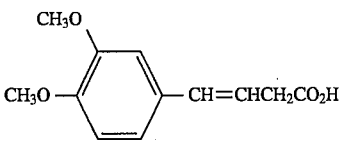

NMR (CDCl$_3$) δ; 3.24 (2H, d, J=6.5Hz). 3.82 (3H, s), 3.84 (3H, s), 6.06 (1H, dt, J=6.5Hz, 16.2Hz), 6.40 (1H, d, J=16.2Hz), 6.8–7.0 (3H, 8.40 (1H, br).

*(E)-4-(3,4-methylenedioxyphenyl)-3-butenoic acid

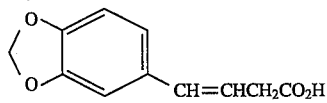

Fusing Point (°C.): 114–115
Value of Elemental Analysis: As C$_{11}$H$_{10}$C$_4$

|  | C | H |
| --- | --- | --- |
| Theoretical Value (%) | 64.07 | 4.89 |
| Observed Value (%) | 64.28 | 4.95 |

NMR (CDCl$_3$) δ; 3.22(2H,d,J=8Hz), 5.90(2H ,S), 6.00(1H, dt, J=8Hz, 16Hz), 6.36(1H,d,J=16Hz), 6.6–6.9(3H, m).

*(E)-4-(3,4-methylenedioxy)phenyl-3-butenoic acid

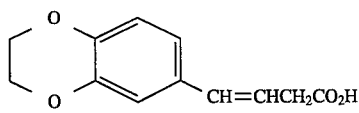

Fusing Point (°C.): 114–115
Value of Elemental Analysis: as C$_{11}$H$_{10}$C$_4$

|  | C | H |
| --- | --- | --- |
| Theoretical Value (%): | 65.44 | 5.49 |
| Observed Value (%): | 65.56 | 5.61 |

NMR (CDCl$_3$) δ; 3.20 (2H, d, J=8Hz), 4.18 (4H,S), 6.00 (1H,dt,J=8Hz, 16Hz), 6.32 (1H, d, J=16Hz), 6.6–6.9 (3H,m).

*(E)-4-(3,4-dichlorophenyl)-3-butenoic acid

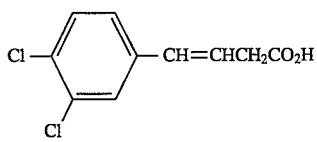

Fusing Point (°C.): 77–78
Value of Elemental Analysis: As C$_{10}$H$_8$Cl$_2$

|  | C | H | Cl |
| --- | --- | --- | --- |
| Theoretical Value (%) | 51.98 | 3.49 | 30.68 |
| Observed Value (%) | 52.21 | 3.47 | 30.57 |

NMR (CDCl$_3$) δ; 3.30 (2H, d, J=6.5Hz), 6.26 (1H, dt, J=6.5 Hz, 15.8Hz), 7.1–7.5 (3H, m), 9.8 (1H, br).

*(E)-4-(3,4,5-trimethoxyhenyl)-butenoic acid

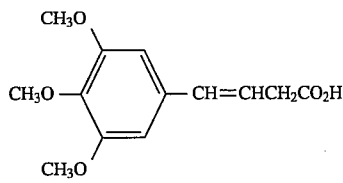

Fusing Point (°C.): 85–87
Value of Elemental Analysis: as C$_{13}$H$_{14}$C$_5$

|  | C | H |
| --- | --- | --- |
| Theoretical Value (%): | 61.89 | 6.39 |
| Observed Value (%): | 61.90 | 6.33 |

NMR (CDCR) δ; 3.26 (2H,d,J=8Hz), 3.80 (3H,S), 3.84 (6H,S), 6.08 (1H,dt,J=8Hz, 16Hz), 6.44 (1H,d,J=16Hz), 6.56 (2H,S).

*(E)-4-(4-dimethylamino)phenyl)-3-butenoic

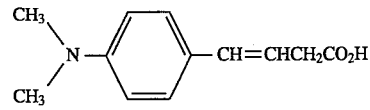

Fusing Point (°C.): 203–204
Value of Elemental Analysis: As C$_{12}$H$_{15}$O$_2$N

|  | C | H | N |
| --- | --- | --- | --- |
| Theoretical Value (%) | 70.22 | 7.37 | 6.82 |
| Observed Value (%) | 70.36 | 7.21 | 6.73 |

NMR (CDCl$_3$) δ; 2.94 (6H, s), 3.25 (2H, d, J=7Hz). 6.00 (1H, dt, J=7Hz, 16Hz). 8.40 (1H, d, J=16Hz), 6.55–8.75 (2H, m), 7.16–7.35 (2H, m).

*(E)-4-(4-(acetylamino)phenyl)-3-butenoic acid

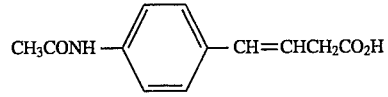

Fusing Point (°C.): 216–217
Value of Elemental Analysis: as C$_{12}$H$_{13}$C$_3$N

|  | C | H | N |
| --- | --- | --- | --- |
| Theoretical Value (%): | 65.74 | 5.98 | 6.39 |
| Observed Value (%): | 65.89 | 5.93 | 6.24 |

NMR (DMSO) δ; 2.02 (3H, s), 3.13 (2H, d, J=6Hz), 6.12 (1H, dt, J=6Hz, 16Hz), 6.40 (1H, d, J=16Hz), 7.14~7.60 (4H, m).

*(E)-4-(4-(methoxycarbony)phenyl)-3-butenoic acid

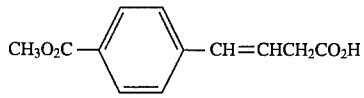

Fusing Point (°C.): 118.5–121
Value of Elemental Analysis: As $C_{12}H_{12}O_4$

|  | C | H |
| --- | --- | --- |
| Theoretical Value (%) | 65.44 | 5.49 |
| Observed Value (%) | 65.65 | 5.42 |

NMR (CDCl$_3$) δ; 3.30(2H, d, J=6.1Hz), 3.88 (3H, s), 6.33 (1H, dt, J=6.1Hz, 15.5Hz), 6.56 (1H, d, J=15.5Hz), 7.3~7.5 (2H, m), 7.8~8.1 (2H, m), 9.45 (1H, br).

*(E)-4-(4-(carbamoyl)phenyl)-3-butenoic acid

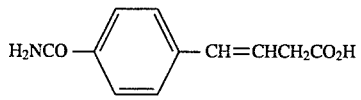

Fusing Point (°C.): 247–249
Value of Elemental Analysis: as $C_{11}H_{11}NO_3$

|  | C | H | N |
| --- | --- | --- | --- |
| Theoretical Value (%): | 64.38 | 5.40 | 6.83 |
| Observed Value (%): | 64.54 | 5.38 | 6.78 |

NMR (DMSO-d$_6$) δ; 3.20 (2H, d, J=5.8Hz), 6.34 (1H, dt, J=5.8 Hz, 15.8Hz), 6.66 (1H, d, J=15.8Hz). 7.1~7.6 (3H, m), 7.6~8.1 (3H.

*(E)-4-((2-isopropyloxy-4-methoxy-3-methyl)phenyl)-3-butenoic acid

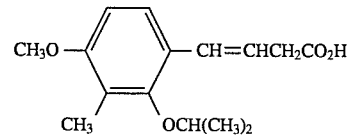

Fusing Point (°C.): 116–117
Value of Elemental Analysis: As $C_{15}H_{20}O_4$

|  | C | H |
| --- | --- | --- |
| Theoretical Value (%) | 68.16 | 7.63 |
| Observed Value (%) | 68.22 | 7.68 |

NMR (CDCl$_3$) δ; 1.26 (6H, d, J=7Hz), 2.12 (3H, s), 3.26 (2H, dd, J=1Hz, 6Hz), 3.80 (3H, s), 4.10 (1H. heptet, J=7Hz), 6.06 (1H, dt, J=6Hz, 17Hz), 6.54 (1H, d, J=9Hz), 6.68 (1H, d, J=17Hz), 7.22(1H, d, J=9Hz), 8.40(1H, br).

Manufacturing Examples 2

N-(2-(N'-methyl-N'-(2-(3,4-dimethoxyphenyl)ethyl)amino)ethyl)phthalimide

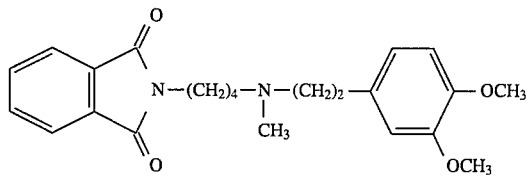

8.08 g of hydroiodic acid of N-methyl-(2-((3,4-dimethoxyphenyl))ethyl)amine, 8.46 g of N-(4-bromobutyl)phthalimide, 8.29 g of potassium carbonate and 50 ml of N,N'-dimethylformamide were mixed and the mixture was stirred at 80° C. for 4 hours. After completion of reaction the mixture was diluted with water and extracted with chloroform. After drying with sulfuric anhydride of magnesium, it was filtered and the solvent was distilled out. The residue was purified by means of silica gel column chromatography (solvent; chloroform:methanol=100:1) and 9.44 g of the marked compouond (yield: 95%) was obtained as yellowish oily matter. NMR (CDCl$_3$) δ; 1.3~1.9 (4H,m), 2.2~2.9 (9H,m) 3.65 (2H, t, J=6.8Hz), 3.78 (3H,S), 3.81 (3H,S) 6.5~6.9 (3H,m), 7.5~7.9 (4H, m).

Manufacturing Examples 3

N-methyl-N-(2-(3,4-dimethoxyphenyl)ethyl)-1,4-butandediamine

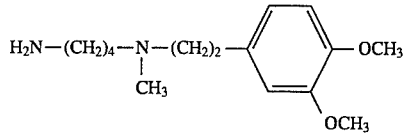

9.44 g of N-(4-(N'-methyl-N'-(3,4-dimethoxyphenyl) ethyl)amino)butyl)phthalimide as obtained in the manufacturing example 2 and 1.27 ml of monohydrate of hydrazine were dissolved into 50 ml of methanol and the solution was refluxed with heat for 2 hours. After cooling down to room temperature, the deposit was filtered and the methanol was distilled off. To this was added aqueous solution of caustic soda and extraction was made with chloroform; then dried up with potassium carbonate ahhydride. The solvent was distilled off and the residue was purified by means of silica gel column chromatography (solvent; chloroform:methanol:non-diluted aqueous ammonia=100:10:1) and 5.21 g of the marked compound (yield: 82%) was obtained as yellowish oily matter.
NMR (CDCl$_3$) δ; 1.3~1.8 (4H, m), 2.2~2.9 (11H, m) 3.26 (2H, bs) 3.84 (3H,S) 3.87 (3H,s), 6.5~6.9 (3H, m).

The below shown compound was obtained in the same way as shown above. N-methyl-N-(2-(3,4-dimethoxyphenyl)ethyl)-1,2-ethylenediamine (yellow oil), N-(3-aminopropyl)-3-(3,4-dimethoxyphenyl)pyrrolidine (yellow oil) and N-isopropyl-N-(2-phenylethyl)-1,3-propanediamine (yellow oil). They have the following formulae, respectively. Results of NMR analysis are shown, respectively.

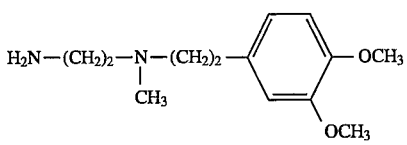

NMR (CDCl₃) δ; 1.75 (2H), bs), 2.1~2.9 (11H, m), 3.85 (3H,s), 3.87 (3H,s), 6.5~6.8 (3H,m).

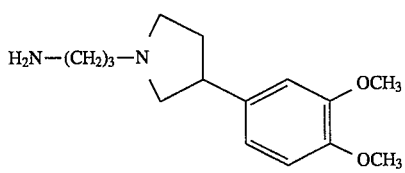

NMR (CDCl₃—CD₃OD) δ; 1.5~3.5 (15H,m), 3.83 (3H, s), 3.86 (3H,s), 6.76 (3H,s).

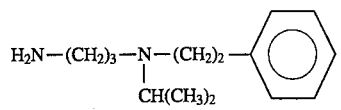

NMR (CDCl₃) δ; 0.98 (3H.d. J=7 Hz), 1.04 (3H.d. J=7 Hz), 1.5–1.8 (2H,m), 2.1–3.4 (11H,m), 6.9–7.4 (5H,m).

Manufacturing Example 4

N-methyl-N-(2-(3,4-dimethoxyphenyl)ethyl)-N'-isopropyl-1,3-propanediamine

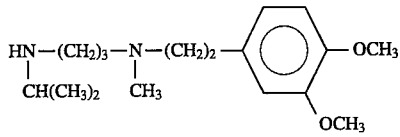

3.87 g of N-methyl-N-(2-(3,4-dimethoxyphenyl)ethyl)-1, 3-propanediamine and 15 ml of acetone were dissolved into 50 ml of ethanol. To this was added 0.1 g of platinum oxide and then hydrogenetion was made at room temperature and under pressure of 3 kg/cm². At the end of 3 hours catalyst was concentrated after filtering and 4.52 g of marked compound was obtained as yellow oily matter (yield: 100%).

NMR (CDCl₃) δ; 1.06 (3H,d,J=7Hz), 1.5–1.9 (2H,m), 2.2–2.9 (13H, m), 3.83 (3H, 5) 3.86 (3H,s), 6.6–6.9 (3H,m).

Manufacturing Example 5

(E)-N-(3-chloropropyl)-3-(4-fluorobenzilidene-2-pyrrolidinone

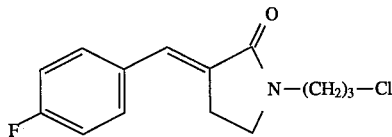

0.96 g of 60% sodium hydroxide, 2.58 ml of 1-chloro-3-iodopropane and 20 ml of N,N-dimethylformamide were mixed and the moxture was stirred at room temperature. To which 3.82 g of (E)-3-(4-fluorobenzilidene)-2-pyrrolidinone dissolved into 20 ml of N,N-dimethylformamide was added dropwise and stirred for 3 hours. After completion of reaction, the product was put into ice water and extracted with ethyl acetate. After water washing, it was dried up with magnesium or sulfuric anhydride and the solvent was distilled off. The residue was purified by means of silica gel column chromatography (solvent n-hexane:ethyl acetate= 3:2) and 3.55 g of the marked compound (yield: 66%) was obtained as white solid matter.

NMR (CDCl₃) δ; 1.9–2.3 (2H, m), 2.9–3.2 (2H, m), 3.7 (6H, m), 6.9–7.6 (5H, m).

By the same method as above, the following compound was obtained

*(E)-N-(3-chloropropyl)-3-(3,4-(methylenedioxy)benzilidene-2-pyrrolidinone

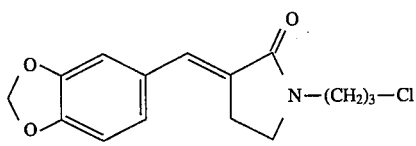

Yellowish solid matter

NMR (CDCl₃) δ; 1.9–2.3 (2H, m), 2.9–3.2 (2H, m), 3.4–3.7 (6H, m), 5.99 (2H, s), 6.7–7.1 (3H, m), 7.1–7.3 (1H, m).

*(E)-N-(3-chloropropyl-3-(4-cyanobenzilidene)-2-pyrrolidinone

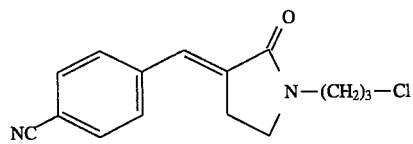

NMR (CDCl₃) δ; 1.9–2.3 (2H, m), 2.9–3.2 (2H, m), 3.4–3.8 (6H, m), 7.2–7.4 (1H, m), 7.4–7.8 (4H, m).

Manufacturing Example 6

(E)-N-(3-chloropropyl)-3-(4-fluorophenyl)propeneamide

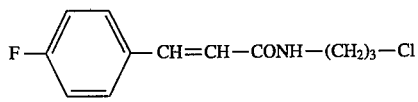

Mixture of 4.15 g of 3-(4-fluorophenyl) propylenic acid, 2.37 ml thyonyl chloride and 20 ml of benzene was refluxed with heat for 3 hours. After concentration under reduced pressure, a coarse acid chloride was obtained. It was then dissolved into 20 ml of dichlormethane and the dissolved was added dropwise under incubation on ice into a mixture of 4.23 g of 3-chloropropylamine hydrochloric acid, 10.47 ml of N,N-diisopropylethylamine and 50 ml of dichlormethane. At the end of 1 hour, it was concentrated under reduced pressure. After dilution with water, extraction was effectuated with ethyl acetate. This was washed with diluted hydrochloric acid and saturated aqueous sodium bicarbonate, and then dried with magnesium of sulfuric anhydride. The solvent was distilled off and the residue was purified by silica gel column chromatography (solvent; n-hexane:ethyl acetate=3:2) and 5.73 g of the marked compound (yield: 95%) was obtained as white solid.

NMR (CDCl$_3$) δ; 1.9~2.3 (2H, m), 3.3~3.7 (4H, m), 6.20 (1H, br), 6.32 (1H, d, J=15.8Hz), 6.8~7.1 (2H, m), 7.2~7.7 (3H, m).

Working Example 1

(E)-N-(3-(N'-(2-(2,3-dimethoxyphenyl)ethyl-N'-methyl)amino)propyl)-4-(4-fluorophenyl)-3-butenamide

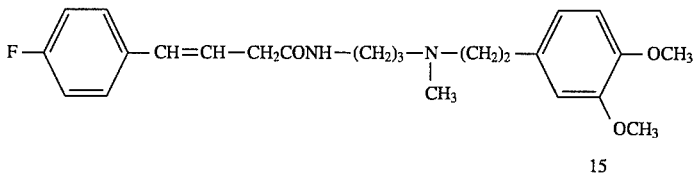

A mixture of 30.0 g of (E)-4-(4-fluorophenyl)-3-butenoic acid, 14.6 ml of thyonyl chloride and 350 ml of benzene was refluxed with heat for 2 hours. Concentration under reduced pressure gave a coarse acid chloride. It was dissolved into 200 ml of dichlormethane and the dissolved was then added dropwise, under incubation on ice, into a mixture of 47.1 g of N-methyl-N-(2-(3,4-dimethoxyphenyl)ethyl-1,3-propanediamine, 26.3 g of potassium carbonate anhydride and 400 ml of dichlormethane. After 30 minutes the temperature was lowered down to room temperature and the mixture was stirred for 30 minutes. After completion of reaction water was added, extraction was made with chloroform and drying applied with sulfuric anhydride of sodium. The solvent was distilled off and the residue was purified by means of silica gel column chromatography (solvent; chloroform:methanol=25:1) and 55.3 g of the marked compound (yoeld: 79%) was obtained as yellow oily matter.

NMR (CDCl$_3$) δ; 1.5~1.8 (2H,m), 2.18 (3H,s), 2.3~2.8 (6H,m), 3.04 (2H,d,J=6.8 Hz), 3.2~3.5 (2H,m), 3.84 (3H,s), 3.86 (3H,s), 6.12 (1H,dt,J=6.8Hz,15.2Hz), 6.48 (1H,d,J=15.2Hz), 7.6~7.8 (3H,m), 7.8~8.1 (2H,m), 8.1~8.4 (3H,m).

Working Example 2

(E)-N-(3-((N'-(2-(3,4-dimethoxyphenyl)ethyl)-N'-methyl)amino)propyl))-4-(4-fluorophenyl)-3-butenamid-dihydrochloride

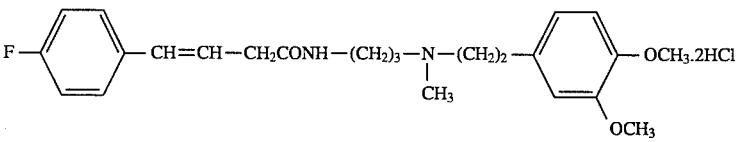

55.3 g of (E)-N-(3-((N'-(2-(3,4-dimethoxyphenyl)ethyl)-N'-methyl)amino)propyl))-4-(4-fluorophenyl)-3-butenamide as obtained under the working example 1 was dissolved into 100 ml of methanol, to which was added methanolhydrogen chloride. Further ether was added thererto to crystallize and 56.1 g of marked compound was obtained (yield: 86%) as slightly yellow powder.

Fusing Point (°C.): 101

Value of Elemental Analysis: as C$_{24}$H$_{33}$FCl$_2$N$_2$O$_3$

|  | C | H | N | F |
|---|---|---|---|---|
| Theoretical Value | 59.13 | 6.82 | 5.75 | 3.89 (%) |
| Observed Value | 59.13 | 6.83 | 5.60 | 3.91 (%) |

Working Examples 3–69

The following compounds were produced by the same method as the working example 1 above

Working Example 3

(E)-N-((3-((N'-(2-(3,4-dimethoxyphenyl)ethyl)methyl)amino)propyl))-3-phenylpropaneamide

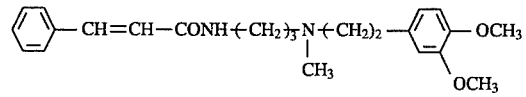

Yellow oily matter

NMR (CDCl$_3$) δ; 1.5~1.9 (2H, m), 2.31 (3H, s), 2.4~2.8 (6H, m), 3.5~3.6 (2H, m), 3.76 (3H, s), 3.84 (3H, s), 6.18 (1H, d, J=16Hz), 6.6~6.8 (3H, m), 6.6~6.8 (3H, m), 7.0~7.6 (7H, m).

Working Example 4

(E)-N-(((3-((N'-(2-(3,4-dimethoxyphenyl)ethyl)-N'-methyl)amino)propyl)))-3-(3,4-dimethoxyphenyl)propeneamide

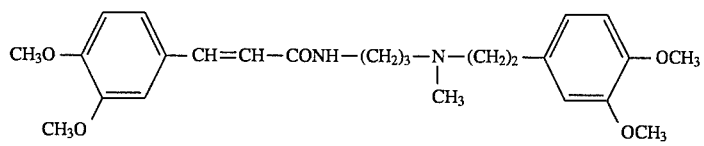

Yellow oily matter
NMR (CD$_3$OD) δ; 1.6~2.0 (2H, m), 2.29 (3H, s), 2.3~2.8 (6H, m); 3.2~3.5 (2H, m), 3.76 (3H, s), 3.78 (3H, s), 3.81 (6H, s), 6.44 (1H, d, J=16 Hz). 6.7~7.2 (6H, m), 7.50 (1H, d, J=16Hz).

Working Example 5

(E)-N-((3-((N'-(2-(3-4-dimethoxyphenyl)ethyl)-N'-methyl)amino)propyl))-3-(2,6-dichlorophenylpropeneamide

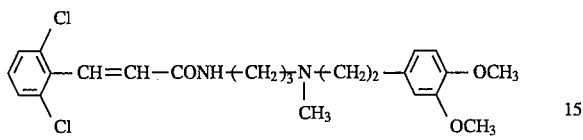

Yellow oily matter
NMR (CDCl$_3$) δ; 1.6~2.0 (2H, m), 2.42 (3H, s), 2.6~2.9 (6H, m), 3.3~3.6 (2H, m), 3.80 (3H, s), 3.84 (3H, s), 6.40 (1H, d, J=18Hz), 6.6~6.8 (3H, m), 6.9~7.8 (5H, m).

Working Example 6

(E)-N-(((3-((N'-(2-(3,4-dimethoxyphenyl)ethyl)-N'-methyl)amino)propyl)))-3-(2,5-dimethoxyphenyl)propeneamide

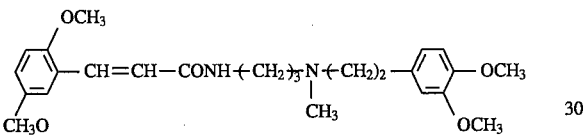

Yellow oily matter
NMR (CDCl$_3$) δ; 1.5~1.9 (2H, m), 2.30 (3H, s), 2.4~2.8 (6H, m), 3.2~3.5 (2H, m), 3.72 (3H, s), 3.76 (3H, s), 3.78 (3H, s), 3.80 (3H, s), 6.30 (1H, d, J=18Hz), 6.6~7.3 (8H, m), 7.7 (1H, d, J=18Hz).

Working Example 7

(E)-N-((3-((N'-(2-(3,4-dimethoxyphenyl)ethyl)-N'-methyl)amino)propyl))-3-(4-fluorophenyl)propeneamide

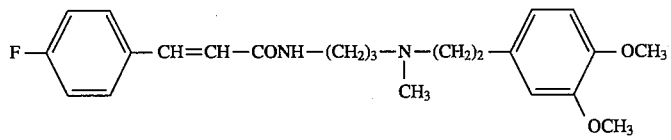

Light yellowish oily matter
NMR (CDCl$_3$) δ; 1.5~1.9 (2H, m), 2.28 (3H, s), 2.3~2.8 (8H, m), 3.3~3.6 (2H, m), 3.72 (3H, s), 3.80 (3H, s), 6.12 (1H, d, J=18Hz), 6.72 (3H, s), 8.8~7.6 (6H, m).

Working Example 8

(E)-N-(((3-((N'-(2-(3,4-dimethoxyphenyl)ethyl)-N'-methyl)amino)propyl)))-3-(3-fluorophenyl)propeneamide

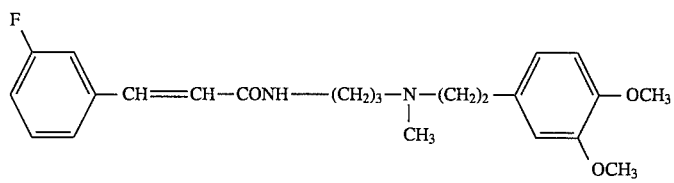

Yellow oily matter
NMR (CDCl$_3$) δ; 1.6~1.9 (2H, m), 2.34 (3H, s), 2.4~2.9 (6H, m), 3.3~3.6 (2H, m), 3.72 (3H, s), 3.81 (3H, s), 6.09(1H, d, J=14Hz), 6.6~6.8 (3H, m), 6.8~7.6 (6H, m).

Working Example 9

(E)-N-((3-((N'-(2-(3,4-dimethoxyphenyl)ethyl)-N'-methyl)amino)propyl))-3-(4-cyanophenyl)propeneamide

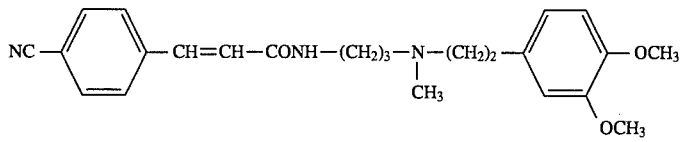

Light yellowish oily matter
NMR (CDCl$_3$) δ; 1.6~2.0 (2H, m), 2.30 (3H, s), 2.4~3.0 (6H, m), 3.3~3.6 (2H, m), 3.72 (3H, s), 3.84 (3H, s), 6.14 (1H, d, J=18Hz), 6.72 (3H, s), 7.2~7.9 (6H,m).

Working Example 10

(E)-N-(((3-((N'-(2-(3,4-dimethoxyphenyl)ethyl)-N'-methyl)amino)propyl)))-3-(3-cyanophenyl)propeneamide

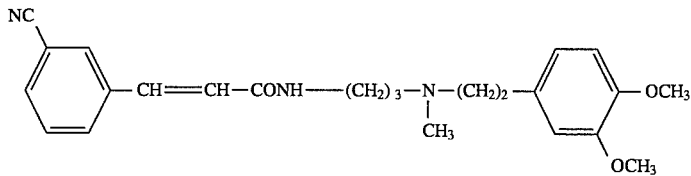

Yellow oily matter
NMR (CDCl$_3$) δ; 1.6~1.9 (2H, m), 2.30 (3H, s), 2.4~2.8 (6H, m), 3.3~3.6 (2H, m), 3.69 (3H, s), 3.81 (3H, s), 6.20 (1H, d, J=18Hz), 6.68 (3H, s), 7.1~7.7 (6H, m).

Working Example 11

(E)-N-((3-((N'-(2-(3,4-dimethoxyphenyl)ethyl)-N'-methyl)amino)propyl))-4-(3-cyanophenyl)-3-buteneamide

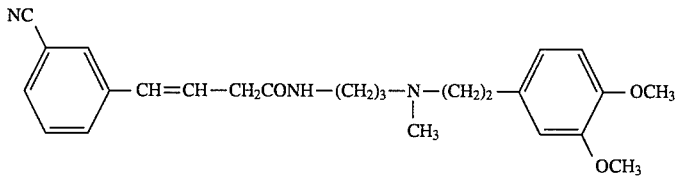

Brown oily matter
NMR (CDCl$_3$) δ; 1.5~1.9 (2H, 2.14 (3H, s), 2.4~2.8 (6H, m), 3.02 (2H, d, J=6.8Hz), 3.2~3.5 (2H, m), 3.84 (3H, s), 3.86 (3H, s), 6.1~6.9 (5H, m), 7.1~7.7 (5H, m).

Working Example 12

(E)-N-(((3-((N'-(2-(3,4-dimethoxyphenyl)ethyl)-N'-methyl)amino)propyl)))-4-(2-cyanophenyl)-3-buteneamide

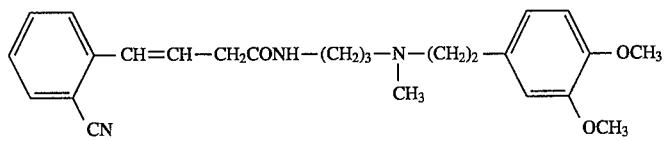

Yellow oily matter
NMR (CDCl₃) δ; 1.5~1.9 (2H, m), 2.13 (3H, s), 2.4~2.8 (6H, m), 3.06 (2H, d, J=6.8Hz)., 3.2–3.5 (2H, m), 3.82 (3H, s), 3.86 (3H, s), 6.48 (1H, dt, J=6.8Hz, 16.2Hz), 6.7~6.9 (4H, m), 7.1~7.7 (5H, m).

Working Example 13

(E)-N-(((3-((N'-(2-(3,4-dimethoxyphenyl)ethyl)-N'-methyl)amino)propyl))-3-(2-trifluoromethyl)phenyl)propeneamide

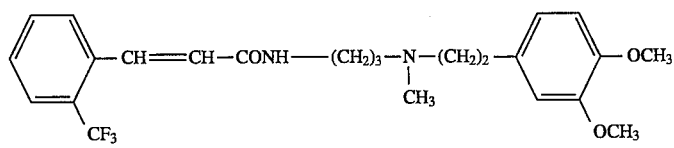

Yellow oily matter
NMR (CDCl₃) δ; 1.6~1.9 (2H, m), 2.30 (3H, s), 2.4~2.8 (6H, m), 3.3~3.8 (2H, m), 3.71 (3H, s), 3.79(3H, s), 6.10 (1H, d, J=16Hz), 6.6~6.8 (3H, m), 7.2~7.8 (6H, m).

Working Example 14

(E)-N-(((3-((N'-(2-(3,4-dimethoxyphenyl)ethyl)-N'-methyl)amino)propyl)))-3-(3-trifluoromethyl)phenyl)propeneamide

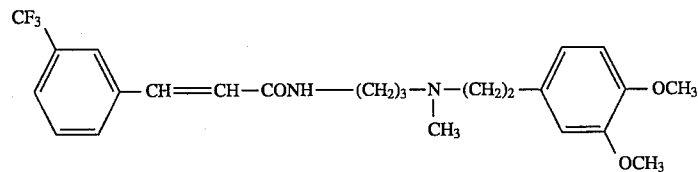

Yellow oily matter
NMR (CDCl₃) δ; 1.6~2.0 (2H, m), 2.32 (3H, s), 2.4~2.9 (6H, m), 3.2~3.7 (2H, m), 3.74 (3H, s), 3.84 (3H, s), 6.16 (1H, d, J=18Hz), 6.76 (3H, s), 7.20 (1H, br), 7.4~7.8 (6H, m).

Working Example 15

(E)-N-(((3-((N'-(2-(3,4-dimethoxyphenyl)ethyl)-N'-methyl)amino)propyl))-3-(2-naphthyl)-propeneamide

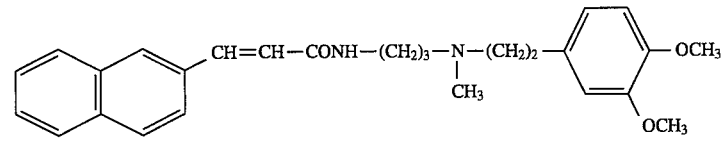

Yellow oily matter
NMR (CDCl₃) δ; 1.7~2.0 (2H, m), 2.42 (3H, s), 2.5~2.9 (6H, m), 3.4~3.9 (2H, m), 3.71 (3H, s), 3.76 (3H, s), 6.30 (1H, d, J=16Hz). 6.76 (3H, s), 7.2 (1H, br), 7.4~8.0 (8H, m).

Working Example 16

(E)-N-(((3-((N'-(2-(3,4-dimethoxyphenyl)ethyl)-N'-methyl)amino)propyl)))-3-(4-chlorophenyl)propeneamide

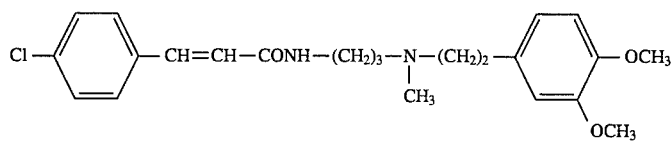

Yellow oily matter
NMR (CDCl$_3$) δ; 1.6~1.9 (2H, m), 2.34 (3H, s), 2.4~2.9 (6H, m), 3.3~3.6 (2H, m), 3.76 (3H, s), 3.84 (3H, s), 6.10(1H, d, J=16Hz), 6.7~6.9 (3H, m), 7.2 (1H, br), 7.3~7.6 (8H, m).

Working Example 17

(E)-N-(((3-((N'-(2-(3,4-dimethoxyphenyl)ethyl)-N'-methyl)amino)propyl)))-3-(4-methanesulphonylphenyl)propeneamide

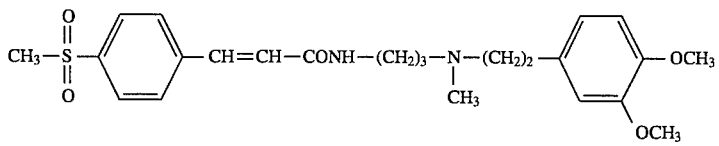

Yellow oily matter

Working Example 18

(E)-N-(((s-((N'-(2-(3,4-dimethoxyphenyl)ethyl)-N'-methyl)amino)propyl)))-3-(4-nitrophenyl)propeneamide

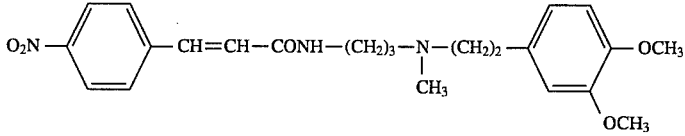

Yellow oily matter 1.5~2.0 (2H, m), 2.32 (3H, s), 2.4~2.8 (6H, m), 3.3~3.6 (2H, m), 3.71 (3H, s). 3.82 (3H, s), 6.10 (1H, d, J=16Hz), 6.6~6.8 (3H, m), 7.2~7.6 (4H, m), 8.0~8.2 (2H, m).

Working Example 19

(E)-N-(((3-((N'-(2-(3,4-dimethoxyphenyl)ethyl)-N'-methyl)amino)propyl)))-3-(3,4-dichlorophenyl)propeneamide

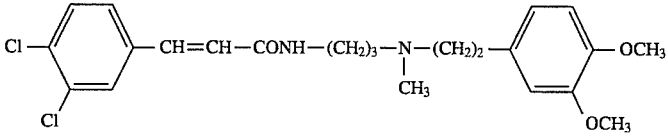

Slightly yellow oily matter
NMR (CDCl$_3$) δ; 1.6~1.9 (2H, m), 2.30 (3H, s), 2.4~2.8 (6H, m), 3.3~3.6 (2H, m), 3.72 (3H, s), 3.82 (3H, s), 6.02 (1H, d, J=18Hz), 6.70 (3H, s), 7.1~7.6 (5H, m).

Working Example 20

(E)-N-(((3-((N'-(2-(3,4-dimethoxyphenyl)ethyl)-N'-methyl)amino)propyl)))-4-(3,4-dichlorophenyl)-3-buteneamide

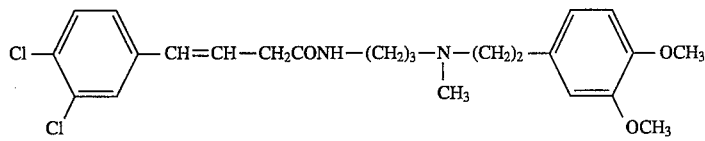

Yellow oily matter
NMR (CDCl$_3$) δ; 1.5~1.8 (2H, m), 2.20 (3H, s), 2.4~2.8 (6H, m), 2.99 (2H, d, J=7Hz), 3.2~3.5 (2H, m), 3.82 (3H, s), 3.84 (3H, s), 6.18 (1H, dt, J=7Hz, 16Hz), 6.38 (1H, d, J=16Hz), 6.5~6.9 (3H, m), 7.0~7.4 (4H, m).

Yellow oily matter
NMR (CDCl$_3$) δ; 1.6~1.9 (2H, m), 2.36 (3H, s), 2.3~2.8 (6H, m), 3.3~3.6 (2H, m), 3.76 (3H, s), 3.80 (3H, s), 3.82 (3H, s), 6.06 (1H, d, J=16 Hz), 6.6~6.9 (5H, m), 7.02 (1H, br), 7.2~7.6 (3H, m).

Working Example 21

(E)-N-(((3-((N'-(2-(3,4-dimethoxyphenyl)ethyl)-N'-methyl)amino)propyl)))-3-(4-(methylthio)phenyl)propeneamide

Working Example 24

(E)-N-(((3-((N'-(2-(3,4-dimethoxyphenyl)ethyl)-N'-methyl)amino)propyl)))-3-(3-chlorophenyl)propeneamide

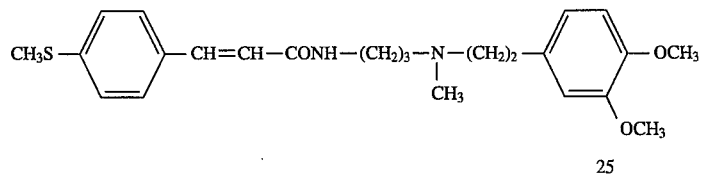

White Crystal
NMR (CDCl$_3$) δ; 1.5~1.9 (2H, m), 2.32 (3H, s), 2.4~2.9 (9H, m), 3.2~3.6 (2H, m), 3.75 (3H, s), 3.82 (3H, s), 6.08 (1H, d, J=16Hz), 6.6~6.8 (3H, m), 7.0~7.7 (6H, m).

Working Example 22

(E)-N-(((3-((N'-(2-(3,4-dimethoxyphenyl)ethyl)-N'-methyl)amino)propyl)))-3-(3,4-methylenedioxyphenyl)propeneamide

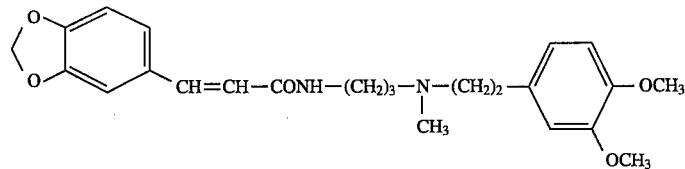

Yellow oily matter
NMR (CDCl$_3$) δ; 1.5~2.0 (2H, m), 2.32 (3H, s), 2.4~2.8 (6H, m), 3.2~3.6 (2H, m), 3.76 (3H, s), 3.84 (3H, s), 5.94 (2H, s), 5.96 (1H, d, J=16 Hz), 6.6~7.2 (8H, m), 7.40 (1H, d, J=16Hz).

Working Example 23

(E)-N-(((3-((N'-(2-(3,4-dimethoxyphenyl)ethyl)-N'-methyl)amino)propyl)))-3-(4-methoxyphenyl)propeneamide

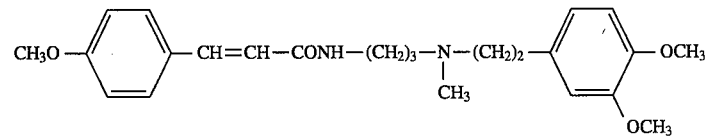

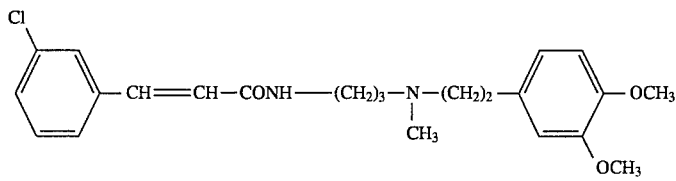

Yellow oily matter
NMR (CDCl₃) δ; 1.5~2.0 (2H, m), 2.32 (3H, s), 2.4~2.8 (6H, m), 3.2~3.6 (2H, m), 3.72 (3H, s), 3.82 (3H,s), 6.08 (1H, d, J=16Hz). 6.6~6.8 (3H, m), 7.1~7.5 (6H, m).

Working Example 25

(E)-N-(((3-((N'-(2-(3,4-dimethoxyphenyl)ethyl)-N'-methyl)amino)propyl)))-3-(4-methylphenyl)propeneamide

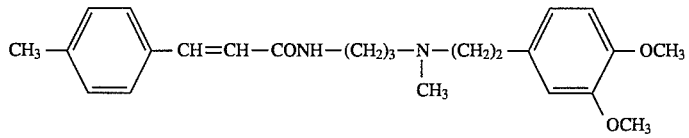

Slightly yellowish oily matter
NMR (CDCl₃) δ; 1.5~1.9(2H, m), 2.30 (3H, s), 2.32 (3H, s), 2.4~2.8 (6H, m), 3.3~3.6 (2H, m), 3.74 (3H, s), 3.82 (3H, s), 6.16 (1H, d, J=17Hz), 6.6~6.8 (3H, m), 7.0~7.4 (5H, m), 7.50 (1H, d, J=17Hz).

Working Example 26

(E)-N-(((3-((N'-(2-(3,4-dimethoxyphenyl)ethyl)-N'-methyl)amino)propyl)))-3-(3-fluoro-4-methoxyphenyl)propeneamide

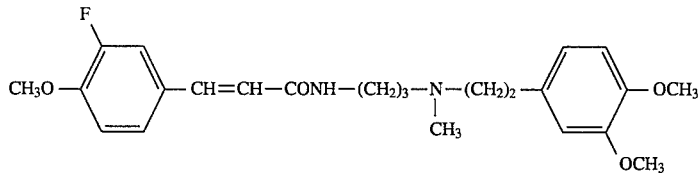

Slightly yellowish matter
NMR (CDCl₃) δ; 1.5~1.9 (2H, m), 2.32 (3H, s), 2.4~2.8 (6H, m), 3.3~3.6 (2H, m). 3.78 (3H, s). 3.86 (3H, s), 3.92 (3H, s), 6.00 (1H, d, J=17 Hz), 6.7~7.4 (7H, m), 7.46 (1H, d, J=17Hz).

Working Example 27

(E)-N-(((3-(-(2-(3,4-dimethoxyphenyl)ethyl)-N'-methyl)amino)propyl)))-4-phenyl)-3-buteneamide

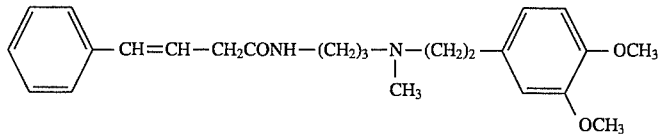

Yellow oily matter
NMR (CDCl₃) δ; 1.5~1.9 (2H, m), 2.30 (3H, s), 2.4~2.7 (6H, m), 3.10 (2H, d, J=8Hz), 3.2~3.5 (2H, m), 3.86 (6H, s), 6.0~6.5 (2H, m), 6.5~6.9(3H,m), 7.0~7.5 (6H, m).

Working Example 28

(E)-N-(((3-((N'-(2-(3,4-dimethoxyphenyl)ethyl)-N'-methyl)amino)propyl)))-3-(3,5-dimethoxyphenyl)propeneamide

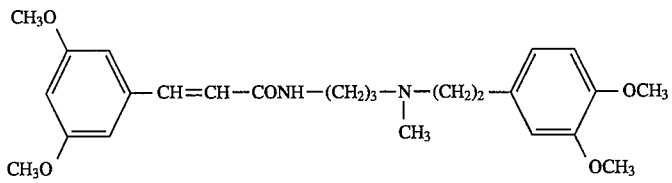

Slightly yellowish matter
NMR (CDCl₃) δ; 1.5~1.9 (2H, m), 2.20 (3H, m), 2.2~2.7 (6H, m), 3.2~3.5 (2H, m), 3.66 (9H, s), 3.72 (3H, s), 6.16 (1H, d, J=18Hz), 6.2~6.7 (6H, m), 7.24 (1H, br), 7.36 (1H, d, J=18Hz).

Working Example 29

(E)-N-(((3-((N'-(2-(3,4-dimethoxyphenyl)ethyl)-N'-methyl)amino)propyl)))-4-((2-isopropyloxy-4-methoxy-3-methyl)phenyl)-3-buteneamide

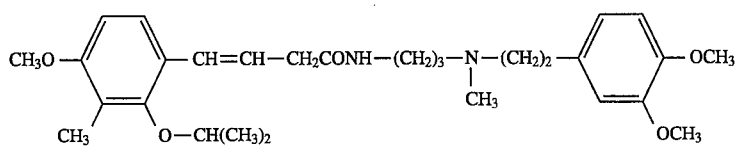

Yellow oily matter
NMR (CDCl₃) δ; 1.28 (6H, d, J=7Hz), 1.5~1.9 (2H, m), 2.10 (3H, s), 2.20 (3H, s), 2.3~2.9 (6H, m), 3.06 (2H, d, J=6Hz), 3.2~3.5 (2H, m), 3.76 (3H, s), 3.82 (3H, s), 3.84 (3H, s), 3.9~4.3 (1H, m), 6.04 (, dt, J=6Hz, 16Hz), 6.4~6.9 (5H, m), 7.04 (1H, br), 8.23 (1H, d, J=9Hz).

Working Example 30

(E)-N-(((3-((N'-(2-(3,4-dimethoxyphenyl)ethyl)-N'-methyl)amino)propyl)))-4-(2,4-difluorophenyl)-3-buteneamide

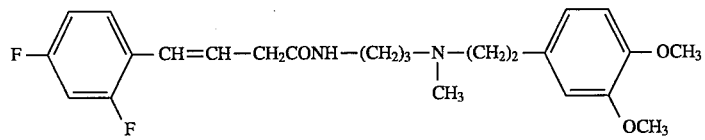

Slightly yellowish oily matter
NMR (CDCl₃) δ; 1.5~1.9 (2H, m), 2.24 (3H, s), 2.4~2.8 (6H, m), 3.04 (2H, d, J=6Hz), 3.1~3.5 (2H, m), 3.90 (6H, s), 6.0~6.5 (2H, m), 6.5~7.0 (5H, m), 7.1~7.4 (2H, m).

Working Example 31

(E)-N-(((3-((N'-(2-(3,4-dimethoxyphenyl)ethyl)-N'-methyl)amino)propyl)))-N-methyl-3-(3,4-dimethoxyphenyl)propeneamide

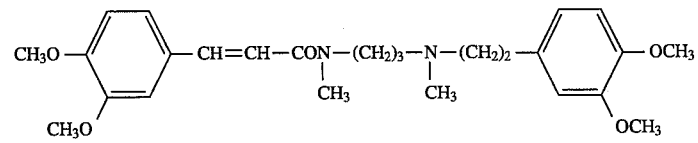

Slightly yellowish oily matter
NMR (CDCl₃) δ; 1.7~2.0 (2H. 2.2~2.9 (9H, m), 3.04, 3.16 (total 3H, br s), 3.84 (6H, s), 3.90 (6H, s), 6.6~7.2 (7H, m), 7.66 (1H, d, J=16Hz).

Working Example 32

(E)-N-(((3-((N'(2-(3,4-dimethoxyphenyl)ethyl)-N'-methyl)amino)propyl)))-N-methyl-3-(4-dicyanophenyl)propeneamide $$\text{NC}-\underset{}{\bigcirc}-\text{CH}=\text{CH}-\underset{\underset{C_2H_5}{|}}{\text{CON}}-(\text{CH}_2)_3-\underset{\underset{CH_3}{|}}{\text{N}}-(\text{CH}_2)_2-\underset{\underset{OCH_3}{}}{\bigcirc}-\text{OCH}_3$$

Yellowish oily matter
NMR (CDCl₃) δ; 1.0~1.4 (3H, m), 1.6~2.0 (2H, m), 2.30, 2.34 (total 3H, s), 2.4~2.8(6H, m), 3.2~3.6 (4H, m), 3.84 (6H, s), 6.6~6.9 (3H, m), 7.10 (1H, d, J=18Hz), 7.5~7.8 (5H, m).

Working Example 33

(E)-N-(((3-((N'-(2-(3,4-dimethoxyphenyl)ethyl)-N'-methyl)amino)propyl)))-N-ethyl-3-(4-chlorophenyl)propeneamide $$\text{Cl}-\underset{}{\bigcirc}-\text{CH}=\text{CH}-\underset{\underset{C_2H_5}{|}}{\text{CON}}\mathrm{+CH_2\mathrm{)}_3}\underset{\underset{CH_3}{|}}{\text{N}}\mathrm{+CH_2)_2}-\underset{\underset{OCH_3}{}}{\bigcirc}-\text{OCH}_3$$

Slightly yellowish oily matter
NMR (CDCl₃) δ; 1.0~1.3 (3H, m), 1.6~2.0 (2H, m), 2.3 (3H, br), 2.3~2.8 (6H, m), 3.2~3.6 (4H, m), 3.80 (6H, s), 6.6~6.8 (3H, m), 6.90 (1H, d, J=16Hz), 7.2~7.6 (4H, m), 7.62 (1H, d, J=16Hz).

Working Example 34

(E)-N-(((3-((N'-(2-(3,4-dimethoxyphenyl)ethyl)-N'-methyl)amino)propyl)))-N-methyl-3-(4-fluorophenyl)propeneamide $$\text{F}-\underset{}{\bigcirc}-\text{CH}=\text{CH}-\underset{\underset{CH_3}{|}}{\text{CON}}\mathrm{+CH_2\mathrm{)}_3}\underset{\underset{CH_3}{|}}{\text{N}}\mathrm{+CH_2)_2}-\underset{\underset{OCH_3}{}}{\bigcirc}-\text{OCH}_3$$

Yellow oily matter
NMR (CDCl₃) δ; 1.6~2.0 (2H, m), 2.2~2.8 (9H, m), 3.00, 3.10(total 3H, s), 3.3~3.6 (2H, m), 3.80 (6H, s), 6.6~6.8 (3H, m), 6.8~7.4 (6H, m).

Working Example 35

(E)-N-(((3-((N'-(2-(3,4-dimethoxyphenyl)ethyl)-N'-methyl)amino)propyl)))-N-methyl-4-(4-fluorophenyl)-3-buteneamide $$\text{F}-\underset{}{\bigcirc}-\text{CH}=\text{CH}-\text{CH}_2\underset{\underset{CH_3}{|}}{\text{CON}}-(\text{CH}_2)_3-\underset{\underset{CH_3}{|}}{\text{N}}-(\text{CH}_2)_2-\underset{\underset{OCH_3}{}}{\bigcirc}-\text{OCH}_3$$

Brown oily matter
NMR (CDCl₃) δ; 1.5~2.0 (2H, m), 2.28, 2.30(total 3H, s), 2.3~2.8 (6H, m), 2.96 (2H, d, J=8Hz), 3.1~3.6 (5H, m), 3.84 (6H, s), 6.0~6.6 (2H,m), 6.6~1.4 (7H, m).

Working Example 36

(E)-N-(((3-((N'-(2-(3,4-dimethoxyphenyl)ethyl)-N'-methyl)amino)propyl)))-N-methyl-3-(3-fluorophenyl)propeneamide $$\text{F}-\underset{}{\bigcirc}-\text{CH}=\text{CH}-\underset{\underset{CH_3}{|}}{\text{CON}}-(\text{CH}_2)_3-\underset{\underset{CH_3}{|}}{\text{N}}-(\text{CH}_2)_2-\underset{\underset{OCH_3}{}}{\bigcirc}-\text{OCH}_3$$

Yellow oily matter
NMR (CDCl₃) δ; 1.5~2.0(2H, m), 2.4~2.9 (9H, m), 3.00, 3.12(total 3H, s), 3.3~3.6 (2H, m), 3.80 (6H,s), 6.5~8.8(3H, m), 6.8~7.4 (5H, 7.46(1H, d, J=14Hz).

Working Example 37

(E)-N-(((3-((N'-(2-(3,4-dimethoxyphenyl)ethyl)-N'-methyl)amino)propyl)))-N-ethyl-3-(4-fluorophenyl)propeneamide $$\text{F}-\underset{}{\bigcirc}-\text{CH}=\text{CH}-\underset{\underset{C_2H_5}{|}}{\text{CON}}\mathrm{+CH_2\mathrm{)}_3}\underset{\underset{CH_3}{|}}{\text{N}}-(\text{CH}_2)_2-\underset{\underset{OCH_3}{}}{\bigcirc}-\text{OCH}_3$$

Yellow oily matter
NMR (CDCl₃) δ; 1.17, 1.24 (total 3H, t, J=6Hz), 1.6~2.0 (2H, m), 2.2~2.8 (9H, m), 3.2~3.6 (2H, m), 3.80 (6H, s), 6.7~6.8 (4H, m), 6.8~7.1 (2H,m), 7.2~7.7 (3H, m).

Working Example 38

(E)-N-(((3-((N'-(2-(3,4-dimethoxyphenyl)ethyl)-N'-methyl)amino)propyl)))-N-ethyl-4-(4-fluorophenyl)-3-buteneamide

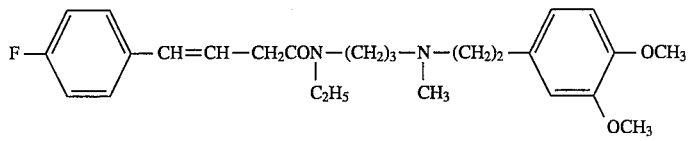

Yellow oily matter
NMR (CDCl₃) δ; 1.10, 1.16(total 3H, t, J6Hz), 1.5~1.9 (2H, m), 2.1~2.8 (9H, m), 3.1~3.6 (6H, m), 3.82 (6H, s), 6.2~6.4 (2H, m), 6.6~7.4 (7H,m).

Working Example 39

(E)-N-(((3-((N'-(2-(3,4-dimethoxyphenyl)ethyl)-N'-methyl)amino)propyl)))-N-cyclopentyl-4-(4-cyanophenyl)-3-buteneamide

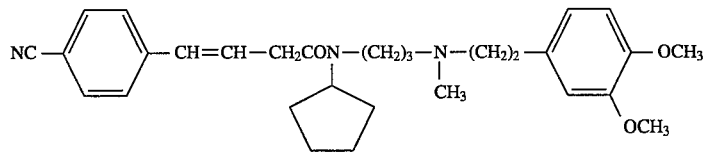

Yellow oily matter
NMR (CDCl₃) δ; 1.3~2.0 (10H, m), 2.2~2.8 (9H, m), 2.9~3.4 (4H, m), 3.80 (3H, s), 3.82 (3H, s), 3.9~4.7(1H, br m), 6.2~6.9 (5H, m), 7.2~7.6 (4H, m).

Working Example 40

(E)-N-(((3-((N'-(2-(3,4-dimethoxyphenyl)ethyl)-N'-methyl)amino)propyl)))-N-cyclopentyl-4-(4-methylphenyl)-3-buteneamide

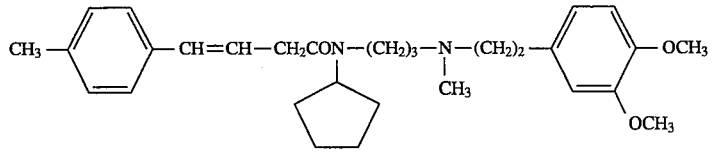

Yellow oily matter
NMR (CDCl₃) δ; 1.3~2.0 (10H, m), 2.2~2.9 (9H, m), 3.0~3.4 (4H, m), 3.80 (3H, s), 3.82 (3H, s), 3.9~4.8 (1H, br m), 6.20 (1H, dt, J=6Hz, 16Hz), 6.40 (1H, d, J=16Hz), 6.5~6.9 (3H, m), 6.9~7.3 (4H, m).

Working Example 41

(E)-N-(((3-((N'-(2-(3,4-dimethoxyphenyl)ethyl)-N'-methyl)amino)propyl)))-N-cyclopentyl-4-phenyl-3-buteneamide

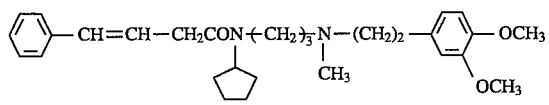

Yellow oily matter
NMR (CDCl₃) δ; 1.2~2.0 (10H, m), 2.2~2.9 (9H, m), 3.0~3.4 (4H, m), 3.79 (3H, s), 3.81 (3H, s), 3.9~4.7 (1H, br m), 6.20 (1H, dt, J=6Hz, 16Hz), 6.44 (1H, d, J=16Hz), 6.6~6.8 (3H, m), 7.1~7.5 (5H, s).

Working Example 42

(E)-N-(((3-((N'-(2-(3,4-dimethoxyphenyl)ethyl)-N'-methyl)amino)propyl)))-N-cyclopentyl-4-(4-methoxyphenyl)-3-buteneamide

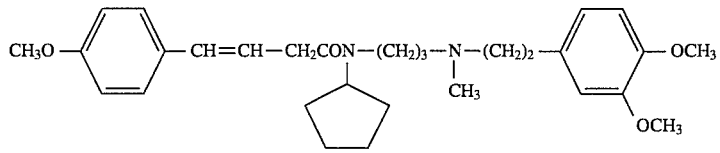

Yellow oily matter
NMR (CDCl$_3$) δ; 1.4~2.0 (10H, m), 2.1~2.9 (9H, m), 3.1~3.4 (4H, m), 3.76 (3H, s), 3.84(3H, s), 3.86 (3H, s), 4.0~4.8 (1H, br m), 6.16 (1H, dt, J=6Hz, 16Hz), 6.41 (1H, d, J=16Hz), 6.6~7.0 (5H, m), 7.2~7.4 (2H, m).

Working Example 43

(E)-N-(((3-((N'-(2-(3,4-dimethoxyphenyl)ethyl)-N'-methyl)amino)propyl)))-N-cyclopentylmethyl-4-(3,4-(methylenedioxy)phenyl-3-buteneamide

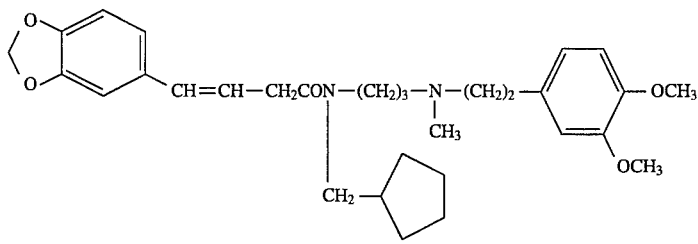

Yellow oily matter
NMR (CDCl$_3$) δ; 1.0~1.9(11H, m), 2.0~2.8 (9H, m), 3.1~3.5 (6H,m), 3.80 (3H,s), 3.82 (3H, s), 5.87 (2H, s), 6.08 (1H, dt, J=6Hz, 16Hz), 6.32g (1H, d, J=16Hz). 6.5~6.9 (6H, m).

Working Example 44

(E)-N-(((3-((N'-(2-(3,4-dimethoxyphenyl)ethyl)-N'-methyl)amino)propyl)))-N-aryl-4-(3,4-(methylenedioxy)phenyl)-3buteneamide

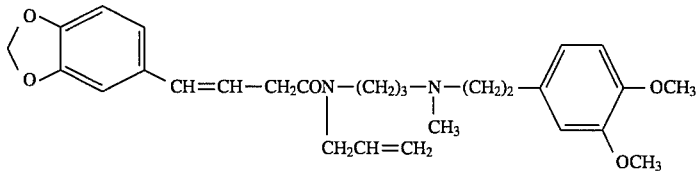

Yellow oily matter
NMR (CDCl$_3$) δ; 1.5~2.0 (2H, m), 2.2~2.9 (9H, m), 3.1~3.5 (4H, m), 3.8~4.1 (8H, m), 5.0~5.4 (2H, m), 5.5~5.9 (1H, m), 5.97 (2H, s), 6.1~6.6 (2H, m), 6.6~7.0 (6H, m).

Working Example 45

(E)-N-(((3-((N'-(2-(3,4-dimethoxyphenyl)ethyl)-N'-methyl)amino)propyl)))-N-propyl-4-(3,4-(methylenedioxy)-phenyl-3-buteneamide

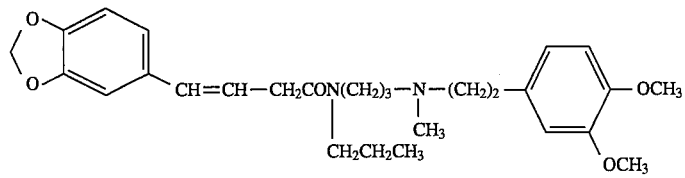

Yellow oily matter
NMR (CDCl$_3$) δ; 0.86, 0.90 (total 3H, t, J=7Hz), 1.3~1.9 (4H, m), 2.1~2.8 (9H, m), 2.9~3.5 (6H, m), 3.80 (3H, s), 3.82 (3H, s), 5.86 (2H, s), 6.08 (1H, dt, J=6Hz, 16Hz), 6.33 (2H, d, J=16) Hz), 6.5~6.9 (6H, m).

Working Example 46

(E)-N-(((3-((N'-(2-(3,4-dimethoxyphenyl)ethyl)-N'-methyl)amino)propyl)))-N-(2-methylpropyl)-4-(3,4-(methylenedioxy)phenyl)-3-buteneamide

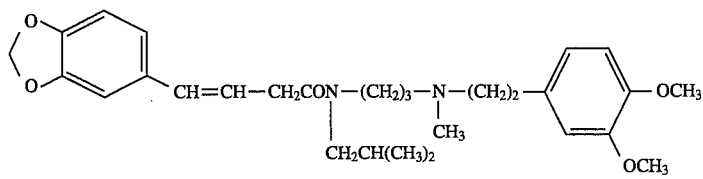

Yellow oily matter
NMR (CDCl$_3$) δ; 1.04 (3H, d, J=7Hz), 1.10 (3H, d, J=7Hz), 1.5~2.1 (3H, m), 2.2~2.8 (9H, m), 2.9~3.5 (6H, m), 3.78 (3H, s), 3.80 (3H, s), 5.94 (2H, s), 6.08 (1H, dt, J=6Hz, 16Hz), 6.31 (2H, d, J=16Hz), 6.5~6.9 (6H, m).

Working Example 47

(E)-N-(((3-((N'-(2-(3,4-dimethoxyphenyl)ethyl)-N'-methyl)amino)propyl)))-N-(1-methylpropyl)-4-(3,4-(methylenedioxy)phenyl-3-buteneamide

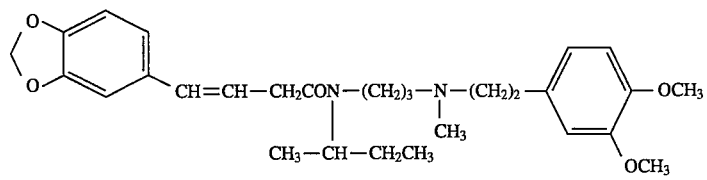

Yellow oily matter
NMR (CDCl$_3$) δ; 1.06, 1.08 (total 3H, d, J=7Hz), 1.08, 1.20 (total 3H, d, J=7Hz), 1.3~2.0 (4H, m), 2.3~2.9 (9H, m), 3.0~3.4 (4H, m), 3.84 (3H, s), 3.86 (3H, s), 5.98 (2H, s), 6.28 (1H, dt, J=6Hz, 16Hz), 6.40 (1H, d, J=16Hz).

Working Example 48

(E)-N-(((3-((N'-(2-(3,4-dimethoxyphenyl)ethyl)-N'-methyl)amino)propyl)))-N-cyclohexyl-4-(3,4-(methylenedioxy)phenyl)-3-buteneamide

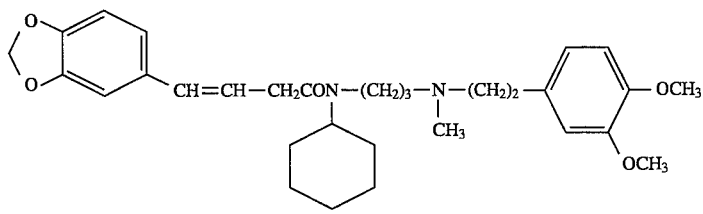

Yellow oily matter
NMR (CDCl$_3$) δ; 0.9~2.1(1 2H, m), 2.2~2.9 (9H, m), 3.1~3.4 (4H, m), 3.84 (3H, s), 3.86 (3H, s), 3.9~4.4(1H, br), 5.92 (2H, s), 6.1~6.5 (2H, m), 6.6~7.0 (6H, m).

Working Example 49

(E)-N-(((3-((N'-(2-(3,4-dimethoxyphenyl)ethyl)-N'-methyl)amino)propyl)))-N-tert-butyl-4-(3,4-(methylenedioxy)phenyl-3-buteneamide

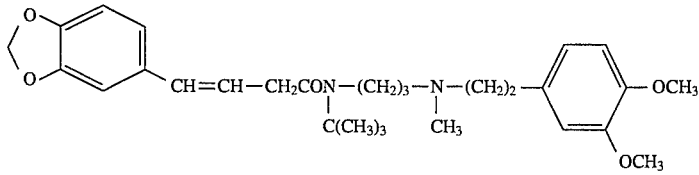

Yellow oily matter
NMR (CDCl$_3$) δ; 1.44 (9H, s), 1.5~1.9 (2H, m), 2.2~2.9 (9H, m), 3.1~3.5 (4H, m), 3.81 (3H, s), 3.83 (3H, s), 5.87 (2H, s), 6.08 (1H, dt, J=6 Hz, 16Hz), 6.32 (1H, d, J=16Hz), 6.5~6.9 (6H, m).

Working Example 50

(E)-N-(((3-((N'-(2-(3,4-dimethoxyphenyl)ethyl)-N'-methyl)amino)propyl)))-N-isopropyl-4-(3,4-

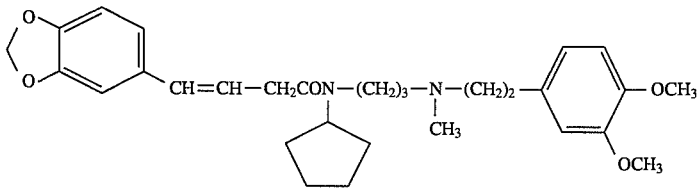

Yellow oily matter
NMR (CDCl$_3$) δ; 1.1~2.0 (10H, m), 2.2~2.8 (9H, m), 3.1~3.4 (4H, m), 3.86 (3H, s), 3.88 (3H, s), 3.9~4, 8 (1H, br m), 5.92 (2H, s), 6.16 (1H, dt, J=6Hz, 16Hz), 6.41 (1H, d, J=16Hz), 6.8~7.0 (6H, m).

Working Example 51

(E)-N-(((3-((N'-(2-(4-methoxyphenyl)ethyl)-N'-methyl)amino)propyl)))-N-cyclopentyl-4-(3,4-(methylenedioxy)phenyl-3-buteneamide

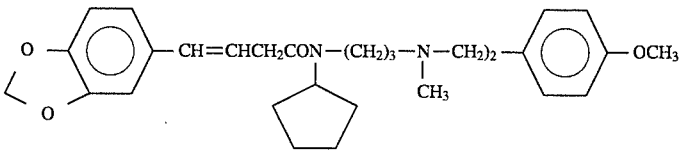

Yellow oily matter
NMR (CDCl$_3$) δ: 1.3~2.0 (10H,m), 2.3 (3H, S), 2.3~2.84 (6H,m), 3.0~3.32 (4H,m), 3.72 (3H,S); (3.9~4J (1H,m), 5.86 (2H, s), 6.1 (1H, dt; J=6Hz, 16Hz), 6.3 (1H,d, J=16H$_2$); 6.6~7.16 (7H,m).

Working Example 52

(E)-N-(((3-((N'-(2-(3-methoxyphenyl)ethyl)-N'-methyl)amino)propyl)))-N-cyclopentyl-4-(3,4-(methylenedioxy)phenyl-3-buteneamide

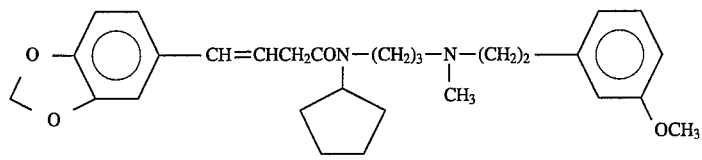

Yellow oily matter
NMR (CDCl₃) δ: 1.3~2.0 (10H,m), 2.26 (3H, s), 7.3~2.9 6H,m), 3.6~3.5 (4H,m), 3.72 (3H,s); 3.92~4.56 (1H, M), 5.86 (2H, S), 6.08 (1H, dt; J=6Hz, 16Hz), 6.32 (1H, d, J=16Hz), 6.5~7.24 (7H,m).

Working Example 53

(E)-N-(((3-((N'-(2-(4-dimethoxyphenyl)ethyl)-N'-methyl)amino)propyl)))-2-cyano-3-(3,4-(dimethoxyphenyl)propeneamide

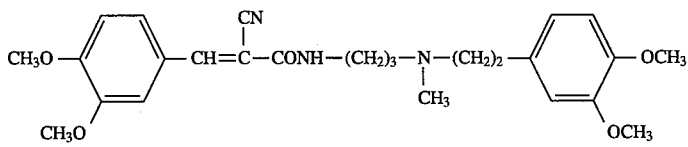

Yellow oily matter
NMR (CDCl₃) δ; 1.6~1.9 (2H, m), 2.36 (3H, s), 2.5~2.9 (6H, m), 3.3~3.6 (2H, m), 3.76 (3H, s), 3.82 (3H, s), 3.90 (6H, s), 6.68 (3H, s), 6.82 (1H, d, J=8Hz). 7.40 (1H, dd, J=3Hz, 8Hz), 7.64 (1H, d, J=3Hz). 8.12 (1H, s), 8.76 (1H, Working Example 54

(E)-N-(((3-((N'-(2-(3,4-dimethoxyphenyl)ethyl)-N'-methyl)amino)propyl)))-3-methyl-3-(3,4-(dimethoxyphenyl)propeneamide

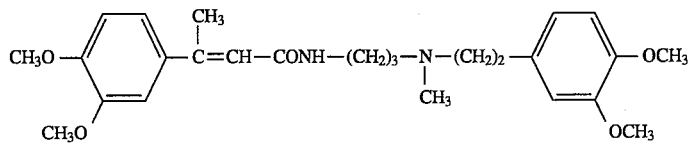

Yellow oily matter
NMR (CDCl₃) δ; 1.6~2.0 (2H, m), 2.02 (3H, d, J=2Hz), 2.36 (3H, s), 2.4~2.9 (6H, m), 3.3~3.6 (2H, m), 3.78 (3H, s), 3.80 (3H, s), 3.82 (3H, s), 3.86 (3H, s), 6.5~6.8 (3H, m), 6.8~7.0 (3H, m), 7.08 (1H, d, J=2Hz), 7.60 (1H, br).

Working Example 55

(E)-N-(((3-((N'-(2-(3,4-dimethoxyphenyl)ethyl)-N'-methyl)amino)propyl)))-2-fluoro-3-phenyl)propeneamide

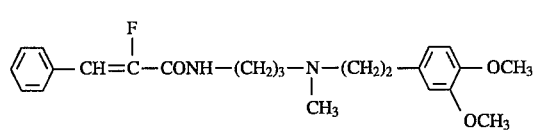

Yellow oily matter
NMR (CDCl₃) δ; 1.6~2.0 (2H, m), 2.32 (3H, s), 2.4~2.9 (6H, m), 3.3~3.7 (2H, m), 3.78 (3H, s), 3.82(3H, s), 6.6~6.8(3H, m), 7.0~7.7 (6H, m), 8.3 (1H, br).

Working Example 56

(E)-N-(((3-((N'-(2-(3,4-dimethoxyphenyl)ethyl)-N'-methyl)amino)propyl)))-2-methyl-3-(4-fluorophenyl)propeneamide

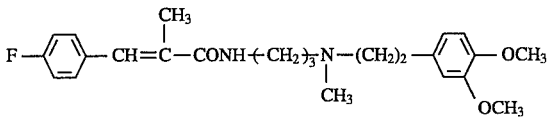

Yellow oily matter
NMR (CDCl₃) δ; 1.6~1.9 (2H, m), 1.96 (3H, d, J=3Hz), 2.32 (3H, s), 2.4~2.8 (6H, m), 3.3~3.6 (2H, m), 3.88 (3H, s), 3.91 (3H, s), 6.5~6.8 (3H, m), 6.8~7.4 (5It, m), 7.70 (1H, br).

Working Example 57

(E)-N-(((3-((N'-(2-(3,4-dimethoxyphenyl)ethyl)-N'-methyl)amino)propyl)))-2-cyano-3-phenylpropeneamide

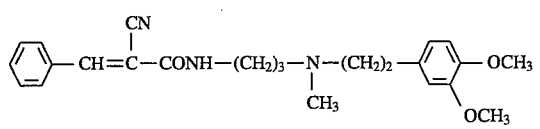

Yellow oily matter
NMR (CDCl₃) δ; 1.6~1.9 (2H, m), 2.3~2.9 (9H, m), 3.3~3.6 (2H, m), 3.78 (3H, s), 3.84 (3H, s), 6.74 (3H, s), 7.4~7.6 (2H, m), 7.8~8.0 (3H, m), 8.28 (1H, s), 8.90 (1H, br).

Working Example 98

(E)-N-(((3-((N'-(2-(4-methoxyphenyl)ethyl)-N'-aryl)amino)propyl)))-4-(4-fluorophenyl)-3-buteneamide

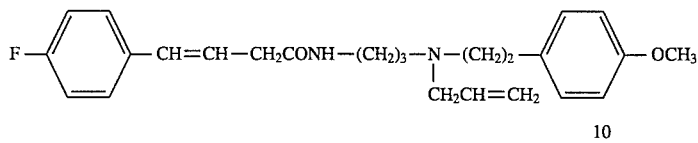

Yellow oily matter
NMR (CDCl$_3$) δ; 1.4~1.8 (2H, m), 2.5~2.7 (6H, m), 2.9~3.2 (4H, m), 3.2~3.5 (2H, m), 3.76 (3H, s), 5.0~5.3 (2H, m), 5.5~6.6 (3H, m), 6.7~7.4 (9H, m).

Working Example 59

(E)-N-(((3-(-(2-(3,4-dimethoxyphenyl)ethyl)-N'-isopropyl)amino)propyl)))-3-(4-fluorophenylpropeneamide

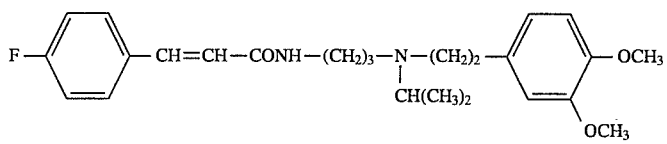

Yellow oily matter
NMR (CDCl$_3$) δ; 1.01 (6H, d, J=7Hz), 1.5~1.9 (2H, m), 2.3~2.9(6H, m), 2.9~3.3(1H, m), 3.3~3.6 (2H, m), 3.75 (3H, s), 3.85 (3H, s), 6.04 (1H, d, J=16Hz), 6.5~6.8 (3H, m), 6.8~7.7 (6H, m).

Working Example 60

(E)-N-(((3-((N'-(2-phenylethyl)-N'-methyl)amino)propyl)))-3-(4-fluorophenyl)propeneamide

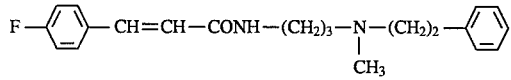

White crystal
NMR (CDCl$_3$) δ; 1.5~1.9 (2H, m), 2.30 (3H, s), 2.4~2.9 (6H, m), 3.3~3.6 (2H, m), 5.99(1H, d, J=16Hz), 6.8~7.6(11H, m).

Working Example 61

(E)-N-(((3-((N'-(2-phenylethyl)-N'-isopropyl)amino)propyl)))-3-(4-fluorophenyl)propeneamide

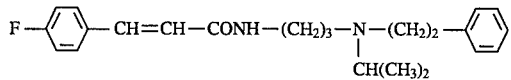

Yellow oily matter
NMR (CDCl$_3$) δ; 0.99 (6H, d, J=7Hz), 1.5~1.9 (2H, m), 2.5~2.8 (6H, m), 2.9~3.3 (1H, m), 3.3~3.6 (2H, m), 5.99 (1H, d, J=16Hz), 6.9~7.6 (11H, m).

Working Example 62

(E)-N-(((3-((N'-(2-(3-methoxyphenyl)ethyl)-N'-isopropyl)amino)propyl)))-3-(4-fluorophenyl)propeneamide

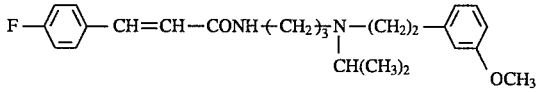

Yellow oily matter
NMR (CDCl$_3$) δ; 1.02 (6H, d, J=7Hz), 1.5~1.9 (2H, m), 2.5~2.9 (6H, m), 2.9~3.3 (1H, m), 3.3~3.6 (2H, m), 3.75 (3H, s), 6.00 (1H, d, J=16Hz), 6.6~7.7 (10H, m).

Working Example 63

(E)-N-(((3-((N'-(2-(2,5-dimethoxyphenyl)ethyl)-N'-methyl)amino)propyl)))-4-(4-fluorophenyl)-3-buteneamide

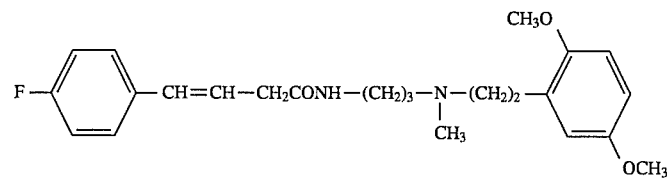

Yellow oily matter
NMR (CDCl₃) δ; 1.5~1.8 (2H, m), 2.16 (3H, s), 2.3~2.8 (6H, m), 3.00 (2H, d, J=8Hz), 3.2~3.5 (2H, m), 3.74 (6H, s), 5.9~6.6 (2H, m), 6.0~7.6 (8H, m).

Working Example 64

(E)-N-(((3-((N'-(2-(3,4-ethylenedioxy)phenyl)ethyl)-N'-methyl)amino)propyl)))-4-(4-fluorophenyl)-3-buteneamide

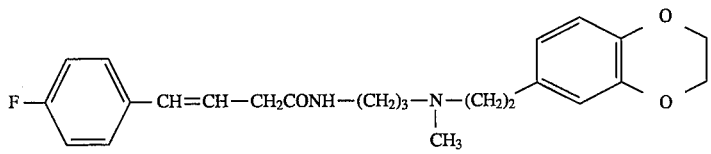

Slightly brownish oily matter
NMR (CDCl₃) δ; 1.5~1.8 (2H, m), 2.10 (3H, s), 2.3~2.6 (6H, m), 2.96 (2H, d, J=6Hz), 3.1~3.4 (2H, m), 4.14 (4H, s), 5.8~7.4 (10H, m).

Working Example 65

(E)-N-(((3-(4-(3,4-dimethoxyphenyl)piperidine-1-yl)propyl)))-4-(4-fluorophenyl)-3-buteneamide

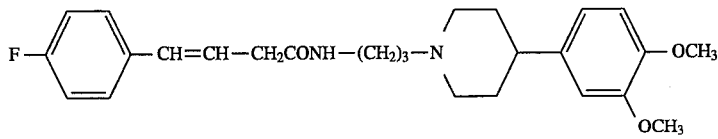

Light yellow solid
NMR (CDCl₃) δ; 1.6~2.6(11H,m), 2.9~3.2(2H, m), 3.2~3.5 (2H, m), 3.81 (6H, s), 6.15 (1H, dt, J=7Hz, 16Hz), 6.44 (1H, d, J=16Hz), 6.6~7.4.

Working Example 66

(E)-N-(((3-((N'-(2-(4-pridyl)ethyl)-N'-methyl)amino)propyl)))-4-(4-fluorophenyl)-3-buteneamide

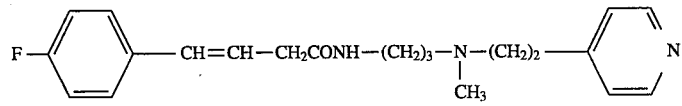

Yellow oily matter
NMR (CDCl₃) δ; 1.4~1.8 (2H, m), 2.15 (3H, s), 2.3~2.7 (6H, m), 3.00 (2H, d, J=7Hz), 3.1~3.5 (2H, m), 6.04 (1H, dt, J=7Hz, 16Hz), 6.36 (1H, d, J=16Hz), 6.7~7.3 (7H, m), 8.3~8.5 (2H, m).

Working Example 67

(E)-N-(1-(2-(3,4-dimethoxyphenyl)ethyl)piperidine-4-yl)-3-(fluorophenyl)propeneamide

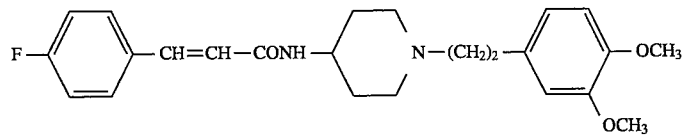

White solid
NMR (CDCl₃) δ; 1.3~1.8(2H,m), 1.9~2.4(6H, m), 2.4~3.1 (7H, m), 3.86 (3H, s), 3.88 (3H, s), 5.68 (1H, d, J=8Hz), 6.32 (1H, d, J=16Hz), 6.6~6.9 (3H, m), 6.9~7.2(2H, m), 7.3~7.7 (3H,m).

Working Example 68

(E)-N-(((4-(-(2-(3,4-dimethoxyphenyl)ethyl-N'-methyl)amino)piperidine 1-yl)-3-(4-fluorophenyl)-3-propeneamide

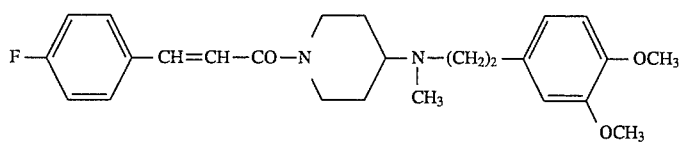

Light Yellow oily matter
NMR (CDCl₃) δ; 1.2~2.1 (4H, m), 2.36 (3H, s), 2.5~3.2 (7H, m), 3.87 (3H, s), 3.89 (3H, s), 6.6~6.8 (3H, m), 6.9~7.3 (4H, m), 7.4~7.8 (3H, m).

Working Example 69

(E)-N-(((N'-(2-(3,4-dimethoxyphenyl)ethyl)-N'-methyl)amino)ethyl-4-(4-fluorophenyl)-3-buteneamide

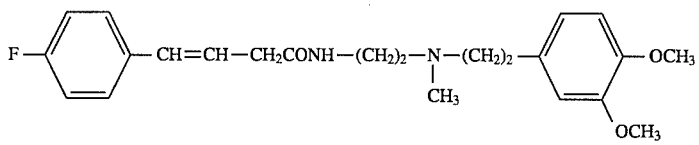

Yellow oily matter
NMR (CDCl₃) δ; 2.28 (3H, s), 2.4~2.8 (6H, m), 3.00 (2H, d, J=7Hz), 3.1~3.4 (2H, m), 3.83 (6H, s), 6.12 (1H, br), 6.14 (1H, dt, J=7Hz, 16Hz), 6.48 (1H, d, J=16Hz), 6.6~6.8 (3H, m), 6.8~7.1 (2H, m), 7.2~7.4 (2H, m) 6.35 (1H, br), 6.49 (1H, d, J=16Hz), 6.6~6.8 (3H, m), 6.8~7.1 (2H, m), 7.2~7.4 (2H, m).

Working Example 70

(E)-N-(((3-((N'-(2-(3,4-dimethoxyphenyl)ethyl-N'-methyl)amino)propyl-4-(4-cyanophenyl)-3-buteneamide

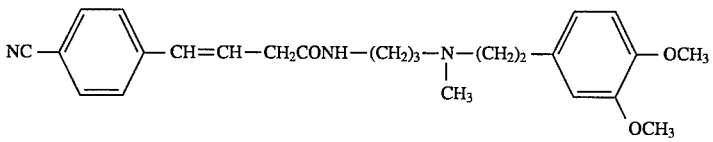

A mixture of 0.72 g of (E)-4-(4-cyanophenyl)-3-butenoic acid, 1.07 g of N-methyl-N-(2-(3,4-dimethoxyphenyl)ethyl)-1,3-propanediamine, 0.87 g of N,N'-dicyclohexylcarbodiimide, 0.57 g of N-hydroxybenzotriazole and 13 ml of acetonitrile was stirred at 70° C. for 30 minutes.

It was then incubated to reduce the temperature. The the depositi was filtered and concentrated.

To this was added water solution of potassium carbonate and extraction was performed with chloroform and then drying was applied with sodium sulfuric anhydride. The solvent was concentrated and the residue was purified by means of silica gel column chromatography (solvent; dichloromethane:methanol=20:1) and the marked compound 1.52 g (yield: 93%) was obtained as yellow oily matter.

NMR (CDCl₃) δ; 1.5~1.8 (2H, m), 2.14 (3H, s), 2.4~2.8 (6H, m), 3.01 (2H, d, J=7Hz), 3.2~3.5 (2H, m), 3.84 (3H, s), 3.86 (3H, s), 6.1~6.5(2H, m), 6.6~6.8(3H, m), 7.1~7.0.

Working Examples 71–95

The following compounds were produced by the same method as above.

Working Example 71

(E)-N-(((3-((N'-(2-(3,4-dimethoxyphenyl)ethyl-N'-methyl)amino)propyl)))-4-(2-fluorophenyl)-3-buteneamide Yellow oily matter NMR (CDCl₃) δ; 1.5~1.8 (2H, m), 2.17 (3H, s), 2.3~2.7 (6H, m), 3.06 (2H, d, J=7Hz), 3.2~3.5 (2H, m), 3.82 (3H, s), 3.84 (3H, s), 6.32 (1H, dt, J=7Hz, 16Hz), 6.5~6.8 (4H, m), 6.9~7.2 (3H, m), 7.2~7.5 (2H, m).

Working Example 72

(E)-N-(((3-((N'-(2-(3,4-dimethoxyphenyl)ethyl)-N'-methyl)amino)propyl)))-4-(3-fluorophenyl)-3-buteneamide Yellow oily matter
NMR (CDCl₃) δ; 1.5~1.8 (2H, m), 2.18 (3H, s), 2.3~2.7 (6H, m), 3.02 (2H, d, J=7Hz), 3.2~3.5 (2H, m), 3.82 (3H, s), 3.84 (3H, s), 6.20 (1H, dt, J=7Hz, 16Hz), 6.43 (1H, d, J=16Hz), 6.6~7.4 (8H,m).

Working Example 73

(E)-N-(((3-((N'-(2-(3,4-dimethoxyphenyl)ethyl)-N'-methyl)amino)propyl)))-4-(4-(dimethylamino)phenyl)-3-buteneamide

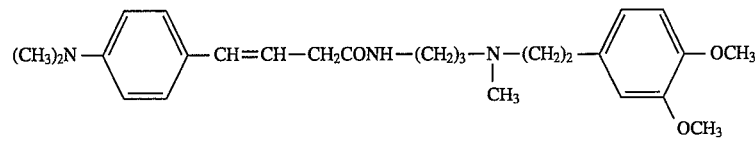

Yellow oily matter
NMR (CDCl$_3$) δ; 1.4~1.8 (2H, m), 2.16 (3H, s), 2.2~2.8 (6H, m), 2.93 (6H, s), 3.03 (2H, d, J=7Hz), 3.1~3.5 (2H, m), 3.84 (3H, s), 3.85 (3H, s), 5.98 (1H, dt, J=7Hz, 16Hz), 6.32 (1H, d, J=16 Hz), 6.4~6.8 (5H, m), 7.0~7.3 (3H, m).

Working Example 74

(E)-N-(((3-((N'-(2-(3,4-dimethoxyphenyl)ethyl)-N'-methyl)amino)propyl)))-4-(3,4,5-trimethoxyphenyl)-3-buteneamide

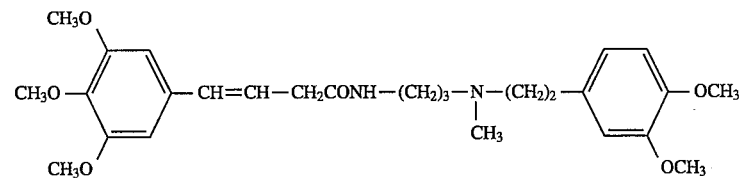

Yellow oily matter
NMR (CDCl$_3$) δ; 1.6~1.9 (2H, 2.28 (3H, s), 2.4~2.8 (6H, m), 3.04 (2H, d, J=6Hz), 3.2~3.5 (2H, m), 3.80 (9H, s), 3.82 (3H, s), 3.84 (3H, s), 6.10 (1, dt, J=6Hz, 16Hz), 6.44 (1H, d, J=16Hz), 6.5~6.8 (6H, m).

Working Example 75

(E)-N-(((3-((N'-(2-(3,4-dimethoxyphenyl)ethyl)-N'-methyl)amino)propyl)))-4-(4-methoxyphenyl)-3-buteneamide

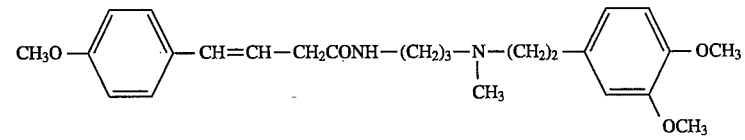

Yellow oily matter
NMR (CDCl$_3$) δ; 1.5~1.8 (2H, m), 2.18 (3H, s), 2.3~2.7 (6H, m), 3.03 (2H, d, J=7Hz), 3.2~3.5 (2H, m), 3.76 (3H, s), 3.82 (3H, s), 3.86 (3H, s), 6.06 (1H, dt, J=7Hz, 16Hz), 6.42 (1H, d, J=16Hz), 6.6~6.9 (5H, 7.2~7.4 (3H, m).

Working Example 76

(E)-N-(((3-((N'-(2-(3,4-dimethoxyphenyl)ethyl)-N'-methyl)amino)propyl)))-4-(3-methoxyphenyl)-3-buteneamide

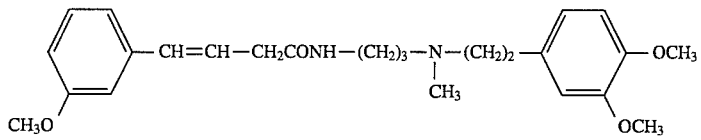

Yellow oily matter
NMR (CDCl$_3$) δ; 1.5~1.9 (2H, m), 2.20 (3H, s), 2.3~2.8 (6H, m), 3.04 (2H, d, J=6.2Hz), 3.1~3.5 (2H, m), 3.75 (3H, s), 3.83 (3H, s), 3.85 (3H,s), 6.25 (1H, dt, J=6.2Hz, 15.8Hz), 6.40 (1H, d, J=15.8Hz), 6.5~7.4 (8H, m).

Working Example 77

(E)-N-(((3-((N'-(2-(3,4-dimethoxyphenyl)ethyl)-N'-methyl)amino)propyl)))-4-(2-methoxyphenyl)-3-buteneamide

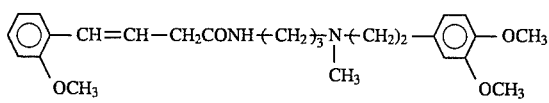

Yellow oily matter
NMR (CDCl$_3$) δ; 1.5~1.8 (2H, m), 2.20 (3H, s), 2.2~2.7 (6H, m), 3.09 (2H, dd, J=(1.0 and 7.0Hz) 3.2~3.5 (2H, m), 3.76 (3H, s), 3.84 (6H, s), 6.25 (1H, dt, J=7.0 and 16.0 Hz), 6.5~7.0 (6, m), 7.1~7.5 (3H, m).

Working Example 78

(E)-N-(((3-((N'-(2-(3,4-dimethoxyphenyl)ethyl)-N'-methyl)amino)propyl)))-3-(4-(acetylamino)phenyl)propeneamide

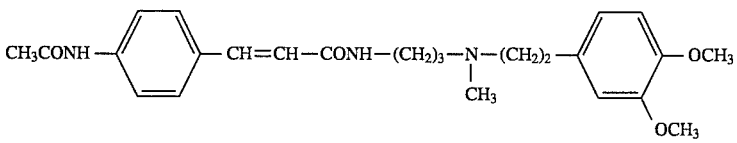

Yellow amorphous matter
NMR (CDCl$_3$) δ; 1.5~1.9 (2H, m), 2.16 (3H, s), 2.32 (3H, s), 2.4~2.9(6H, m), 3.3~3.6(2H, m), 3.74 (3H, s), 3.82 (3H, s), 6.10 (1H, d, J=16Hz), 6.6~6.8 (3H, m), 7.1.~7.8(7H, m).

Working Example 79

(E)-N-(((3-((N'-(2-(3,4-dimethoxyphenyl)ethyl)-N'-methyl)amino)propyl)))-4-(4-(acetylamino)phenyl)-3-buteneamide

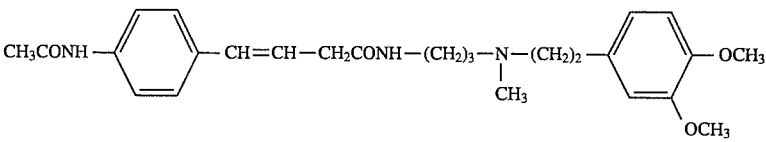

Yellow oily matter
NMR (CDCl$_3$) δ; 1.6~1.9(2H, m), 2. t4(3H, s), 2.18(3H, s), 2.3~2.8 (6H, m), 2.96 (2H, d, J=7Hz), 3.1~3.4 (2H, m), 3.81 (3H, s), 3.84 (3H, s), 6.01 (1H, dt, J=7Hz, 15Hz), 6.33(1H, d, J=15 Hz), 6.4~6.8 (3H, m), 6.9~7.6 (7H, m), 8.82 (1H, s).

Working Example 80

(E)-N-(((3-((N'-(2-(3,4-dimethoxyphenyl)ethyl)-N'-methyl)amino)propyl)))-4-(4-(chlorophenyl)-3-buteneamide

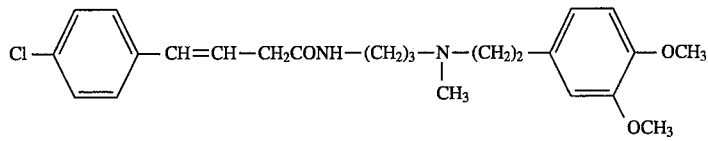

Yellow oily matter
NMR (CDCl$_3$) δ; 1.5~1.8 (2H, m), 2.18 (3H, s), 2.4~2.8 (6H, m), 3.02 (2H, d, J=7Hz), 3.2~3.5 (2H, m), 3.82 (3H, s), 3.86 (3H, s), 6.16 (1H, dt, J=7Hz, 16Hz), 6.43 (1H, d, J=16Hz), 6.6~6.8 (3H, m), 7.1~7.4 (5H, m).

Working Example 81

(E)-N-(((3-((N'-(2-(3,4-dimethoxyphenyl)ethyl)-N'-methyl)amino)propyl)))-4-(4-(methanesulfonyl)phenyl)-3-buteneamide

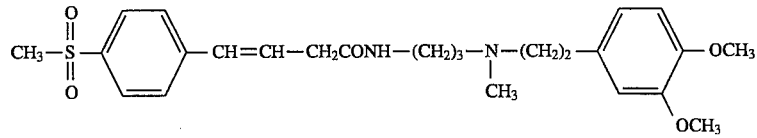

Yellow oily matter
NMR (CDCl$_3$) δ; 1,4~1.9 (2H, m), 2.22 (3H, s), 2.3~2.8 (6H, m), 3.0 0 (3H, s), 3.02 (2H, d, J=4Hz), 3.1~3.5 (2H, m), 3.81 (3H, s), 3.84 (3H, s), 6.3~6.9 (5H, m), 7.0~7.9 (5H, m).

Working Example 82

(E)-N-(((3-((N'-(2-(3,4-dimethoxyphenyl)ethyl)-N'-methyl)amino)propyl)))-4-(4-(methylthio)phenyl)-3-buteneamide

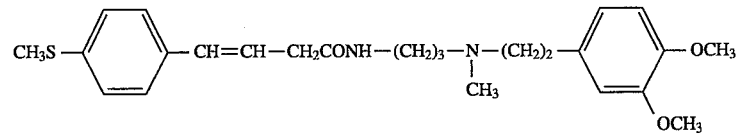

Yellow oily matter
NMR (CDCl$_3$) δ; 1.4~1.8 (2H, m), 2.17 (3H, s), 2.3~2.8 (9H, m), 3.03 (2H, d, J=7Hz), 3.1~3.4 (2H, m). 3.84 (3H, s), 3.85 (3H, s), 5.9~6.8 (5H, m), 6.9~7.4 (5H, m).

Working Example 83

(E)-N-(((3-((N'-(2-(3,4-dimethoxyphenyl)ethyl)-N'-methyl)amino)propyl)))-4-(4-(methyl)phenyl)-3-buteneamide

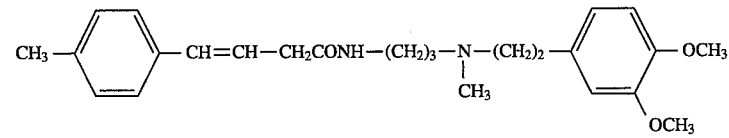

Yellow oily matter
NMR (CDCl$_3$) δ; 1.5~1.8 (2H, m), 2.17 (3H, s), 2.31 (3H, s), 2.4~2.8 (6H, m), 3.03 (2H, d, J=7Hz), 3.2~3.5 (2H, m), 3.83 (3H, s).

Working Example 84

(E)-N-(((3-((N'-(2-(3,4-dimethoxyphenyl)ethyl)-N'-methyl)amino)propyl)))-4-(4-(methoxycarbonyl)phenyl)-3-buteneamide

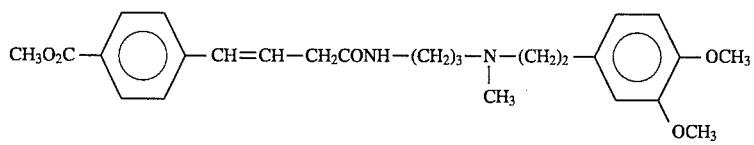

Yellow oily matter
NMR (CDCl$_3$) δ; 1.5~1.9 (2H, m), 2.18 (3H, s), 2.3~2.7 (6H, m), 3.02 (2H, d, J=6Hz), 3.2~3.5 (2H, m), 3.82 (3H, s), 3.84 (3H, s), 3.88 (3H, s), 6.26 (1H, dt, J=6Hz, 16Hz), 6.46 (1H, d, J=16 Hz, 6.5~6.8 (3H, m), 7.1~7.5 (3H, m), 7.8~8.0 (2H, m).

Working Example 85

(E)-N-(((3-(-(2-(3,4-dimethoxyphenyl)ethyl)-N'-methyl)amino)propyl)))-4-(3,4-(ethylenedioxy)phenyl)-3-buteneamide

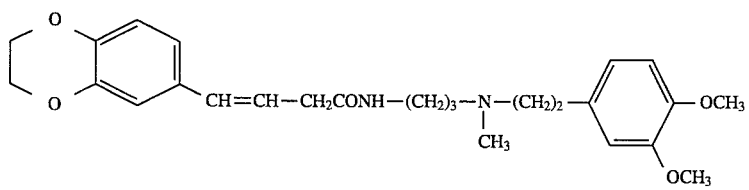

Slightly yellowish oily matter
NMR (CDCl$_3$) δ; 1.5~1.8(2H, m), 2.16(3H, s), 2.4~2.7 (6H, m), 3.02 (2H, d, J=6Hz), 3.2~3.5 (2H, m), 3.92 (3H, s), 3.94 (3H, s), 4.18 (4H, s), 5.8~6.5 (2H, m), 6.6~6.9 (6H, m), 7.15 (1H, br).

Working Example 86

(E)-N-(((3-((N'-(2-(3,4-dimethoxyphenyl)ethyl)-N'-methyl)amino)propyl)))-4-(3,4-(difluoro)phenyl)-3-buteneamide

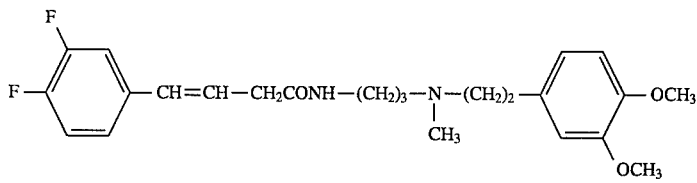

Slightly yellowish oily matter
NMR (CDCl$_3$) δ; 1.5~1.8 (2H, m), 2.22 (3H, s), 2.3~2.8 (6H, m), 3.00 (2H, d, J=6Hz), 3.1~3.3 (2H, m), 3.84 (3H, s), 3.88 (3H, s), 6.10 (1H, dt, J=6Hz, 16Hz), 6.26 (1H, d, J=16Hz), 6.3~6.8 (2H, m), 6.8~7.3 (4H, m).

Working Example 87

(E)-N-(((3-((N'-(2-(3,4-(methylenedioxy)phenyl)ethyl)methyl)amino)propyl)))-4-(4-(fluoropheyl)-3-buteneamide

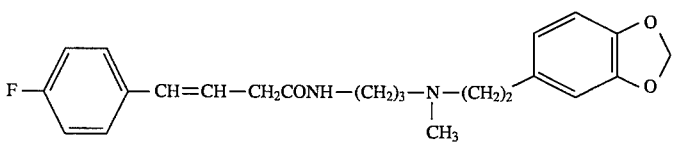

Slightly yellowish oily matter
NMR (CDCl$_3$) δ; 1.5~1.8 (2H, m), 2.12 (3H, s), 2.1~2.6 (6H, m), 2.96 (2H, d, J=8Hz), 3.1~3.4 (2H, m), 5.84 (2H, s), 5.9~7.4 (10H, m).

Working Example 88

(E)-N-(((3-((N'-(2-(3,4,5-trimethoxyphenyl)ethyl)-N'-methyl)amino)propyl)))-4-(4-fluorophenyl)-3-buteneamide

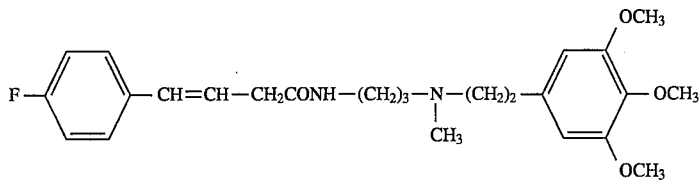

Yellowish brown oily matter
NMR (CDCl₃) δ; 1.5~1.8(2H, m), 2.18(3H, s), 2.3.~2.7 (6H, m), 3.04 (2H, d, J=8Hz), 3.2~3.5 (2H, m), 3.92 (9H, s), 5.9~6.5 (4H, m), 6.8~7.4 (5H, m).

Working Example 89

(E)-N-(((3-((N'-(2-(4-(methoxyphenyl)ethyl)-N'-methyl)amino)propyl)))-4-(4-fluoropheyl)-3-buteneamide

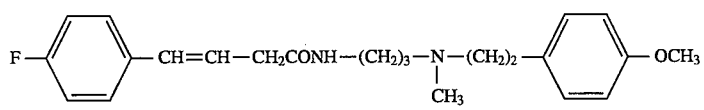

Slightly yellowish oily matter
NMR (CDCl₃) δ; 1.4~1.8 (2H, 2. t2 (3H, s), 2.2~2.7 (6H, m), 2.96 (2H, d, J=8Hz), 3.1~3.5 (2H, m), 3.70 (3H, s), 5.8~6.5 (2H, m), 6.6~7.4 (9H, m).

Working Example 90

(E)-N-(((3-(((N'-(2-(3,4-methylenedioxy)phenyl)ethyl)-N'-methyl)amino)propyl)))-4-(3,4-methylenedioxy)phenyl)-3buteneamide

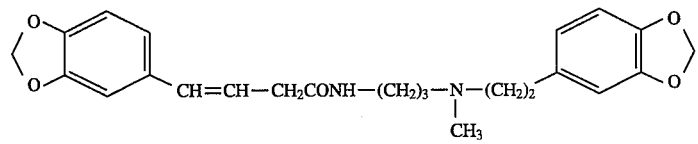

Slightly yellowish solid matter
NMR (CDCl₃) δ; 1.4~1.8(2H, m), 2.16(3H, s), 2.4~2.6 (6H, m), 3.00 (2H, d, J=8Hz), 3.2~3.5 (2H, m), 5.90 (2H, s), 5.92 (2H, s), 6.0~7.0 (8H, m), 7.15 (1H, br).

Working Example 91

(E)-N-(((3-((N'-(2-(4-fluorophenyl)ethyl)-N'-methyl)amino)propyl)))-4-(3,4-methylenedioxy)pheyl)-3-buteneamide

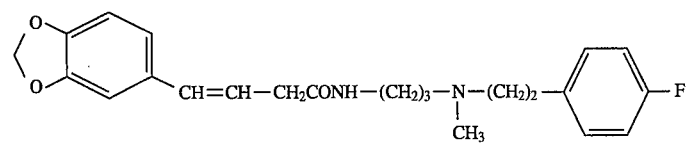

Slightly yellowish solid matter
NMR (CDCl₃) δ; 1.5~1.8 (2H, m), 2.16 (3H, s), 2.3~2.7 (6H, m), 3.02 (2H, d, J=8Hz), 3.2~3.5 (2H, m), 5.90 (2H, s), 6.0~6.6 (2H, m), 6.6~7.3 (8H, m).

Working Example 92

(E)-N-(((3-(-(2-(4-methoxyphenyl)ethyl)-N'-methyl)amino)propyl)))-4-(3,4-methylenedioxy)phenyl)-3-buteneamide

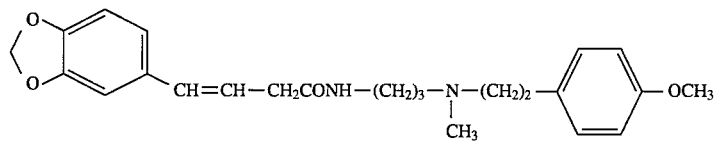

Slightly yellowish solid matter
NMR (CDCl$_3$) δ; 1.5~1.8 (2M, m), 2.18 (3H, s), 2.3.~2.8 (6H, m), 3.00 (2H, d, J=8Hz), 3.2~3.5 (2H, m), 3.76 (3H, s), 5.90 (2H, s), 5.8~6.5(2H, m), 6.8~7.3(8H, m).

Working Example 93

(E)-N'-(((3-((N'-(2-(4-methoxyphenyl)ethyl)-N'-aryl)amino)propyl)))-4-(3,4-methylenedioxy)pheyl)-3-buteneamide

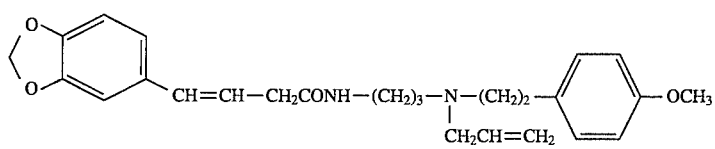

Slightly brownish oily matter
NMR (CDCl$_3$) δ; 1.4~1.8 (2H, m), 2.4~2.7 (6H, m), 2.9~3.2 (4H, m), 3.1~3.5 (2H, m), 3.76 (3H, s), 5.0~5.3 (2H, m), 5.6~6.5 (5H, m), 6.6~7.1 (8H, m).

Working Example 94

(E)-N-(((3-((N'-(2-(3-methoxyphenyl)ethyl)-N'-methyl)amino)propyl)))-4-(3,4-methylenedioxy)phenyl)-3-buteneamide

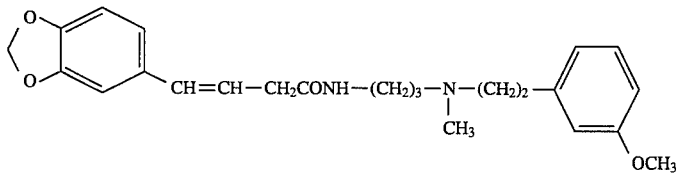

Slightly brownish oily matter
NMR (CDCl$_3$) δ; 1.4~1.8 (2H, m), 2.14 (3H, s), 2.3~2.7 (6H, m), 2.94 (2H, d, J=8Hz), 3.1~3.5 (2H, m), 3.72 (3H, s), 5.7~6.4 (4H, m), 6.5~7.2 (8H, m).

Working Example 95

N-(((2-(3,4-dimethoxyphenyl)ethyl-N'-((((E)-4-(3,4-(methylenedioxy)phenyl)-3-butenoly))))homopiperazine

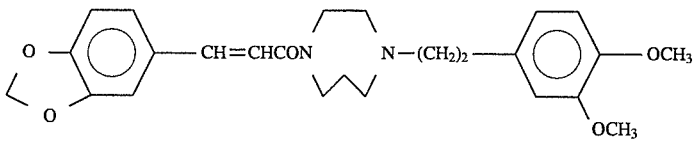

Yellow oily matter
NMR (CDCl$_3$) δ: 1.73~2.08 (2H, m), 2.49~3.05 (8H, m), 3.26 (2H, d, J=7Hz), 3.35~3.78 (4H, m), 3.85 (3H, s), 3.87 (3H, s), 5.93 (3H, S), 6.16 (1H, dt; J=15Hz. 7Hz), 1.42 (1H, d J=15Hz).

Working Example 96

(E)-N-(((3-((N'-(2-(3,4-dimethoxyphenyl)ethyl)-N'-methyl)amino)propyl)))-4-(3,4-methylenedioxy)phenyl)-3-buteneamide

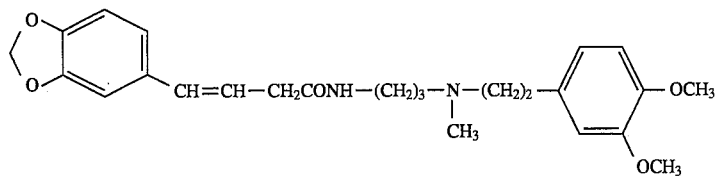

A mixture composed of 37.45 g of (E)-4-(3,4-(methylenedioxy)phenyl)-3-butenoic acid, 23 g of N-hydroxysuccinemide and 800 ml of dichloromethane was incubated on ice and stirred. To this 41.3 g of N,N'-dicyclohexylcarbodiimide dissolved into 200 ml of dichloromethane was added dropwise for 1 hour. After 1.5 hour, 50 g of N-methyl-N-(2-(3,4-dimethoxyphenyl)ethyl)-1,3-propanediamine was added dropwise thereto for 30 minutes. After 5 hours the deposit was filtered and then the organic layer was washed with 0.5N aqueous hydrochloric acid. Then washing was conducted again with water and aqueous sodium carbonate followed by drying with magnesium sulfuric anhydride. The solvent was distilled off and the residue was purified by means of silica gel column chromatography (solvent; chloroform:methanol=50:1–3) to obtain 70.36 g (yield: 88%) of marked compound.

NMR (CDCl$_3$) δ; 1.5~1.9 (2H, m), 2.28 (3H, s), 2.4~2.8 (6H, m), 3.04 (2H, d, J=7Hz), 3.2~3.5 (2H, m), 3.84 (3H, s), 3.86 (3H, s), 5.90 (2H, s), 6.00 (1H, dt, J=7Hz, 18Hz), 6.40 (1H, d, J=18Hz), 6.6~7.0 (6H, m), 7.2(1H, br).

Working Example 97

(E)-N-(((3-((N'-(2-(3,4-dimethoxyphenyl)ethyl)-N'-methyl)amino)-

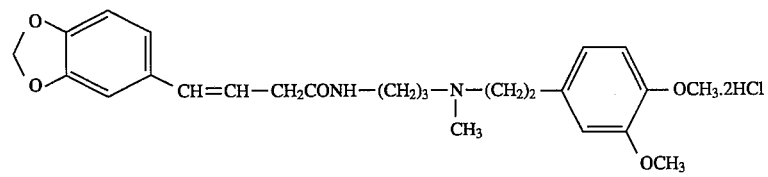

Into 150 ml of methanol was dissolved 72 g of the (E)-N-(((3-((N'-(2-(3,4-dimethoxyphenyl)ethyl)-N'-methyl)amino)propyl)))-4-(3,4-(methylenedioxy)phenyl-3-buteneamide as obtained in the working example 93 hereabove. To this was added ethyl acetate-hydrogen chloride and then ethyl acetate. These were incubated on ice and crystallized. The crystals were filtered and then recrystallized with ethanol-ethyl acetate to obtain 44 g of the marked compound (yield: 52%) as light yellow crystals.

Value of Elemental Analysis: as $C_{25}H_{34}Cl_2N_2O_2$

|  | C | H | N |
| --- | --- | --- | --- |
| Theoretical Value (%) | 58.48 | 6.67 | 5.46 |
| Observed Value (%) | 58.27 | 6.51 | 5.37 |

Working Example 98

(E)-N-(((3-((N'-(2-(3,4-dimethoxyphenyl)ethyl)-N'-methyl)amino)propyl)))-3-(4-dimethylamino)phenyl)propeneamide

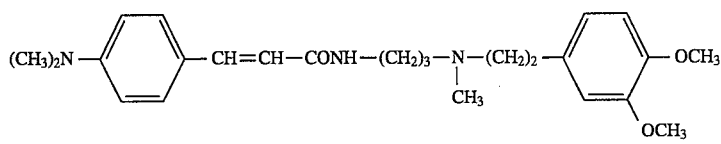

Into a mixture composed of 765 mg or (E)-3-(((4-(dimethylamino)phenyl))-propylenic acid, 0.67 ml of triethylamine and 20 ml of tetrahydrofuran was added 0.64 ml of diethylchlorophosphate under incubation on ice and stirred for 1 hour. To this 1.0 g of N-methyl-N-(((2-(3,4-dimethoxyphenyl)ethyl)))-1,3-propanediamine was added under incubation on ice and stirred for 2 hours. Water was added into reactive liquid, extraction was conducted with dichloromethane and dried up with magnesium sulfuric anhydride. The solvent was distilled off and the residue was purified by means of silica gel column chromatography (solvent; dichloromethane:ethanol=9:1) to obtain 800 mg (yield: 47%) of the marked compound as yellow oily matter.

NMR (CDCl$_3$) δ; 1.56~1.9 (2H, m), 2.74 (3H, s), 2.3~2.9 (6H, m), 3.00 (6H, s), 3.3~3.7 (2H, m), 3.84 (3H, s), 3.88 (3H, s), 6.06 (1H, d, J=16 Hz), 6.5~7.0 (6H, m), 7.2~7.7 (4H, m).

Working Example 99

(E)-N-(((3-((N'-(2-(3,4-dimethoxyphenyl)ethyl)-N'-methyl)amino)propyl)))-3-(4-hydroxyphenyl)propeneamide

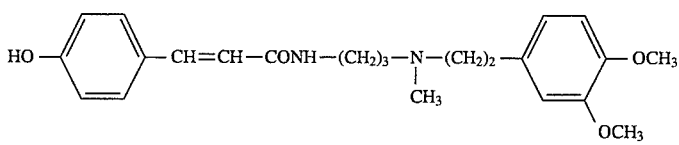

A mixture composed of 0.82 g of (E)-3-(4-hydroxyphenyl)-propylenic acid, 1.68 ml of triethylamine and 5 ml of acetnitrile was cooled down to −10° C. and then stirred. To this was added dropwise 0.92 ml of ethylchloroformate and stirred for 80 minutes. Then was added dropwise thereto 3 ml of acetnitrile solution of 3.02 g of N-methyl-N-(2-(3,4-dimethoxyphenyl)ethyl)-1,3-propanediamine and these were reacted at room temperature for 1 hour. Water was added thereto, extraction was conducted with chloroform and dried up with magnesium sulfuric anhydride. The solvent was distilled off the residue was purified by means of silica gel column chromatography (solvent; chloroform:methanol=10:1) to obtain 0.59 g (yield: 30%) of the marked compound as yellow amorphous matter.

NMR (DMSO-d$_6$) δ; 1.4~1.8 (2H, m), 2.20 (3H, s), 2.3~2.8 (6H, m), 3.0~3.3 (2H, m), 3.86 (3H, s), 3.88 (3H, s), 6.30 (1H, d, J=16Hz), 6.6~6.8 (5H, 7.1~7.5 (3H, m), 7.85 (1H, br).

Working Example 100

(E)-N-(((3-((N'-(2-(3,4-dimethoxyphenyl)ethyl)-N'-methyl)amino)propyl)))-3-(3,4-(methylenedioxy)benzilidene-2-pyrrolidinone

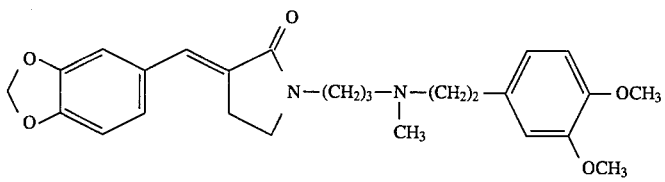

A mixture composed of 1.17 g or (E)-N-(3-chloropropyl)-3-(3,4-(methylenedioxy)benzilidene)-2-pyrrolidinone, 1.55 g of N-methyl-(2-(3,4-dimethoxyphenyl)ethyl)amine hydroiodic acid, 1.33 g of potassium carbonate anhydride and 8 ml of N,N'-dimethylformamide was stirred at 90° C. for 5 hours. These were cooled down, water was added thereto, extraction was conducted with chloroform and then dried up with sodium sulfuric anhydride. The solvent was distilled off and the residue was purified by means of silica gel column chromatography (solvent; chloroform:methanol=30:1) to obtain 1.69 g (yield: 93%) of the marked compound yellow oily matter.

NMR (CDCl$_3$) δ; 1.5~2.0 (2H, m), 2.2~2.8 (9H, m), 2.8~3.1 (2H, m), 3.2~3.6 (4H, m), 3.83(3H,s), 3.85 (3H, s), 5.94 (2H, s), 6.6~7.1 (6H, m), 7.1~7.4 (1H, m).

Working Example 101–107

The following compounds were obtained by the same method as in Working Example 100.

Working Example 101

(E)-N-(((3-((N'-(2-(3,4-dimethoxyphenyl)ethyl)-N'-methyl)amino)propyl)))-3-(4-fluorobenzilidene)-2-pyrrolidinone

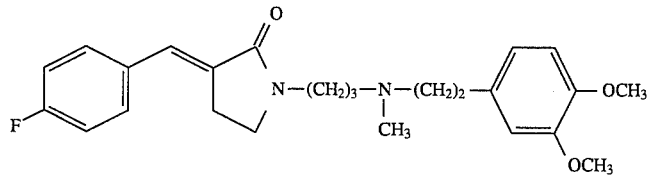

Slightly yellowish oily matter
NMR (CDCl$_3$) δ; 1.7~2.1 (2H, m), 2.40 (3H, s), 2.4~3.0 (6H, m), 3.0~3.2 (2H, m), 3.4~3.7 (4H, m), 3.90 (3H, s), 3.94 (3H, s), 6.7~7.0 (3H, m), 7.0~7.6 (5H, m).

Working Example 102

(E)-N-(((3-((N'-(2-(3,4-dimethoxyphenyl)ethyl)-N'-methyl)amino)propyl)))-3-(4-fluorobenzilidene)-2-piperidone

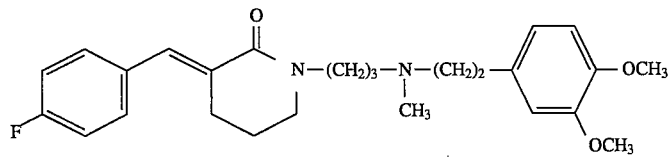

Slightly yellowish oily matter
NMR (CDCl$_3$) δ; 1.6~2.0 (4H, m), 2.32 (3H, s), 2.3~2.8 (8H, m), 3.2~3.6 (4H, m), 3.82 (3H, s), 3.84 (3H, s), 6.6~6.8 (3H, m), 6.9~7.4 (4H, m), 7.7 (1H, s).

Working Example 103

(E)-N-(((3-((N'-(2-(3,4-dimethoxyphenyl)ethyl)amino)propyl)))-3-(4-fluorobenzilidene)-2-pyrrolidinone

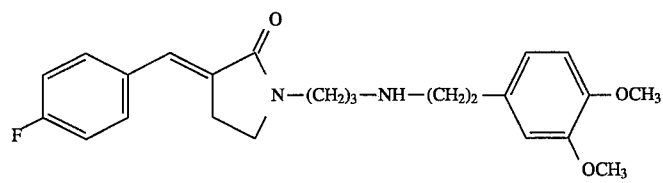

White solid matter
NMR (CDCl$_3$) δ; 1.7~2.0 (2H, m), 2.5~3.2 (1H, m), 3.1~3.4 (4H, m), 3.84 (3H, s), 3.86 (3H, s), 6.6~6.9 (3H, m), 6.9~7.6 (5H, m).

Working Example 104

(E)-N-(((3-((N'-(6,7-dimethoxy-1,2,3,4-)-tetrahydronaphthalene-2-yl)-N'-methyl)amino)propyl)))-3-(4-fluorobenzilidene)-2-pyrrolidinone

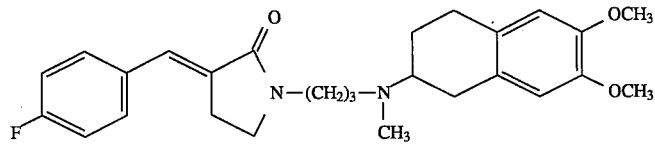

Slightly brownish solid matter
NMR (CDCl$_3$) δ; 1.5~2.2 (4H, m), 2.34 (3H, s), 2.4~3.2 (10H, m), 3.3~3.7 (4H, m), 3.83 (6H, s), 6.56 (2H, s), 6.9~7.6 (5H, m).

Working Example 105

(E)-N-(((3-((N'-(indane-2-yl)-N'-methyl)amino)propyl)))-3-(4-fluorobenzilidene)-2-pyrrolidinone

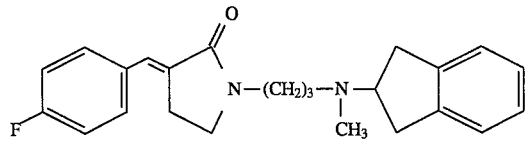

Slightly brown solid matter
NMR (CDCl$_3$) δ; 1.6~2.0 (2H, m), 2.27(3H, s), 2.3~2.6 (2H, m), 2.8~3.7 (11H, m), 6.8~7.6 (9H, m).

Working Example 106

(E)-N-(((3-((N'-(2-(3,4-dimethoxyphenyl)ethyl)-N'-methyl)amino)propyl)))-3-(4-cyanobenzilidene)-2-pyrrolidinone

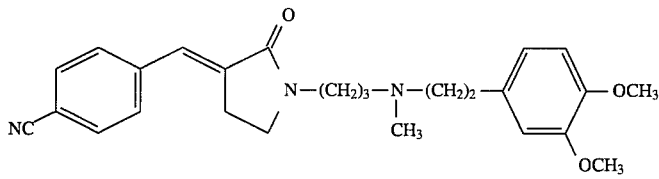

Slightly brownish oily matter
NMR (CDCl₃) δ; 1.6~2.0 (2H, m), 2.2~2.9 (9H, m), 2.9~3.3 (2H, m), 3.3~3.7 (4H, m), 3.84 (3H, s), 3.86 (3H, s), 6.6 ~6.9 (3H, m), 7.2~7.8 (5H, m).

Working Example 107

(E)-N-(((3-((N'-(2-(4-pyridyl)ethyl)-N'-methyl)amino)propyl)))-3-(3,4-(methylenedioxy)benzilidene)-2-pyrrolidinone

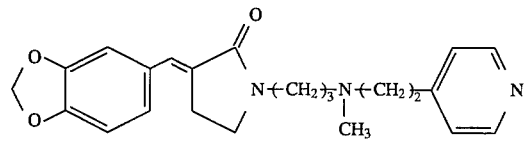

Yellow oily matter
NMR (CDCl₃) δ; 1.5~1.9 (2H, m), 2.2~3.2(11H, m), 3.3~3.6 (4H, m), 5.95 (2H, s), 6.7~7.3 (6H, m), 8.4~8.6 (2H, m).

Working Example 108

(E)-N-(((3-((N'-(2-(4-methoxyphenyl)ethyl)-N'-methyl)amino)propyl)))-3-(4-fluorophenyl)propeneamide

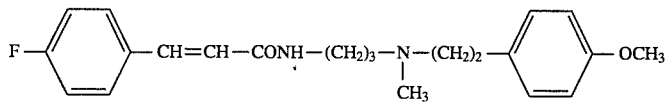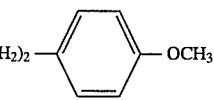

A mixture composed of 0.6 g of (E)-N-(3-chloropropyl)-3-(4-fluorophenyl)propeneamide, 0.75 g of N-methyl-N-(2-(4-methoxyphenyl)ethyl)amine hydrochloric acid, 0.91 g of potassium carbonate anhydride, tetraiodine-n-butylammonium (volume in catalyst) and 5 ml of N,N'-dimethylformamide was stirred at 80° C. for 7 hours. These were cooled down, water was added thereto, and extraction was conducted with chloroform. After drying up with sodium sulfuric anhydride, the solvent was distilled off. Then the residue was purified by means of silica gel column chromatography (solvent; chloroform:methanol=50:1) to obtain 0.38 g (yield: 41%) of the marked compound as yellow solid matter.

NMR (CDCl₃) δ; 1.5~1.9 (2H, m), 2.34 (3H, s), 2.4~2.9 (6H, m), 3.3~3.6 (2H, m), 3.72 (3H, s), 6.11 (1H, d, J=16Hz), 6.7~7.7 (10H, m).

Working Examples 109–120

The following compounds were obtained by the same method as in Working Example 108 above Working Example 109

(E)-N-(((3-((N'-(2-(4-methoxyphenyl)ethyl)-N'-aryl)amino)propyl)))-3-(4-fluorophenyl)propeneamide

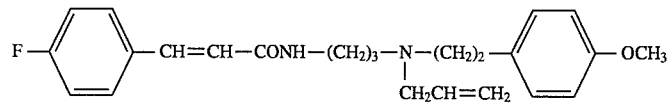

Yellow oily matter
NMR (CDCl₃) δ; 1.5–1.9 (2H, m), 2.5~2.8(6H, m), 3.10 (2H, d, J=7Hz), 3.2~3.5 (2H, m), 3.62 (3H, s), 5.0~5.3 (2H, m), 5.5~6.1 (2H, m), 6.6~7.6 (10H, m).

Working Example 110

(E)-N-(((3-((N'-(2-(3,4-dimethoxyphenyl)ethyl)-N'-aryl)amino)propyl)))-3-(4-fluorophenyl)propeneamide

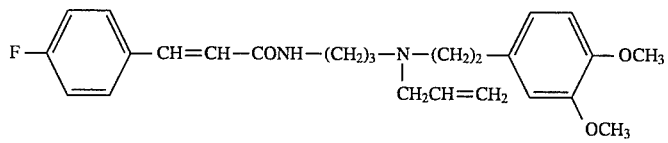

Yellow oily matter

NMR (CDCl₃) δ; 1.5~1.9 (2H, 2.5~2.9 (6H, m), 3.14 (2H, d, J=7Hz), 3.3~3.6(2H, m), 3.76 (3H, s). 3.84 (3H, s), 5.0~5.4 (2H, m), 5.6~6.0 (1H, m), 6.10 (1H, d, J=16Hz), 6.73 (3H, s), 6.9~7.5 (6H, m).

Working Example 111

(E)-N-(((3-((N'-(2-(3-methoxyphenyl)ethyl)-N'-methyl)amino)propyl)))-3-(4-fluorophenyl)propeneamide

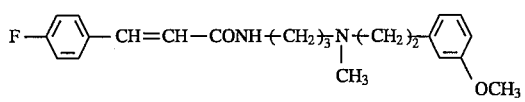

Yellow oily matter

NMR (CDCl₃) δ; 1.5~1.9 (2H, m), 2.29 (3H, s), 2.4~2.8 (6H, m), 3.3~3.5 (2H, m), 3.72 (3H, s), 5.98 (1H, d, J=16Hz), 6.6~7.6 (10H, m).

Working Example 112

(E)-N-(((3-((N'-(2-(3,4-methylenedioxy)phenyl)ethyl)-N'-methyl)amino)propyl)))-3-(4-fluorophenyl)propeneamide

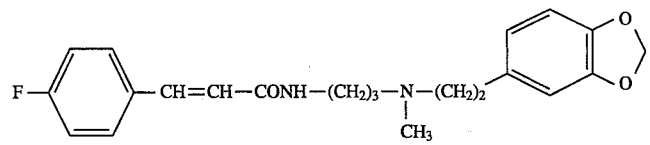

Yellow oily matter

NMR (CDCl₃) δ; 1.5~1.9 (2H, m), 2.28 (3H, s), 2.4~2.8 (6H, m), 3.3~3.6 (2H, m), 5.81 (2H, s), 6.12 (1H, d, J=16Hz). 6.69 (3H, s), 6.9~7.7 (6H, m).

Working Example 113

(E)-N-(((3-((N'-(2-(3,4-(ethylenedioxy)phenyl)ethyl)-N'-methyl)amino)propyl)))-3-(4-fluorophenyl)propeneamide

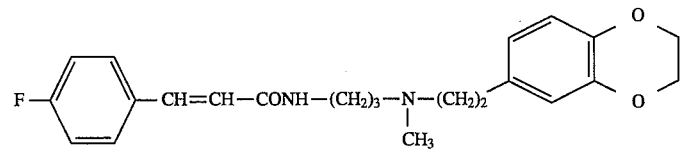

Slightly Yellowish oily matter

NMR (CDCl₃) δ; 1.5~1.8 (2H, m), 2.28 (3H, s), 2.4~2.8 (6H, m), 3.1~3.5 (2H, m), 4.10 (4H, s), 6.00 (1H, d, J=17Hz), 6.4~7.6 (9H, m).

Working Example 114

(E)-N-(((3-((N'-(4-(3,4-dimethoxyphenyl)piperidine-1-yl)propyl)))-3-(4-fluorophenyl)propeneamide

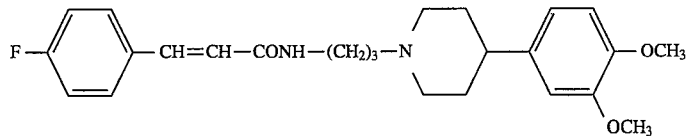

Blight Yellow oily matter

NMR (CDCl₃) δ; 1.6~2.7 (11H, m), 3.0~3.3(2H, m), 3.3~3.6 (2H, m), 3.80 (3H, s), 3.84 (3H, s), 6.28(1H, d, J=16Hz), 6.69 (3H, s), 6.8~7.1 (2H, m), 7.1~7.5 (3H, m), 7.6 (1H, hr).

Working Example 115

(E)-N-(((3-(7,8-dimethoxy-1,2,4,5-tetrahydro-3-benzadipine-3-yl)propyl-3-(4-fluorophenyl)propeneamide

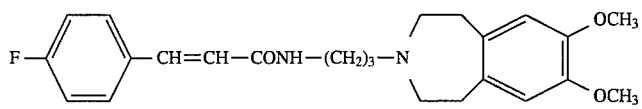

White amorphous matter
NMR (CDCl$_3$) δ; 1.6~2.0 (2H, m), 2.5~3.0 (10H, m), 3.3~3.6 (2H, m), 3.83 (6H, s), 6.25 (1H, d, J=16Hz), 6.59 (2H, s), 6.8~7.7 (6H, m).

Working Example 116

(E)-N-(((3-((3-(3,4-dimethoxyphenyl)pyrrolidine-1-yl)propyl)))-3-(4-fluorophenyl)propeneamide

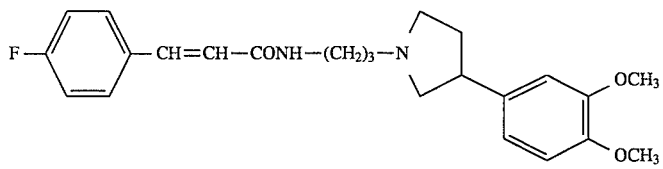

Blight yellow oily matter
NMR (CDCl$_3$) δ; 1.7~2.6 (3H, 2.7~3.7 (10H, m), 3.80 (3H, s), 3.86 (3H, s), 6.40 (1H, d, J=16Hz), 6.7~7.2 (5H, m), 7.3~7.6 (3H, m), 7.64 (1H, br).

Working Example 117

(E)-N-(((3-(3,4-dimethoxyphenyl)piperidine-1-yl)propyl-3-(4-fluorophenyl)propeneamide

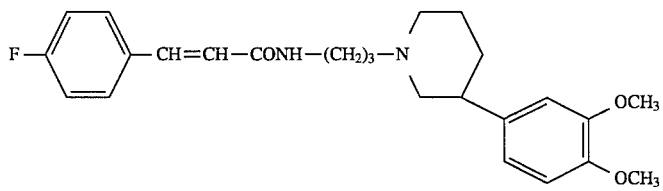

Blight yellow amorphous matter
NMR (CDCl$_3$) δ; 1.2~2.2 (7H, m), 2.5~2.7 (2H, m), 2.9~3.2 (2H, m), 3.3~3.6 (2H, m), 3.79 (6H, s), 6.27 (1H, d, J=16Hz). 6.6~6.8 (3H, m), 6.8~7.6 (6H, m).

Working Example 118

(E)-N-(((3-((2-(2-pyridyl)ethyl)-N'-methyl)amino)propyl)-3-(4-fluorophenyl)propeneamide

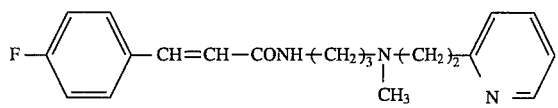

Yellow oily matter
NMR (CDCl$_3$) δ; 1.5~1.9 (2H, m), 2.24 (3H, s), 2.3~3.1 (6H, m), 3.2~3.5 (2H, m), 6.24 (1H, d, J=17Hz), 6.9~7.8 (9H, m), 8.4~8.6 (1H, m).

Working Example 119

(E)-N-(((3-(N'-(2-(3-pyridyl)ethyl)-N'-methyl)amino)propyl)))-3-(4-fluorophenyl)propeneamide

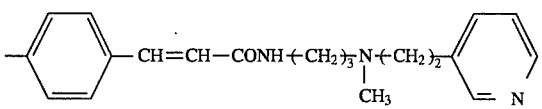

Yellow oily matter
NMR (CDCl$_3$) δ; 1.5~1.9 (2H, m), 2.32 (3H, s), 2.4~2.9 (6H, m), 3.3~3.6 (2H, m), 6.07 (1H, d, J=17Hz), 6.7 (1H, br), 6.9~7.4 (3H, m), 7.4~7.7 (4H, m), 8.4~8.6 (2H, m).

Working Example 120

(E)-N-(((3-((N'-(2-(4-pyridyl)ethyl)-N'-methyl)amino)propyl)))-3-(4-fluorophenyl)propeneamide

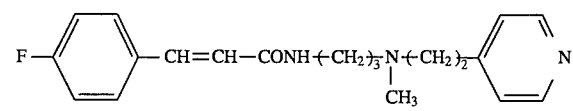

Yellow oily matter

NMR (CDCl$_3$) δ; 1.5~1.9 (2H, m), 2.32 (3H, s). 2.4~2.9 (6H, m), 3.3~3.6 (2H, m), 6.09 (1H, d, J=17Hz), 6.65 (1H, br), 6.9~7.2 (4H, m), 7.3~7.7 (3H, m), 8.4~8.6 (2H, m).

Examples of the compound III

Preparation Example 1

4-(1,2-dihydro-2-oxo-1-pyridyl)benzaldehyde

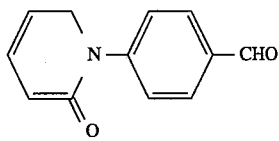

4.4 g of 60% sodium hydride was suspended into 150 ml of N,N-dimethylformamide, to which 10.78 g of 2-hydroxypyridine was added little by little at a room temperature. 30 min after, 12.4 g of 4-fluorobenzaldehyde was added and stirred at 120° C. for 3 hours. The reaction solution was concentrated under a reduced pressure and iced water was added, which was extracted with chloroform. After drying with anhydrous magnesium sulfate, the solvent was distilled off. Resultant crystals were washed with ethyl acetate to obtain 10.3 g of the above-captioned compound as fine gray powder (yield: 52%).

Melting point (°C.): 130–131

Elemental analysis value: As C$_{12}$H$_9$NO$_2$

|  | C | H | N |
|---|---|---|---|
| Theoretical value (%): | 72.35 | 4.55 | 7.03 |
| Measured value (%): | 72.51 | 4.66 | 7.12 |

NMR (CDCl$_3$) δ; 6.20(1H, dt, J=1.2Hz and 7.2Hz), 6.47 (1H, dd, J=1.2Hz and 7.2Hz), 7.1~7.6(4H, m), 7.8~8.0(2H, m), 10.04(1H, s).

Preparation Example 2

4-(3-methoxy-6-pyridazinyl)benzaldehyde

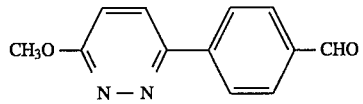

Under a nitrogen gas stream, 20 ml of a tetrahydrofuran solution of 12.31 g of 4-bromobenzaldehyde dimethyl acetal was dropped under stirring to a mixture of 1.14 g of magnesium, iodine (catalytic amount) and 30 ml of tetrahydrofuran, to prepare a Grignard reagent. The Grignard reagent thus prepared was dropped under a room temperature to a mixture of 7.00 g of 3-chloro-6-methoxypyridazine, 1.0 g of bis(1,3-diphenylphosphinopropane) nickel (II) chloride and 50 ml of tetrahydrofuran. After stirring at a room temperature for 20 hours, iced water and then 20 ml of 10% hydrochloric acid were added and stirred for 30 min. Tetrahydrofuran was distilled off under a reduced pressure and the residue was extracted with ethyl acetate. After drying with anhydrous sodium sulfate, the solvent was distilled off and the residue was purified on silica gel column chromatography (solvent: n-hexane - ethyl acetate), to obtain 4193 g (yield: 48%) of the above-captioned compound as pale orange solid.

Melting point (°C.): 139–141

Elemental analysis value : As C$_{12}$H$_{10}$N$_2$O$_5$

|  | C | H | N |
|---|---|---|---|
| Theoretical value (%): | 67.28 | 4.71 | 13.08 |
| Measured value (%): | 67.32 | 4.74 | 13.24 |

NMR (CDCl$_3$) δ; 5.18(3H, s), 7.02(1H, d, J=9.4Hz), 7.77 (1H, d, J=9.4Hz), 7.8~8.0 (2H, m), 8.0~8.2 (2H, m), 10.07 (1H, s).

The following compounds were synthesized in the same procedures as in the Preparation Example 2 except for using 2-chloropyridazine, 5-chloro-1-methyl-1,2-dihydro-2-oxopyridine, 3-chloro-6-tert-butylpyridazine, 5-chloro-2-(3,4-dimethoxyphenyl)methyl)pyridine respectively instead of 3-chloro-6-methoxypyridazine.

4-(2-pyradinyl)benzaldehyde

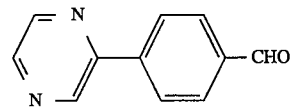

Melting point (°C.): 85.0–86.0

Elemental analysis value: As C$_{11}$H$_8$N$_2$O

|  | C | H | N |
|---|---|---|---|
| Theoretical value (%): | 71.73 | 4.38 | 15.21 |
| Measured value (%): | 71.83 | 4.48 | 15.17 |

NMR (CDCl$_3$) δ; 7.9~8.2 (4H, m), 8.4~8.7 (2H, m). 9.00 (1H, m), 10.00(1H, s).

4-(1-methyl-1,2-dihydro-2-oxo-5-pyridyl)benzaldehyde

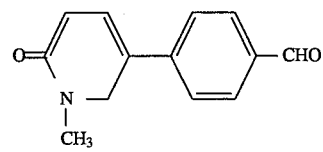

NMR (CDCl$_3$) δ; 3.61 (3H, s), 6.5~6.6 (2H, m), 7.5~7.7 (4H, m), 7.8~7.9(2H, m), 9.92(1H, s).

4-(2,3-dihydro-3-oxo-6-pyridazinyl)benzaldehyde

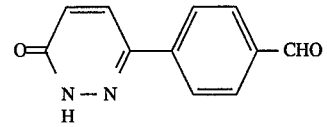

Melting point (°C.): 291–292

Elemental analysis value: As C$_{11}$H$_8$N$_2$O$_2$

|  | C | H | N |
|---|---|---|---|
| Theoretical value (%): | 65.99 | 4.03 | 14.00 |
| Measured value (%): | 66.21 | 4.15 | 14.02 |

NMR (CDCl$_3$) δ; 7.04 (1H, d, J=10.1Hz), 7.8~8.2 (5H, m), 10.06(1H, s), 13.38(1H, br).

4-(1,2-dihydro-2-oxo-5-pyridyl)benzaldehyde

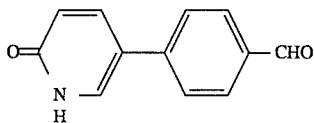

Melting point (°C.): 265–266.5
Elemental analysis value: $C_{12}H_9NO_2$

|  | C | H | N |
| --- | --- | --- | --- |
| Theoretical value (%): | 72.35 | 4.55 | 7.03 |
| Measured value (%): | 72.47 | 4.70 | 7.02 |

NMR (DMSO-$d_6$) δ; 6.4~6.6 (1H, m), 7.8~8.1 (6H, m), 10.04(1H, s), 12.0(1H, br).

Preparation Example 3

4-(2-methyl-1,3-thiazol-4-yl)benzaldehyde

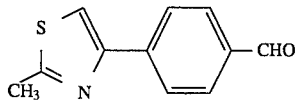

2.95 g of 4-(2-methyl-1,3-thiazol-4-yl)benznitrile was dissloved in 100 ml of benzene and thereto was added dropwise a solution in toluene (1.5M) of diisobutylalminum hydride at the room temperature. Agitation was made for 1 hour. An excess amount of sodium sulfate dihydrate was added to the mixture and the resultant was stirred at the room temperature. A filtrate liquid thereof was concentrated and purified with column chromatography using silica gel and dichloromethane to obtain 1.95 g of the intended compound with a yield of 68%.

NMR (CDCl$_3$) δ; 2.77 (3H, s), 7.47 (1H, s), 7.8–8.1 (4H, m), 10.00 (1H, s).

Preparation Example 4

4-(1,3-thiazol-4-yl)benzaldehyde

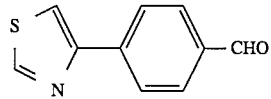

Production was made in the same was as shown in preparation example 3.

NMR (CDCl$_3$) δ; 7.70 (1H, d, J=2Hz), 7.8~8.2 (4H, m), 8.88 (1H, d, J=2Hz), 10.02 (1H, s).

Preparation Example 5

(E)-4-(4-(1,2-dihydro-2-oxo-1-pyridyl)phenyl)-3-butenoic acid

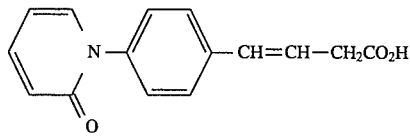

3.00 g of 4-(1,2-dihydro-2-oxo-1-pyridyl)benzaldehyde and 6.15 of β-carboxyethyltriphenyl phosphonium chloride were suspended into 30 ml of tetrahydrofuran, cooled to −50° C. and stirred. 20 ml of a tetrahydrofuran solution of 3.72 g of potassium-tert-butoxide was dropped and the temperature was gradually raised to 0° C. After 10 hours, iced water was added and the aqueous layer was washed with ether. The aqueous-layer was adjusted to about pH 3 with concentrated hydrochloric acid, and deposited crystals were collected by filtration to obtain 2.96 g of the above-captioned compound as pale brown yellow powder (yield: 77%).

Melting point (°C.): 218.5–221.5
Elemental analysis value: As $C_{15}H_{13}NO_3$

|  | C | H | N |
| --- | --- | --- | --- |
| Theoretical value (%): | 70.58 | 5.13 | 5.49 |
| Measured value (%): | 70.55 | 5.23 | 5.42 |

NMR (DMSO-$d_6$) δ; 3.22 (2H, d, J=5.7Hz), 6.1~6.4 (4H, m), 7.1~7.6 (6H, m).

The following compounds were obtained by the same procedures.

(E)-4-(4-(3-methoxy-6-pyridazinyl)phenyl)-3-butenoic acid

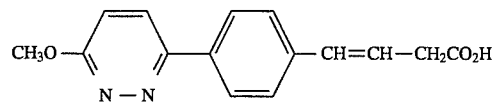

Melting point (°C.): 181–183
Elemental analysis value As $C_{15}H_{14}N_2O_3$

|  | C | H | N |
| --- | --- | --- | --- |
| Theoretical value (%): | 66.65 | 5.22 | 10.37 |
| Measured value (%): | 66.70 | 5.08 | 10.38 |

NMR (DMSO-$d_6$) δ; 3.18 (2H, d, J=5.7Hz), 4.04 (3H, s), 6.28 (1H, dt, J=5.7Hz and 15.8Hz), 6.52(1H, d, J=15.8Hz), 7.18(1H, d, J=9.7Hz), 7.3~7.6(2H, m), 7.8~8.2(3H, m).

(E)-4-(4-(2-pyradinyl)phenyl-3-butenoic acid

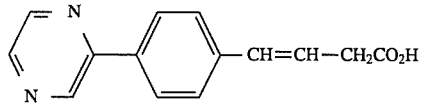

Melting point (°C.): 207.0–208.5
Elemental analysis value: As $C_{14}H_{12}NO_2$

|  | C | H | N |
| --- | --- | --- | --- |
| Theoretical value (%): | 69.99 | 5.03 | 11.66 |
| Measured value (%): | 69.77 | 5.09 | 11.07 |

NMR (DMSO-$d_6$) δ; 3.25(2H, d, J=6.0Hz), 6.43(1H, dt, J=6.0 Hz and 15.5Hz), 6.56(1H, d, J=15.5Hz), 7.60 (2H, d, J=8.0Hz), 8.10 (2H, d, J=8.0 Hz), 8.59(1H, d, J=3.0Hz), 8.70(1H, dd, J=1.0Hz and 3.0Hz), 9.25 (1H, d, J=1.0 Hz), 12.4 (1H, br s).

(E)-4-(4-((1-methyl-1,2-dihydro-2-oxo-5-py-ridyl)phenyl)-3-butenoic acid

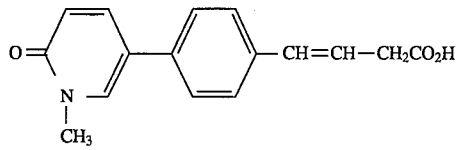

Melting point (°C.): 217.5–219.0 (decomp.)
Elemental analysis value: As $C_{16}H_{15}NO_3$

|  | C | H | N |
|---|---|---|---|
| Theoretical value (%): | 71.36 | 5.61 | 5.20 |
| Measured value (%): | 71.46 | 5.65 | 5.08 |

NMR (DMSO-$d_6$) δ; 3.21 (2H, d, J=5.0Hz), 3.51 (3H, s), 6.32 (1H, dt, J=5.0Hz and 16.0Hz), 6.47 (1H, d, J=9.0Hz), 6.47 (1H, d, J=16.0Hz), 7.4–7.6 (4H, m), 7.82 (1H, dd, J=3.0Hz and 9.0Hz), 8.14 (1H, d, J=3.0Hz).

(E)-4-(4-(2-methyl-1,3-thiazol-4-yl)phenyl)-3-butenic acid

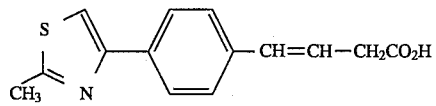

Melting point (°C.): 170°–171° C.
Elemental analysis value: $C_{14}H_{13}NO_2S$

|  | C | H | N | (S) |
|---|---|---|---|---|
| calcd. | 64.84 | 5.05 | 5.40 | 12.36 |
| found | 64.86 | 5.13 | 5.42 | 12.33 |

NMR (CDCl$_3$ and DMSO-$d_6$) δ; 2.73 (3H, s), 3.19 (2H, d, J=8Hz), 6.0–6.6 (2H, m), 7.2–8.0 (5H, m).

(E)-4-(4-1,3-thiazol-4-yl)phenyl)-3-butenic acid

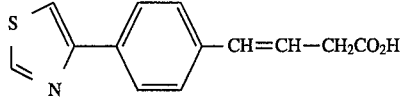

Melting point (°C.): 190°–191° C.
Elemental analysis value: $C_{13}H_{11}NO_2S$

|  | C | H | N | (S) |
|---|---|---|---|---|
| calcd. | 63.65 | 4.52 | 5.71 | 13.07 |
| found | 63.45 | 4.75 | 5.61 | 13.20 |

NMR (CDCl$_3$ and DMSO-$d_6$) δ; 3.20 (2H, d, J=6Hz), 6.1–6.7 (2H, m), 7.42 (2H, dt, J=1Hz, 8Hz), 7.07 (1H, d, J=2Hz), 7.89 (2H, dt, J=1Hz, 8Hz), 8.91 (1H, d, J=2Hz).

(E)-4-(2-(1H-imidazol-1-yl) thiophen-5-yl)-3-butenic acid

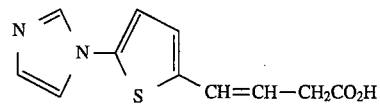

Melting point (°C.): 155.0–156.0
Elemental analysis value: As $C_{11}H_{10}N_2O_2S$

|  | C | H | N |
|---|---|---|---|
| Theoretical value (%): | 56.39 | 4.30 | 11.96 |
| Measured value (%): | 56.52 | 4.22 | 11.70 |

NMR (DMSO-$d_6$) δ; 3.16(2H, d, J=7.2Hz), 5.96(1H, dt, J=7.2 Hz and 15.8Hz), 6.50(1H, d, J=15.8Hz), 6.88 (1H, d, J=3.6Hz), 7.04 (1H, s), 7.10 (1H, d, J=3.6Hz), 7.54 (1H, m), 8.04 (1H, s).

(E)-4-(4-(1H-imidazol-1-yl) thiophen-2-yl)-3-butenic acid

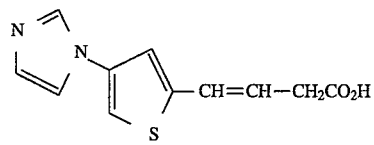

Melting point (°C.): 177.5–179.0
Elemental analysis value: As $C_{11}H_{10}N_2O_2S$

|  | C | H | N |
|---|---|---|---|
| Theoretical value (%): | 56.39 | 4.30 | 11.96 |
| Measured value (%): | 56.32 | 4.30 | 11.70 |

NMR (DMSO-$d_6$) δ; 3.18(2H, d, J=7.6Hz), 6.13(1H, dt, J=7.6 Hz and 15.8Hz.), 6.56(1H, d, J=15.8Hz), 6.97(1H, s), 7.43(1H, s), 7.49(1H, s), 7.61 (1H, s), 8.12(1H, s).

Preparation Example 6

(E)-4-(4-(2,3-dihydro-3-oxo-6-pyridazinyl)phenyl)-3-butenic acid

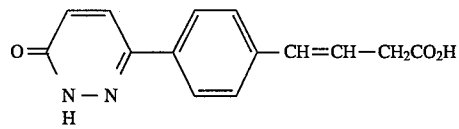

A mixture of 3.00 g of 4-(2,3-dihydro-3-oxo-6-pyridazinyl) benzaldehyde, 6.12 g of β-ethoxyethyltriphneyl phosphonium chloride and 50 ml of N,N-dimethylformamide was cooled to −50° C. and stirred. 20 ml of an N,N-dimethylformamide solution of 5.55 g of potassium tert-butoxide was dropped and the temperature was gradually raised to 0° C. After 2 hours, the temperature was elevated to a room temperature and stirring was conducted for further 10 hours. Iced water was added and the aqueous layer was washed with chloroform. The aqueous layer was adjusted to about pH 3 with hydrochloric acid and deposited solids were collected by filtration. They were recrystallized from 50% hydrous N,N-dimethylformamide to obtain 1.51 g of the above-captioned compound as pale orange powder (yield: 39%).

Melting point (°C.): 251–254

Elemental analysis value: As $C_{14}H_{12}N_2O_2$

|  | C | H | N |
|---|---|---|---|
| Theoretical value (%): | 65.61 | 4.72 | 10.93 |
| Measured value (%): | 65.76 | 4.70 | 10.91 |

NMR (DMSO-$d_6$) δ; 3.23 (2H, d, J=5.7Hz), 6.37 (1H, dt, J=5.7Hz and 15.8Hz). 6.59(1H, d, J=15.8Hz), 6.98 (1H, d, J=10.1Hz). 7.51 (2H, d, J=8.4Hz), 7.83(2H, d, J=8.4Hz), 8.03(1H, d, J=10.1Hz), 13.15(1H, br).

The following compounds were synthesized in the same procedures.

(E)-4-(4-(1,2-dihydro-2-oxo-5-pyridyl)phenyl)-3-butenoic acid

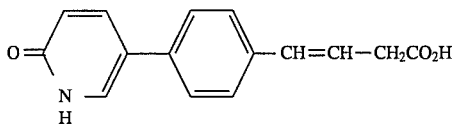

Melting point (°C.): 250 (decomposed)

Elemental analysis value $C_{15}H_{13}NO_3$

|  | C | H | N |
|---|---|---|---|
| calcd. (%) | 70.58 | 5.13 | 5,49 |
| found (%) | 70.67 | 5.21 | 5.29 |

NMR (DMSO-$d_6$) δ; 3.20 (2H, d, J=6Hz), 6.1~6.6 (3H, m), 7.2~7.6 (4H, m), 7.6~7.9 (2H, m), 12.0 (1H, br).

Preparation Example 7

Methyl N-(3,4-dimethoxyphenylacetyl)piperidine-2-carboxylate

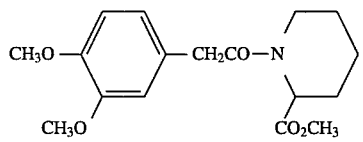

5.00 g of piperidine-2-carboxylic acid was dissolved into an aqueous 80 ml solution of saturated sodium hydrogen carbonate and stirred at a room temperature. 20 ml of an acetonitrile solution of 9-2 g of 3,4-dimethoxyphenyl acetyl chloride was dropped and stirred for 30 min. After washing the aqueous layer with ethyl acetate, the aqueous layer was adjusted to about pH 2 with concentrated hydrochloric acid and extracted with chloroform. Chloroform was distilled off and the resultant residue was refluxed for 6 hours with addition of 150 ml of methanol and 0.5 ml of concentrated sulfuric acid. After distilling off methanol, an aqueous diluted solution of sodium hydrogen carbonate was added and extracted with ethyl acetate. After drying with anhydrous magnesium sulfate, the solvent was distilled off and the residue was purified on silica gel column chromatography (solvent: n-hexane:ethyl acetate=1:1) to obtain 3.94 g of the above-captioned compound as yellow oil (yield: 32%).

NMR (CDCl$_3$) δ; 1.1~1.9(5H, m), 2.0~2.2(1H, m), 2.9~3.3(1H, m), 3.56(1H, d, J=14Hz), 3.68(3H, s), 3.78(1H, d, J=14Hz), 3.82(3H, s), 3.84(3H, s), 4.4~4.7 (1H, m), 5.40(1H, m), 7.76 (3H, s).

Preparation Example 8

N-(2-(3,4-dimethoxyphenyl)ethyl)piperidine-2-methanol

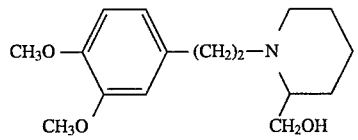

2.33 g of lithium aluminum hydride was suspended into 50 ml of tetrahydrofuran and stirred. 3.94 g of methyl N-(3,4-dimethoxyphenylacetyl)piperidine-2-carboxylate was dissolved in 20 ml of tetrahydrofuran, which was dropped and, thereafter, refluxed for 30 min. After cooling with ice and decomposing the excess reagent with ethyl acetate, 2.3 ml of water, 2.3 ml of an aqueous 15% solution of sodium hydroxide and 7 ml of water were added successively and, further, anhydrous magnesium sulfate was added and stirred. Insoluble matters were filtered out and the filtrate was washed thoroughly with tetrahydrofuran. The filtrate was concentrated and purified on silica gel column chromatography (solvent: dichloromethane:methanol:concentrated aqueous ammonium=1000:100:2), to obtain 2.77 g of the above-captioned compound as white solid (yield: 81%).

NMR (CDCl$_3$) δ; 1.1~1.8(6H, m), 2.2~3.2(8H, m), 3.44 (1H, dd, J=5Hz and 12Hz), 3.68 (1H, dd, J=4Hz and 12Hz), 3.81 (3H, s), 3.84 (3H, s), 6.5~6.8 (3H, m).

Preparation Example 9

N-(2-(3,4-dimethoxyphenyl)ethyl)piperidine-1-acetonitrile

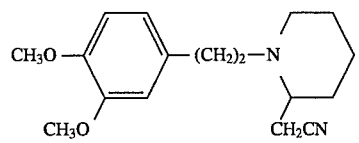

2.77 g of N-(2-(3,4-dimethoxyphenyl)ethyl)piperidine-2-methanol was dissolved in 30 ml off chloroform and cooled with ice. 0.87 ml of thionyl chloride was dropped and stirred at a room temperature for 48 hours. An aqueous solution of saturated sodium hydrogen carbonate was added and extracted with chloroform. After drying with anhydrous sodium sulfate, the solvent was distilled off and the residue was purified on silica gel column chromatography (solvent: dichloromethane:methanol=100:1) can be obtained 2.77 g of pale yellow oil. 1.21 g of potassium cyanate, dicyclohexyl-18-crown-6 (catalytic amount) and 20 ml of acetonitrile were added and refluxed for 24 hours. After allowing them to cool, an aqueous solution of potassium carbonate was added and extracted with ethyl acetate. After washing with water and drying with anhydrous sodium sulfate, the solvent was distilled off. The residue was purified on silica gel column chromatography (solvent: n-hexane:ethyl acetate=

2:1), to obtain 920 mg of the above-captioned compound as yellow oil (yield: 34%).

NMR (CDCl₃) δ; 1.3~1.8 (6H, m), 2.3~2.9 (9H, m), 3.84 (3H, s), 3.86 (3H, s), 6.8~6.9 (3H, m).

Preparation Example 10

N-(2-(3,4-dimethoxyphenyl)ethyl)-2-(2-aminoethyl)piperidine

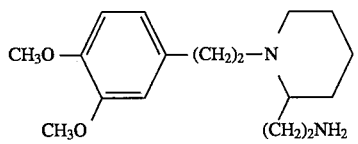

10 ml of a tetrahydrofuran solution of 920 mg of N-(2-(3,4-dimethoxyphenyl)ethyl)piperidine-2-acetonitrile was dropped at a room temperature to a mixture of 360 mg of aluminum lithium hydride and 10 ml of tetrahydrofuran. After stirring for 18 hours, it was cooled with ice, to which sodium sulfate-10 hydrate was added little by little and stirred violently for 30 min. The insoluble matters were filtered out and the filtrate was washed thoroughly with tetrahydrofuran. The filtrate was concentrated and purified on silica gel column chromatography (solvent: dichloromethane:methanol:concentrated aqueous ammonium= 200:20:1), to obtain 650 mg of the above-captioned compound as pale yellow oil (yield: 70%).

NMR (CDCl₃) δ; 1.1~2.0(8H, m), 2.0~3.1(10H, m), 3.5~3.7(1H, m), 3.84(3H, s), 3.87(3H, s), 6.6~6.9 (3H, m).

Preparation Example 11

(S)-N-(2-(3,4-dimethoxyphenyl)ethyl)pyrrolidine-2-methanol

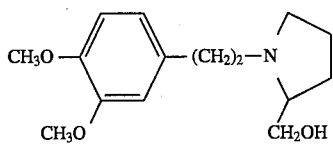

50 ml of acetonitrile was added to 1.0 g of 3-(+)-prolinole, 1.9 g of (2-(3,4-dimethoxyphenyl)ethyl)chloride and 1.64 g of anhydrous potassium carbonate and refluxed under heating for one day. After distilling off the solvent under a reduced pressure, about 50 ml of methylene chloride was added and deposited inorganic salts were filtered out. After distilling off methylene chloride under a reduced pressure, the residue was purified on silica gel column chromatography, to obtain 0.83 g of the above-captioned compound (yield: 32%).

NMR (CDCl₃) δ; 1.7~2.0 (4H, m), 2.3~3.4 (7H, m), 3.47 (1H, dd, J=4.0Hz and 11.0Hz), 3.66(1H, dd, J=4.0Hz and 11.0Hz), 3.88(3H, s), 3.91 (3H, s), 4.38 (1H, br, s), 6.7~6.9 (3H, m).

Preparation Example 12

(S)-N-(2-(3,4-dimethoxyphenyl)ethyl)pyrrolidine-2-acetonitrile

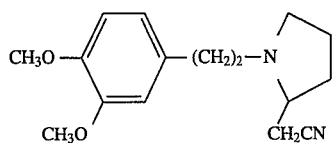

The above-captioned compound was obtained by the same procedures as those in Preparation Example 9 except for using (S)-N-(2-3,4-dimethoxyphenyl)ethyl)pyrrolidine-2-methanol as the starting material.

NMR (CDCl₃) δ; 1.5~3.1 (12H, m), 3.1~3.3 (1H, m), 3.81 (3H, s), 3.84 (3H, s). 6.6~6.8 (3H, m).

Preparation Example 13

(S)-N-(2-(3,4-dimethoxyphenyl)ethyl)-2-(2-aminoethyl) pyrrolidine

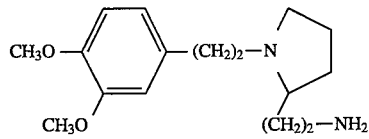

The above-captioned compound was obtained by the same procedures as those in Preparation Example 10 except for using (S)-N-(2-3,4-dimethoxyphenyl)ethyl)pyrrolidine-2-acetonitrile as the starting material.

NMR (CDCl₃) δ; 1.1~3.3(16H, m), 3.5~3.8(1H, m), 3.82 (3H, s), 3.84 (3H, s), 6.6~6.9 (3H, m).

Preparation Example 14

N-methyl-N-(2-(3,4-dimethoxyphenyl)propyl)-1,3-propane diamine

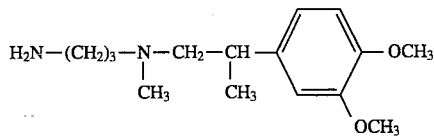

A mixture of 1.55 g of N-methyl-N-(2-(3,4-dimethoxyphenyl)propyl)amine, 1.98 g of N-(3-bromopropyl) phthalimide, 1.0 g of anhydrous potassium carbonate and 10 ml of acetonitrile was refluxed under heating for 6 hours. They were allowed to cool and then concentrated after filtering out insoluble matters. The residue was purified on silica gel column chromatography (solvent: chloroform:methanol= 100:1), to obtain 2.71 g of N-(3-(N'-(2-(3,4-dimethxoxyphenyl)propyl)-N'-methyl)amino)propyl)phthalimide as yellow oil. The product was dissolved in 20 ml of ethanol, to which 0.4 ml of hydrazine monohydrate was added and refluxed under heating for 2 hours. Deposited matters were filtered out and diluted aqueous solution of sodium hydroxide was added, which was extracted with chloroform. After drying with anhydrous sodium sulfate, the solvent was distilled off and the residue was purified on silica gel column chromatography (solvent: chloroform:methanol:concentrated aqueous ammonia: 100:10:1) to obtain 1.54 g of the above-captioned compound as yellow oil (yield: 78%).

NMR (CDCl₃) δ; 1.23 (3H, d, J=6.6Hz), 1.3~1.7 (2H, m), 2.20 (3H, s), 2.2~2.5 (4H, m), 2.5~3.1 (3H, m), 3.84 (3H, s), 3.87 (3H, s), 6.5~6.8(3H, m).

Preparation Example 15

N-methyl-N-(3-(3,4-dimethoxyphenyl)propan-2-yl)-1,3-propane diamine

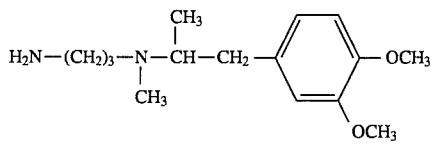

The above-captioned compound was obtained in the same procedures as those in preparation Example 13 by using N-methyl-N-(3-(3,4-dimethoxyphenyl)propan-2-yl)amine instead of N-methyl-N-(2-(3,4-dimethoxyphenyl)propyl)amine.

Yellow oil

NMR (CDCl₃) δ; 0.92 (3H, d, J=6.6Hz), 1.3~1.8 (4H, m), 2.1~3.1 (10H, m), 3.84 (3H, s), 3.86 (3H, s), 6.6~6.9 (3H, m).

Preparation Example 16

N-(1-benzylpyrrolidin-3-yl)phthalimide

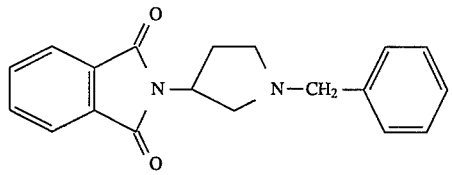

10.0 g of 3-amino-1-benzylpyrrolidine was dissolved into 10 ml of chloromethane, to which 12.4 g of N-ethoxycarbonylphthalimide was added and stirred at a room temperature for 10 hours. The solvent was distilled off, diethyl ether was added and insoluble matters were filtered out. The filtrate was concentrated and purified on silica gel column chromatography, to obtain 12.70 g of the above-captioned compound (yield: 73%)

NMR (CDCl₃) δ; 2.1~2.3 (2H, m), 2.6~3.1 (4H, m), 3.86 (2n, s), 4.7~5.1(1H, m), 7.1~7.3(5H, m), 7.6~7.8(4H, m).

Preparation Example 17

N-(1-(2-(3,4-dimethoxyphenyl)ethyl)pyrrolidin-3-yl) phthalimide

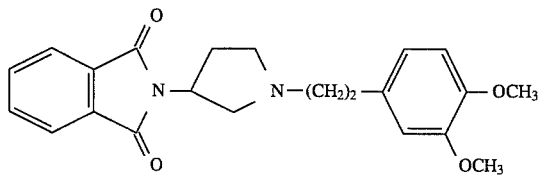

12.70 g of N-(1-benzylpyrrolidin-3-yl)phthalimide was dissolved in 100 ml of ethanol and then subjected to hydrogenating decomposition with addition of 1.0 g of 10% palladium-carbon and 5.2 ml of concentrated hydrochloric acid at 60° C. under 1 atm. After 12 hours, the catalyst was filtered out and the solvent was distilled off to obtain 11.03 g of N-(3-pyrrolidyl)phthalimide hydrochloride.

6.03 g of the hydrochloride was suspended into 100 ml of acetonitrile, to which 4.79 g of 2-(3,4-dimethoxyphenyl) ethyl chloride, 8.24 g of anhydrous potassium carbonate and n-tetrabutyl ammonium iodide (catalytic amount) were added and refluxed under heating for 20 hours. After allowing them to cool, the inorganic salts were filtered out and the solvent was distilled off. After adding ethyl acetate and washed with water, they were dried with anhydrous magnesium sulfate. The solvent was concentrated and purified on silica gel chromatography to obtain 1.03 g of the above-captioned compound (total yield: 6.5%).

NMR (CDCl₃) δ; 2.1~2.5 (2H, m), 2.6~3.2 (8H, m), 3.87 (3H, s), 3.90(3H, s), 4.95(1H, m), 6.80 (3H, bs), 7.6~7.9 (4H, m).

Preparation Example 18

3-amino-1-(2-(3,4-dimethoxyphenyl)ethyl)pyrrolidine

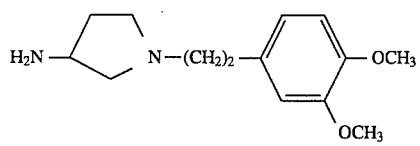

1.03 g of N-(1-(2-(3,4-dimethoxyphenyl)ethyl)pyrrolidin-3-yl)phthalimide was dissolved in 50 ml of ethanol, to which 2 ml of hydrazine monohydrate was added and refluxed under heating for 14 hours. The solvent was distilled off and an aqueous diluted solution of sodium hydroxide was added to the residue and extracted with chloroform. After drying with anhydrous magnesium sulfate, the solvent was distilled off, to obtain 0.68 g of the above-captioned compound (yield: 100%).

NMR (CDCl₃) δ; 1.4~1.7 (3H, m), 2.1~2.9(9H, m), 3.4 3.6(1H, m), 3.86(3H, s), 3.88(3H, s), 6.7~6.9 (3H, m).

Preparation Example 19

N-(3-((N'-(2-(3,5-dimethoxyphenyl)ethyl)-N'-methyl)amino)-2-hydroxypropyl)phthalimide

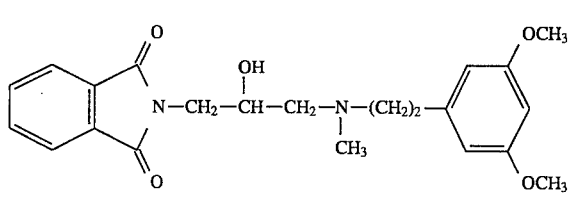

1.25 g of N-(2,3-epoxypropyl)phthalimide and 1.0 g of N-methyl-(2-(3,5-dimethoxyphenyl)ethyl)amine were dissolved in 50 ml of ethanol and stirred at 40° C. for 12 hours. After distilling off the solvent, the residue was purified on silica gel column chromatography, to obtain 1.90 g of the above-captioned compound as yellow oil (yield: 93%).

NMR (CDCl₃) δ: 2.32 (3H, s), 2.46 (2H, d, J=6.0Hz), 2.6~2.8 (4H, m), 3.4 (1H, brs), 3.8~4.1 (9H, m), 6.2~6.4 (3H, m), 7.6~7.9 (4H, m).

Preparation Example 20

N-methyl-N-(2-(3,5-dimethoxyphenyl)ethyl)-2-hydroxy-1,3-propane diamine

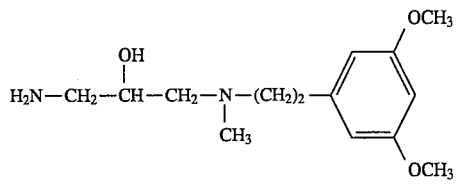

Using N-(3-((N'-(2-(3,5-dimethoxyphenyl)ethyl)-N'-methyl)amino)-2-hydroxypropyl)phthalimide as the starting material, a crude product was obtained in the same procedures as those in Preparation Example 18. Purification was effected by silica gel column chromatography (solvent: dichloromethane:methanol:concentrated aqueous ammonia), to obtain the above-captioned compound.

NMR (CDCl$_3$) δ; 2.15(3H, br s, exchangeble with D$_2$O), 2.3~2.5 (5H, m), 2.5~3.0 (6H, m), 3.4~3.7 (1H, m), 3.76 (6H, s). 6.32 (3H, br s).

Example 1

(E)-N-(3-((N'-(2-(3,4-dimethoxyophenyl)ethyl)-N'-methyl) amino)propyl)-4-(4-(pyradinyl)phenyl)-3-buteneamide

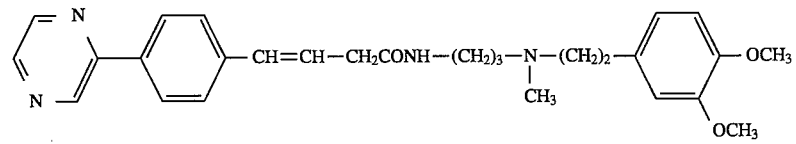

1.03 g of (E)-4-(4-(2-pyradinyl)phenyl)-3-butenic acid, 0.90 g of N,N'-dicyclohexylcarbodiimide, 0.59 g of N-hydroxybenzotriazole, 1.16 g of N-2-((3,4-dimethoxyphenyl)ethyl)-N-methyl-1,3-propane diamine and a mixture of 10 ml acetonitrile and 10 ml of water were stirred at 60° C. for 30 min. Deposited crystals were filtered out and the solution was concentrated under a reduced pressure. Purification was effected by silica gel column chromatography, to obtain 1.03 g of the above-captioned compound as pale yellow crystal.

Melting point (°C.): 84.5~86.0
Elemental analysis value: As C$_{28}$H$_{34}$N$_4$O$_3$

|  | C | H | N |
|---|---|---|---|
| Theoretical value (%): | 70.86 | 7.22 | 11.81 |
| Measured value (%): | 70.84 | 7.24 | 11.83 |

NMR (CDCl$_3$) δ; 1.5~1.9 (2H, m), 2.20 (3H, s), 2.2~2.7 (6H, m), 3.04 (2H, d, J=6.0Hz), 3.2~3.5 (2H, m), 3.80(6H, s), 6.28(1H, dt, J=6.0Hz, and 17.0Hz). 6.40 (1H, d, J=17.0Hz), 6.5~6.7 (3H, m), 7.18 (1H, br s), 7.3~7.4 (2H, m), 7.8~7.9 (2H, m), 8.3~8.5 (2H, m), 8.88 (1H, br s).

Examples 2–18

The following compounds were synthesized in the same procedures as those in Example 1.

Example 2

(E)-N-(3-((N'-(2-(3,4-dimethoxyphenyl)ethyl)-N'-methyl) amino)propyl)-4-(4-(3-methoxy-6-pyridazinyl)phenyl)-3-butenic acid

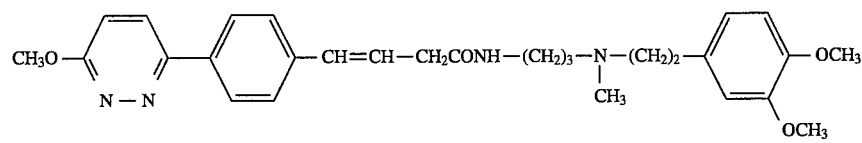

Melting point (°C.): 116~118
Elemental analysis value: As C$_{29}$H$_{36}$N$_4$O$_4$

|  | C | H | N |
|---|---|---|---|
| Theoretical value (%): | 69.02 | 7.19 | 11.10 |
| Measured value (%): | 69.06 | 7.17 | 11.04 |

NMR (CDCl$_3$) δ; 1.5~1.9 (2H, m), 2.3~2.8 (6H, m), 3.08 (2H, d, J=6.2Hz), 3.2~3.5 (2H, m), 3.82 (2H, s), 4.18(3H, s), 6.22(1H, dt, J=6.2Hz and 15.1Hz), 6.52 (1H, d, J=15.1Hz), 6.6~6.8 (3H, m), 7.02 (1H, d, J=9.2Hz), 7.27 (1H, br), 7.44 (1H, d, J=8.4Hz). 7.73(1H, d, J=9.2Hz), 7.93 (1H, d, J=8.4Hz).

Example 3

(E)-N-(3-((N'-(2-(3,4-dimethoxyphenyl)ethyl)-N'-methyl) amino)propyl)-4-(4-(1,2-dihydro-2-oxo-1-pyridyl)phenyl)-3-buteneamide

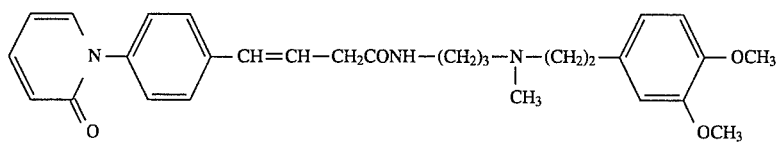

Melting point (°C.): 114–116
Elemental analysis value: As $C_{29}H_{35}N_3O_4 \cdot 1/4H_2O$

|  | C | H | N |
|---|---|---|---|
| Theoretical value (%): | 70.49 | 7.24 | 8.50 |
| Measured value (%): | 70.20 | 7.07 | 8.42 |

NMR (CDCl$_3$) δ; 1.5–1.9(2H, m), 2.16(3H, s), (6H, m), 3.06 (2H, d, J=6.2Hz), 3.1–3.5 (2H, m), 3.80 (3H, s), 3.82 (3H, s), 5.9–6.8 (7H, m), 6.9–7.5 (7H, m).

Example 4

(E)-N-(3-((N'-(2-(3,4-dimethoxyphenyl)ethyl)-N'-methyl) amino)propyl)-4-(4-((1-methyl-1,2-dihydro-2-oxo-5-pyridyl)phenyl)-3-buteneamide (yellow oil)

NMR (CDCl$_3$) δ; 1.5–1.8 (2H, m), 2.20 (2H, s), 2.4–2.8 (6H, m), 3.04 (2H, d, J=7Hz), 3.2–3.5 (2H, m), 3.78 (3H, s), 3.80 (3H, s), 6.1–6.5 (2H, m), 6.5–6.8 (4H, m), 7.2–7.8 (7H, m).

Example 6

(E)-N-(3-((N'-(2-(3,4-dimethoxyphenyl)ethyl)-N'-methyl) amino)propyl)-4-(4-(2,3-dihydro-3-oxo-6-pyridazinyl)phenyl)-3-buteneamide

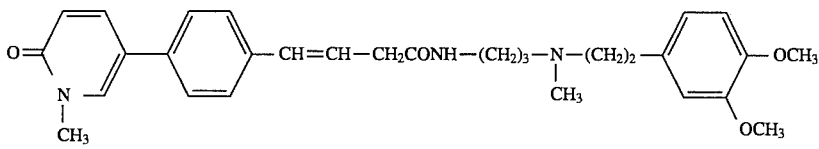

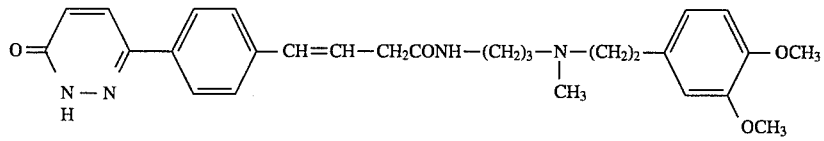

NMR (CDCl$_3$) δ; 1.5–1.9 (2H, m), 2.23 (3H, s), 2.4–2.7 (6H, m), 3.06 (2H, d, J=6Hz), 3.2–3.5 (2H, m), 3.60 (3H, s), 3.82 (3H, s), 3.83 (3H, s), 6.26 (1H, dt, J=6Hz and 16Hz), 6.43 (1H, d, J=16Hz), 6.5–6.8 (4H, m), 7.2–7.4 (5H, m), 7.46 (1H, d, J=3Hz), 7.58 (1H, dd, J=3Hz, 9Hz).

Example 5

(E)-N-(3-((N'-(2-(3,4-dimethoxyphenyl)ethyl)-N'-methyl) amino)propyl)-4-(4-(1,2-dihydro-2-oxo-5-pyridyl)phenyl-3-buteneamide (yellow solid)

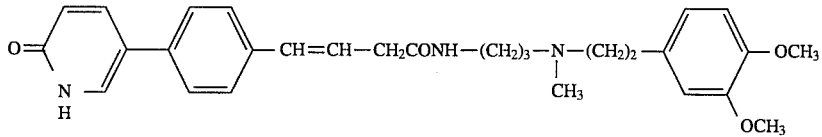

Melting point (°C.): 129–131
Elemental analysis value: As $C_{28}H_{34}N_4O_4 \cdot 1/4H_2O$

|  | C | H | N |
|---|---|---|---|
| Theoretical value (%): | 67.92 | 7.02 | 11.32 |
| Measured value (%): | 67.86 | 6.97 | 11.35 |

NMR (CDCl$_3$) δ; 1.5~1.9(2H, m), 2.21(3H, s), 2.3~2.8 (6H, m), 3.07(2H, d, J=5.7Hz), 3.2~3.5 (2H, m), 3.82(3H, s), 3.83(3H, s), 6.0~6.9(5H, m), 7.03(1H, d, J=9.7Hz), 7.2~7.5 (3H, m), 7.5~7.8(3H, m).

Example 7

(E)-N-(3-((N'-(2-(3,4-dimethoxyphenyl)ethyl)-N'-methyl) amino)propyl)-4-(4-(1,3-thiazol-4-yl)phenyl)-3-butene amide (light yellow oil)

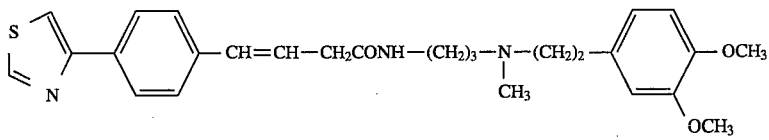

NMR (CDCl$_3$) δ; 1.4~1.9(2H, m), 2.14(3H, s), 2.3~2.7(6H, m), 3.04(2H, d, J=6Hz), 3.1~3.5(2H, m), 3.78(6H, s), 5.9~6.8(5H, m), 7.40(1H, brs), 7.44(1H, d, J=2Hz), 7.5~8.0(4H, m), 8.77(1H, d, J=2Hz).

Example 8

(E)-N-(3-((N'-(2-(3,4-dimethoxyphenyl)ethyl)-N'-methyl) amino)propyl)-4-(4-(2-methyl-1,3-thiazol-4-yl)phenyl)-3-butene amide (light yellow oil)

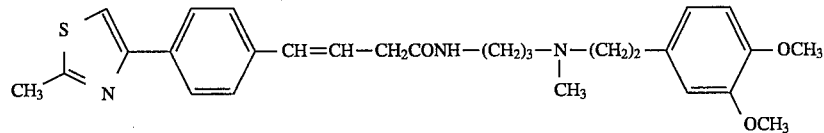

NMR (CDCl$_3$) δ; 1.4~1.9(2H, m), 2.15(3H, s), 2.3~2.9(9H, m), 3.05(2H, d. J=6Hz), 3.1~3.5(2H, m), 3.81(6H, s), 6.1~6.8(5H, m), 7.1~8.0(6H, m).

Example 9

(E)-N-(3-((N'-(2-(3,4-dimethoxyphenyl)ethyl)-N'-methyl) amino)propyl)-4-(4-(1H-imidazol-1-yl)thiophen-2-yl)-3-butene amide

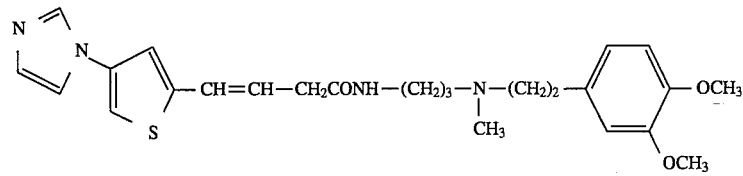

Yellow oil

NMR (CDCl$_3$) δ; 1.5~1.9(2H, m), 2.24(3H, s), 2.4~2.8 (6H, m), 2.97(2H, d, J=6.5Hz), 3.1~3.5 (2H, m), 3.78 (3H, s), 3.81 (3H, s), 6.08 (1H, dt, J=6.5Hz and 15.5Hz), 6.46(1H, d, J=15.5Hz), 6.6~6.8 (3H, m), 6.91 (2H, s), 7.0~7.2(2H, m), 7.30(1H, br), 7.68(1H, s).

Example 10

(E)-N-(3-((N'-(2-(3,4-dimethoxyphenyl)ethyl)-N'-methyl amino)propyl)-4-(2-(1H-imidazol-1-yl)thiophen-5-yl)-3-butene amide

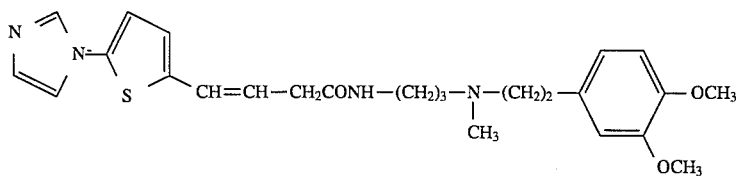

Yellow oil

NMR (CDCl$_3$) δ; 1.5~1.9(2H, m), 2.13(3H, s), 2.4~2.8 (6H, m), 2.96(1H, d, J=6.5Hz), 3.2~3.5 (2H, m), 3.80 (3H, s), 3.82 (3H, s), 5.97 (1H, dt, J=6.5Hz and 15.8Hz), 6.42(1H, d, J=15.8Hz), 6.6~6.9 (5H, m), 7.08 (2H, s), 7.28(1H, br), 7.64(1H, s).

Example 11

(E)-N-(N'-(2-(3,4-dimethoxyphenyl)ethyl)-3-pyrrolidino)-4-(4-(1H-imidazol-1-yl)phenyl)-3-butene amide

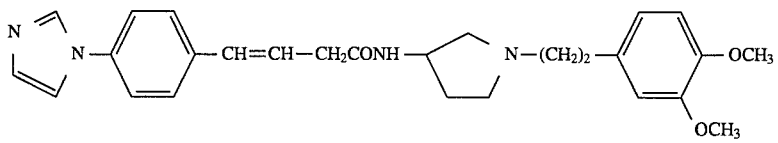

Yellow oil

NMR (CDCl$_3$) δ; 1.5~1.9(1H, m), 2.1~3.0(9H, m), 3.12 (2H, d, J=6.5Hz), 3.78 (3H, s), 3.80 (3H, s), 6.34 (1H, dt, J=6.5Hz and 17.0Hz), 6.44 (1H, d, J=17.0Hz), 6.6~6.8(4H, m), 7.11 (1H, br s), 7.2~7.5(5H, m), 7.77(1H, br s).

Example 12

(E)-N-(3-(3-(3,4-dimethoxyphenyl)-1-pyrrolidino) propyl-4-(4-(1H-imidazol-1-yl)phenyl)-3-butene amide

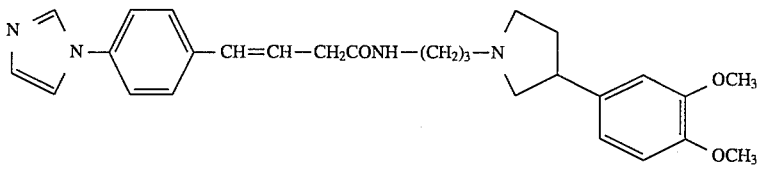

Yellow oil

NMR (CDCl$_3$—CD$_3$OD) δ; 1.7~2.0(2H, m), 2.0~2.4(1H, m), 2.5~3.5 (12H, m), 3.83 (3H, s), 3.86 (3H, s), 6.40(1H, dt, J=6.5Hz and 16.2Hz), 6.48 (1H, d, J=16.2Hz), 6.7~6.9(3H, m), 7.2~7.5 (6H, m), 7.81 (1H, m).

Example 13

(E)-N-(2-(N'-(2-(3,4-dimethoxyphenyl)ethyl)-2-pyrrolidino) ethyl)-4-(4-(1H-imidazol-1-yl)phenyl)-3-butene amide

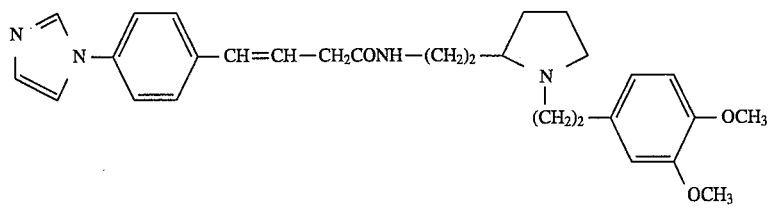

Yellow oil

NMR (CDCl₃) δ; 1.5~3.5(17H, m), 3.80(3H, s), 3.82(3H, s), 6.28(1H, dt, J=6.5Hz and 16.0Hz), 6.40(1H, d, J=16.0Hz), 6.5~6.8(3H, m), 7.1~7.4(7H, m), 7.75(1H, br s).

Example 14

(E)-N-(2-(N'-(2-(3,4-dimethoxyphenyl)ethyl)-2-pyperidino) ethyl)-4-(4-(1H-imidazol-1-yl)phenyl)-3-butene amide

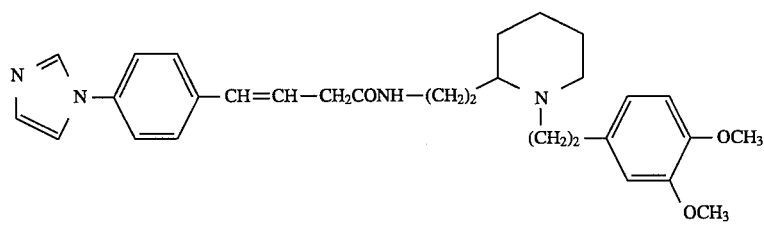

Yellow oil

NMR (CDCl₃) δ; 1.2~2.0(8H, m), 2.3~3.6(10H, m), 3.81 (3H, s), 3.84 (3H, s), 3.9~4.5 (1H, m), 6.24(1H, dt, J=6Hz and 16Hz), 6.45(1H, d, J=16Hz), 6.5~6.8 (3H, m), 7.0~7.5 (7H, m), 7.80(1H, s).

Example 15

(E)-N-(3-(N'-(2-(3,4-dimethoxyphenyl)propyl)-N'-methyl) amino)propyl)-4-(4-(1H-imidazol-1-yl)phenyl)-3-butene amide

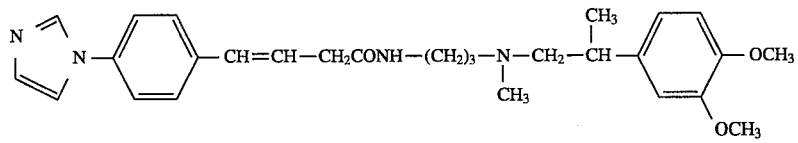

Yellow oil

NMR (CDCl₃) δ; 1.20 (3H, d, J=6.8Hz), 1.4~1.8 (2H, m), 2.13 (3H, s), 2.3~2.6 (4H, m), 2.6~3.0 (3H, m), 3.1~3.4(2H, m), 3.79 (3H, s), 3.84(3H, s), 6.13(1H, dt, J=5.8Hz and 15.1 Hz), 6.37 (1H, d, J=15.1Hz), 6.5~6.8 (3H, m), 6.90(1H, br), 7.1~7.5(6H, m), 7.76 (1H, s).

Example 16

(E)-N-(3-((N'-(3-(3,4-dimethoxyphenyl)-2-propyl)-N'-methylpropyl)-4-(4-(1H-imidazol-1-yl)phenyl)-3-butene amide

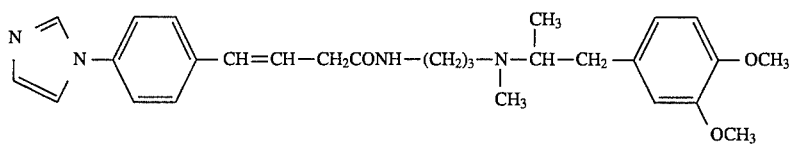

Yellow oil

NMR (CDCl$_3$) δ; 0.92 (3H, d, J=6.5Hz), 1.5~1.9 (2H, m), 2.23 (3H, s), 2.3~3.1 (5H, m), 3.3~3.5 (2H, m), 3.82 (3H, s), 3.84 (3H, s). 6.25 (1H, dt, J=6.2Hz and 15.8Hz), 6.50(1H, d, J=15.8Hz). 6.6~6.9 (3H, m), 7.1~7.6 (7H, m), 7.83 (1H, s).

Example 17

(E)-N-(3-((N'-(2-(3,4-dimethoxyphenyl)ethyl)-N'-methyl)amino)-2-hydroxypropyl)-4-(4-(1H-imidazol-1-yl)phenyl-3-buteneamide (light yellow, viscous liquid)

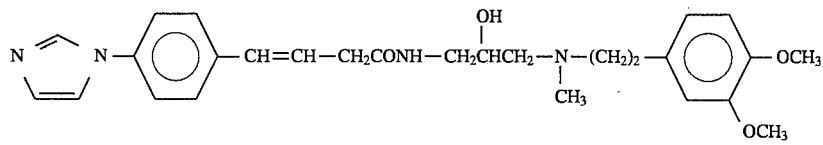

NMR (CDCl$_3$) δ; 2.32(3H, s), 2.4(2H, d, J=7Hz), 2.5~2.8(4H, m), 2.9~3.5(4H, m), 3.16(2H, d, J=7Hz), 3.8(3H, s), 3.84 (3H, s), 6.0~6.5(2H, m), 6.5~6.8(3H, m), 7.1~7.5(7H, m), 7.8(1H, s).

Example 18

(E)-N-(3-((N'-(2-(3,5-dimethoxyphenyl)ethyl)-N'-methyl)amino)-2-hydroxypropyl)-4-(4-(1H-imidazol-1-yl)phenyl)-3-butene amide (colorless oil)

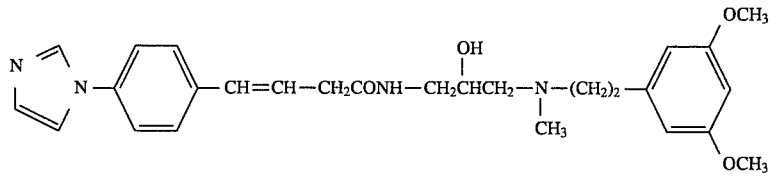

NMR (CDCl$_3$) δ; 2.32(3H, s), 2.39(2H, d, J=7.0Hz), 2.5~2.8(4H, m), 3.0~3.8(12H, m), 6.1~6.4(4H, m), 6.50(1H, d, J=16.0Hz), 7.1~7.5(6H, m), 7.83(1H, br s).

Example 19

(E)-N-(3-(1-(2-(3,4-dimethoxyphenyl)ethyl)-3-morpholino)methyl)-4-(4-(1H-imidazol-1-yl)phenyl)-3-buteneamide

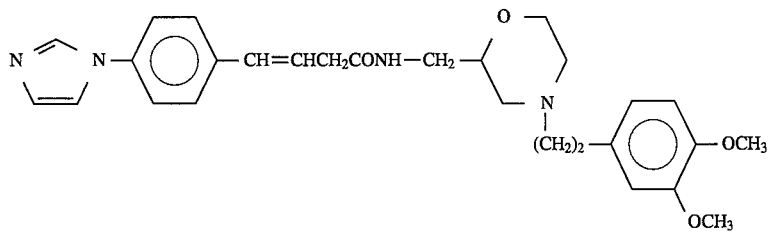

NMR (CDCl₃) δ; 1.8~2.2(2H, m), 2.2~3.0(6H, m), 3.0~3.4(3H, m), 3.4~4.1(10H, m), 6.16(1H, brs), 6.32(1H, dt, J=6.1Hz, 15.5Hz), 6.48(1H, d, J=15.5Hz), 6.7~6.8(3H, m), 7.14(1H, brs), 7.2~7.5(5H, m), 7.80(1H, brs).

Example 20

(E)-N-(1-(2-(3,4-dimethoxyphenl)ethyl)-4-pyperidino)-4-(4-(1H-imidazol-1-yl)phenyl)-3-buteneamide

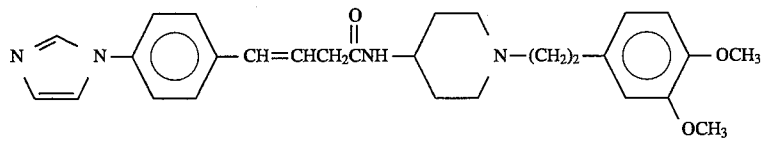

mp 161°–161.5° C. $C_{28}H_{34}N_4O_3$

|  | C | H | N |
|---|---|---|---|
| calcd. | 70.86 | 7.22 | 11.81 |
| found | 70.98 | 7.33 | 11.80 |

NMR (CDCl₃) δ; 1.1~1.7(2H, m), 1.8~2.3(4H, m), 2.4~3.0(6H, m), 3.14(2H, d, J=6.5Hz), 3.75(1H, m), 3.86(3H, s), 3.88(3H, s), 5.64(1H, br d, J=7Hz), 6.29(1H, dt, J=6.5Hz, 15.1Hz), 6.53(1H, d, J=15.1Hz), 6.6~6.8(3H, m), 7.1~7.6(6H, m), 7.81(1H, s).

We claim:

1. A butenoic or propenoic acid derivative having the formula (II) or a pharmacologically acceptable salt thereof:

$$G-C(R^{11})=C(R^{12})-(CH_2)_m-C(=X)-N(R^2)-A-N(R^3)-(CH_2)_n-J \quad (II)$$

which is defined by each of the following definitions A, B and C:

A in which in the formula (II) G is R1-phenyl, $R^{11}$ and $R^{12}$ each are hydrogen, m is one and X is oxygen,

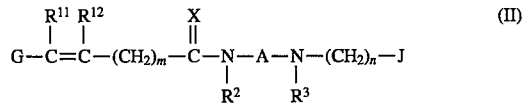

$$(I)$$

wherein R1 is a pyrrolyl, pyrazoyl, indolyl, indazolyl, isoquinolyl, quinoxalinyl, quinazolinyl or imidazopyridyl group, $R^2$ and $R^3$ each are hydrogen, a lower alkyl, a cycloalkyl or an allyl group, or $R^2$ and $R^3$ form a 5- to 7-membered saturated heterocyclic ring together with the nitrogen atom to which they are bonded, A is an alkylene group having 1 to 6 carbon atoms, which alkylene have a lower alkyl, a lower alkoxy or hydroxy substituted thereon, J is pyridyl or a phenyl having substituents $R^4$, $R^5$ and $R^6$:

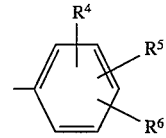

which $R^4$, $R^5$ and $R^6$ each are hydrogen, a halogen atom, a lower alkyl, a lower alkoxy, hydroxy, nitro, cyano, trifluoromethyl, an alkylsulfonyloxy, —$NR^7R^8$, $R^7$ and $R^8$ being hydrogen or a lower alkyl, or an alkanoylamino, or two of $R^4$, $R^5$ and $R^6$ form an alkylenedioxy together with two adjacent carbon atoms on the phenyl, or $R^4$, $R^5$ and $R^6$ form a 5- to 7-membered ring together with the —$(CH_2)_n$—, wherein n is an integer of from 1 to 6;

B in which in formula II: G is naphthyl or a phenyl having substituents $R^{15}$ and $R^{16}$:

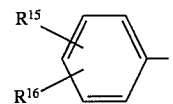

$R^{15}$ and $R^{16}$ are hydrogen, a lower alkyl, a lower alkoxy, a halogen, —$NR^7R^8$, wherein $R^7$ and $R^8$ are hydrogen or lower alkyl, cyano, trifluoromethyl, an alkanoylamino, trifluoroalkoxy, an alkylsulfonyl, nitro, hydroxyl, an alkylthio, an alkylsulfonylamino, an alkylcarbonylamino or a carbamoyl, or $R^{15}$ and $R^{16}$ forms a cyclic ring together with oxygen between two adjacent carbon atoms, $R^{11}$ and $R^{12}$ each are cyano, a lower alkyl, or a halogen or $R^{11}$ and $R^{12}$ form a cyclic ring together with oxygen and the carbon on the phenyl, m is zero or 1, X is oxygen or sulfur, $R^2$ and $R^3$ each are hydrogen, a lower alkyl, a lower alkoxy, a cycloalkyl, a trifluoroalkyl or a lower alkenyl, or $R^2$ and $R^3$ form a 5- to 7-membered saturated heterocyclic ring together with the nitrogen atom to which they are bonded, or $R^2$ forms a ring together with $R^{12}$, or $R^3$ forms a ring having a nitrogen atom together with the —$(CH2)_n$—, or $R^2$ forms a 5- to 7-membered saturated heterocyclic ring together with A, or $R^3$ forms a 5- to 7-membered saturated heterocyclic ring together with A, A is an alkylene group having 1 to 6 carbon atoms, which alkylene may have a lower alkyl group, n is an integer of 1 to 6, J is pyridyl or a phenyl having substituents $R^4$, $R^5$ and $R^6$:

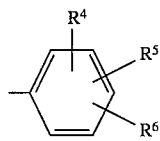

which $R^4$, $R^5$ and $R^6$ each are hydrogen, a halogen atom, a lower alkyl, a lower alkoxy, hydroxy, nitro, trifluoromethyl, an alkylsulfonyloxy, —$NH^7R^8$, wherein $R^7$ and $R^8$ are hydrogen or lower alkyl, or an alkanoylamyl, or two of $R^4$, $R^5$ and $R^6$ may form an alkylenedioxy together with two adjacent carbon atoms on the phenyl, or J may form a cyclic ring having a nitrogen together with the group —(CH2)$_n$—; and C in which in the formula (II) G is

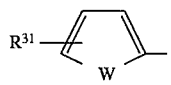

$R^{11}$ and $R^{12}$ are hydrogen, X is oxygen,

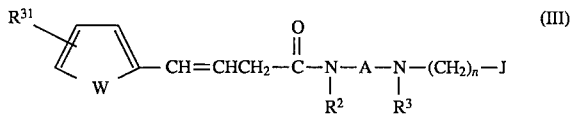

wherein $R^{31}$ is a hetero-aryl group, $R^2$ and $R^3$ each are hydrogen, a lower alkyl, a cycloalkyl or allyl, or $R^3$ forms a 5- to 7-membered saturated heterocyclic ring together with the nitrogen and the —(CH2)$_n$—, or $R^3$ forms a 5- to 7-membered cyclic heteroring having nitrogen or nitrogen and oxygen together with A and the nitrogen, A is an alkylene having 1 to 3 carbon atoms which may have a lower alkyl, hydroxy or a lower alkoxy group substituted thereon, W is oxygen or sulfur, J is pyridyl or a phenyl having substituents $R^4$, $R^5$ and $R^6$, which is hydrogen, a halogen, a lower alkyl, a lower alkoxy, hydroxy, nitro, cyano, trifluoromethyl, an alkylsulfonyloxy, —$NR^7R^8$, wherein $R^7$ and $R^8$ are hydrogen or lower alkyl group, or an alkanoylamino, or two of $R^4$, $R^5$ and $R^6$ form an alkylenedioxy together with two adjacent carbon atoms on the phenyl, one of $R^4$, $R^5$ and $R^6$ forms a 5- to 7-membered cyclic ring together with the group —(CH2)$_n$—, n is an integer of 1 to 6, or —(CH2)$_n$— may have a lower alkyl substituted thereon.

2. A 4-phenyl-3-butenoic acid derivative as claimed in claim 1, having the formula (I) and the definition (I) and a pharmacologically acceptable salt thereof.

3. A butenoic or propionic acid derivative as claimed in claim 1, having the formula (II) and the definition (II) and a pharmacologically acceptable salt thereof.

4. A 4-aryl-3-butenoic acid derivative as claimed in claim 1, having the formula (III) and the definition (III) and a pharmacologically acceptabel salt thereof.

5. The 4-phenyl-3-butenoic acid derivative as claimed in claim 2, in which R1 is pyrrolyl.

6. The 4-phenyl-3-butenoic acid derivative as claimed in claim 2, in which 1-pyrrolyl or 3-pyrrolyl.

7. The 4-phenyl-3-butenoic acid derivative as claimed in claim 2, in which n is an integer of 1 to 3.

8. The 4-phenyl-3-butenoic acid derivative as claimed in claim 2, in which J is the phenyl having a substituent(s), R4 is a lower alkoxy, R5 is a lower alkoxy and R6 is hydrogen.

9. The 4-phenyl-3-butenoic acid derivative as claimed in claim 2, in which J is m,p-dimethoxyphenyl, m-dimethoxyphenyl or m,m,p-trimethoxyphenyl.

10. The 4-phenyl-3-butenoic acid derivative as claimed in claim 2, which is selected from the group consisting of:

(E)-N-[3-((N'-(2-(3,4-Dimethoxyphenyl)ethyl)-N'-methyl)amino)propyl]-4-(4-(1H-pyrrol-1-yl)phenyl)-3-butenamide (E)-N-[3-((N'-(2-(3,4-Dimethoxyphenyl)ethyl)-N'-methyl)amino)propyl]-4-(4-(1H-1,2,4-triazol-1-yl)phenyl)-3-butenamide (E)-N-[3-((N'-(2-(3,4-Dimethoxyphenyl)ethyl)-N'-methyl)amino)propyl]-4-(4-(1H-pyrazol-1-yl)phenyl)-3-butenamide (E)-N-[3-((N'-(2-(3,4-Dimethoxyphenyl)ethyl)-N'-methyl)amino)propyl]-4-(4-(1,3-oxazol-5-yl)phenyl)-3-butenamide and (E)-N-[3-((N'-(2-(3,4-Dimethoxyphenyl)ethyl)-N'-methyl)amino)propyl]-4-(4-(4(1H)-pyridon-1-yl)phenyl)-3-butenamide.

11. A 4-aryl-3-butenoic acid derivative as claimed in claim 4, in which W is sulfur (—S—).

12. A 4-aryl-3-butenoic acid derivative as claimed in claim 4, in which A is a lower alkyl having 1 to 3 carbon atoms.

13. A 4-aryl-3-butenoic acid derivative as claimed in claim 4, in which R2 is hydrogen.

14. A 4-aryl-3-butenoic acid derivative as claimed in claim 4, which is selected from the group consisting of:

(E)-N-(3-((N'-(2-(3 ,4-dimethoxyphenyl)ethyl)-N'-methyl)amino)propyl)-4-(4-(2-pyrazinyl)phenyl)-3-buteneamide, (E)-N-(3-((N'-(2-(3,4-dimethoxyphenyl)ethyl)-N'-methyl)amino)propyl)-4-(4-(1,3-thiazol-4-yl)phenyl)-3-buteneamide, (E)-N-(3-((N'-(2-(3,4-dimethoxyphenyl)ethyl)-N'-methyl)amino)propyl)-4-(4-(2-methyl-1,3-thiazol-4-yl)phenyl)-3-buteneamide, (E)-N-(3-((N'-(2-(3,4-dimethoxyphenyl)ethyl)-N'-methyl)amino)propyl)-4-(3-(1H-imidazol-1-yl)thiophene-5-yl)-3-buteneamide, (E)-N-(3-((N'-(2-(3,4-dimethoxyphenyl)ethyl)-N'-methyl)amino)propyl)-4-(2-(1H-imidazol-1-yl)-thiophene-5-yl)-3-buteneamide, (E)-N-(N'-(2-(3,4-dimethoxyphenyl)ethyl)-3-pyrrolidinyl)-4-(4-(1H-imidazol-1-yl)phenyl)-3-buteneamide, (E)-N-(2-(N'-(2-(3,4-dimethoxypehnyl)ethyl)-2-pyrrolidinylethyl)-4-(4-(1H-imidazol-1-yl)phenyl)-3-buteneamide, (E)-N-(2-(N'-(2-(3,4-dimethoxyphenyl)ethyl)-2-pyperidinoethyl)-4-(4-(1H-imidazol-1-yl)phenyl)-3-buteneamide, (E)-N-(3-((N'-(2-(3,5-dimethoxyphenyl)ethyl)-N'-methyl)amino)-2-hydroxypropyl)-4-(4-(1H-imidazol-1-yl)phenyl)-3-buteneamide and (E)-N-(1-(2-(3,4-dimethoxyphenyl)ethyl)-4-piperidinyl)-4-(4-(1H-imidazol-1-yl)phenyl)-3-buteneamide.

15. A pharmacological composition which comprises a pharmacologically effective amount of the butenoic or propenoic acid derivative as defined in claim 1 and a pharmacologically acceptable carrier.

16. A method for treating, preventing, remitting or ameliorating ischemic heart diseases by administering the butenoic or protenoic acid derivative as defined in claim 1 in a pharmacologically effective amount to a human being in need thereof.

* * * * *